US010793621B2

(12) United States Patent
Bossenmaier et al.

(10) Patent No.: US 10,793,621 B2
(45) Date of Patent: Oct. 6, 2020

(54) NUCLEIC ACID ENCODING DUAL FC ANTIGEN BINDING PROTEINS

(71) Applicant: Hoffmann-La Roche Inc., Little Falls, NJ (US)

(72) Inventors: Birgit Bossenmaier, Seefeld (DE); Hubert Kettenberger, Munich (DE); Christian Klein, Bonstetten (CH); Klaus-Peter Kuenkele, Marzling (DE); Joerg-Thomas Regula, Munich (DE); Wolfgang Schaefer, Mannheim (DE); Manfred Schwaiger, Wang-Bergen (DE); Claudio Sustmann, Munich (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/961,699

(22) Filed: Apr. 24, 2018

(65) Prior Publication Data

US 2018/0312573 A1 Nov. 1, 2018

Related U.S. Application Data

(62) Division of application No. 13/406,411, filed on Feb. 27, 2012, now Pat. No. 9,982,036.

(30) Foreign Application Priority Data

Feb. 28, 2011 (EP) .................................... 11156320

(51) Int. Cl.

| | |
|---|---|
| ***C07K 16/30*** | (2006.01) |
| ***C12N 15/13*** | (2006.01) |
| ***C12N 5/10*** | (2006.01) |
| ***C07K 16/00*** | (2006.01) |
| ***C07K 16/28*** | (2006.01) |
| ***C07K 16/32*** | (2006.01) |
| ***C12N 15/85*** | (2006.01) |

(52) U.S. Cl.

CPC .......... *C07K 16/00* (2013.01); *C07K 16/2863* (2013.01); *C07K 16/32* (2013.01); *C12N 15/85* (2013.01); *C07K 2317/41* (2013.01); *C07K 2317/64* (2013.01); *C07K 2317/66* (2013.01); *C07K 2317/732* (2013.01); *C07K 2317/76* (2013.01); *C07K 2317/77* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | |
|---|---|---|---|
| 4,150,149 | A | 4/1979 | Wolfsen et al. |
| 4,361,544 | A | 11/1982 | Goldberg |
| 4,444,744 | A | 4/1984 | Goldberg |
| 4,737,456 | A | 4/1988 | Weng et al. |
| 5,202,238 | A | 4/1993 | Fell, Jr. et al. |
| 5,204,244 | A | 4/1993 | Fell et al. |
| 5,571,894 | A | 11/1996 | Wels et al. |
| 5,587,458 | A | 12/1996 | King et al. |
| 5,677,425 | A | 10/1997 | Bodmer et al. |
| 5,731,168 | A | 3/1998 | Carter et al. |
| 5,747,654 | A | 5/1998 | Pastan et al. |
| 5,798,229 | A | 8/1998 | Strittmatter et al. |
| 5,821,333 | A | 10/1998 | Carter et al. |
| 5,821,337 | A | 10/1998 | Carter et al. |
| 5,840,523 | A | 11/1998 | Simmons et al. |
| 5,869,046 | A | 2/1999 | Presta et al. |
| 5,959,083 | A | 9/1999 | Bosslet et al. |
| 5,959,177 | A | 9/1999 | Hein et al. |
| 6,040,498 | A | 3/2000 | Stomp et al. |
| 6,166,185 | A | 12/2000 | Davis et al. |
| 6,171,586 | B1 | 1/2001 | Lam et al. |
| 6,194,551 | B1 | 2/2001 | Idusogie et al. |
| 6,239,259 | B1 | 5/2001 | Davis et al. |
| 6,248,516 | B1 | 6/2001 | Winter et al. |
| 6,267,958 | B1 | 7/2001 | Andya et al. |
| 6,417,429 | B1 | 7/2002 | Hein et al. |
| 6,420,548 | B1 | 7/2002 | Vézina et al. |
| 6,511,663 | B1 | 1/2003 | King et al. |
| 6,558,672 | B1 | 5/2003 | Pastan et al. |
| 6,586,207 | B2 | 7/2003 | Tirrell et al. |
| 6,602,684 | B1 | 8/2003 | Umana et al. |
| 6,737,056 | B1 | 5/2004 | Presta |
| 6,897,044 | B1 | 5/2005 | Braslawsky et al. |
| 6,946,292 | B2 | 9/2005 | Kanda et al. |
| 6,982,321 | B2 | 1/2006 | Winter |
| 7,125,978 | B1 | 10/2006 | Vézina et al. |
| 7,129,330 | B1 | 10/2006 | Little et al. |

(Continued)

FOREIGN PATENT DOCUMENTS

| | | | |
|---|---|---|---|
| CA | 2853230 | A1 | 5/2013 |
| CN | 1173878 | A | 2/1998 |

(Continued)

OTHER PUBLICATIONS

Wall et al. (Theriogenology, vol. 45, p. 57-68, 1996) (Year: 1996).*
Houdebine et al. (Journal of Biotechnology, vol. 34, p. 269- 287, 1994) (Year: 1994).*
Kappell et al. (Current Opinions in Biotechnology, vol. 3, p. 548-553, 1992) (Year: 1992).*
Nagaoka (Protein Engineering, vol., 16, No. 4, p. 243-245, 2003) (Year: 2003).*
Chitnis (Clinical Cancer Research, vol. 14, p. 6364-6370, 2008) (Year: 2008).*
Caron (Journal of Experimental Medicine, vol. 176, p. 1191-1195, 1992) (Year: 1992).*
Stevenson (Anti-Cancer Drug Design, vol. 3, Ptg. 219-230, 1989) (Year: 1989).*
Morrison (Nature Biotechnology, vol. 25, No. 11, p. 1233-1234, 2007) (Year: 2007).*

(Continued)

*Primary Examiner* — Michael Allen
(74) *Attorney, Agent, or Firm* — Morrison & Foerster LLP

(57) ABSTRACT

The present invention relates to antigen binding proteins comprising two Fc parts, methods for their production, pharmaceutical compositions containing said antigen binding proteins, and uses thereof.

5 Claims, 15 Drawing Sheets

Figure 1A:
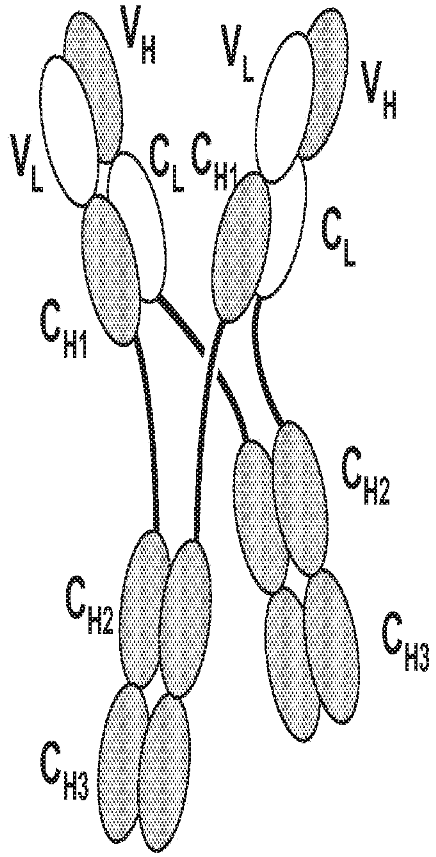

Specification includes a Sequence Listing.

(56) References Cited

U.S. PATENT DOCUMENTS

| | | | |
|---|---|---|---|
| 7,183,076 | B2 | 2/2007 | Arathoon et al. |
| 7,276,585 | B2 | 10/2007 | Lazar et al. |
| 7,317,091 | B2 | 1/2008 | Lazar et al. |
| 7,332,581 | B2 | 2/2008 | Presta |
| 7,355,008 | B2 | 4/2008 | Stavenhagen et al. |
| 7,371,826 | B2 | 5/2008 | Presta |
| 7,381,408 | B2 | 6/2008 | Mezo et al. |
| 7,504,256 | B1 | 3/2009 | Ogawa et al. |
| 7,521,541 | B2 | 4/2009 | Eigenbrot et al. |
| 7,642,228 | B2 | 1/2010 | Carter et al. |
| 7,651,688 | B2 | 1/2010 | Hanai et al. |
| 7,666,622 | B2 | 2/2010 | Sharma et al. |
| 7,695,936 | B2 | 4/2010 | Carter et al. |
| 7,919,257 | B2 | 4/2011 | Hoogenboom et al. |
| 7,942,042 | B2 | 5/2011 | Kawakita et al. |
| 7,951,917 | B1 | 5/2011 | Arathoon et al. |
| 8,188,231 | B2 | 5/2012 | Lazar et al. |
| 8,216,805 | B2 | 7/2012 | Carter et al. |
| 8,227,577 | B2 | 7/2012 | Klein et al. |
| 8,242,247 | B2 | 8/2012 | Klein et al. |
| 8,268,314 | B2 | 9/2012 | Baehner et al. |
| 8,304,713 | B2 | 11/2012 | Pradel |
| 8,309,300 | B2 | 11/2012 | Jununtula et al. |
| 8,313,913 | B2 | 11/2012 | Nakamura et al. |
| 8,642,745 | B2 | 2/2014 | Arathoon et al. |
| 8,765,412 | B2 | 7/2014 | Matsumoto |
| 8,796,424 | B2 | 8/2014 | Croasdale et al. |
| 8,945,552 | B2 | 2/2015 | Baehner et al. |
| 9,150,639 | B2 | 10/2015 | Yamasaki et al. |
| 9,241,994 | B2 | 1/2016 | Igawa |
| 9,308,259 | B2 | 4/2016 | Epshtein et al. |
| 9,605,084 | B2 | 3/2017 | Moore et al. |
| 9,890,204 | B2 | 2/2018 | Brinkman et al. |
| 9,982,036 | B2 | 5/2018 | Bossenmaier et al. |
| 10,138,293 | B2 | 11/2018 | Klein et al. |
| 10,323,099 | B2 | 6/2019 | Bruenker |
| 2002/0062010 | A1 | 5/2002 | Arathoon et al. |
| 2002/0155537 | A1 | 10/2002 | Carter et al. |
| 2002/0164328 | A1 | 11/2002 | Shinkawa et al. |
| 2003/0099974 | A1 | 5/2003 | Lillie et al. |
| 2003/0115614 | A1 | 6/2003 | Kanda et al. |
| 2003/0124129 | A1 | 7/2003 | Oliner |
| 2003/0157108 | A1 | 8/2003 | Presta |
| 2004/0018557 | A1 | 1/2004 | Qu et al. |
| 2004/0033561 | A1 | 2/2004 | O'Keefe et al. |
| 2004/0038339 | A1 | 2/2004 | Kufer et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2004/0214988 | A1 | 10/2004 | Tirrell et al. |
| 2004/0220388 | A1 | 11/2004 | Mertens et al. |
| 2004/0259075 | A1 | 12/2004 | Dimitrov et al. |
| 2004/0259150 | A1 | 12/2004 | Nakamura et al. |
| 2005/0014934 | A1 | 1/2005 | Hinton et al. |
| 2005/0031613 | A1 | 2/2005 | Nakamura et al. |
| 2005/0054048 | A1 | 3/2005 | Grasso et al. |
| 2005/0064509 | A1 | 3/2005 | Bradbury et al. |
| 2005/0079170 | A1 | 4/2005 | Le Gall et al. |
| 2005/0123476 | A1 | 6/2005 | Bugge et al. |
| 2005/0123546 | A1 | 6/2005 | Umana et al. |
| 2005/0152894 | A1 | 7/2005 | Krummen et al. |
| 2005/0163782 | A1 | 7/2005 | Glaser et al. |
| 2005/0249722 | A1 | 11/2005 | Beliard et al. |
| 2005/0260186 | A1 | 11/2005 | Bookbinder et al. |
| 2006/0063921 | A1 | 3/2006 | Moulder et al. |
| 2006/0104968 | A1 | 5/2006 | Bookbinder et al. |
| 2006/0122370 | A1 | 6/2006 | Oliner et al. |
| 2006/0134709 | A1 | 6/2006 | Stavenhagen et al. |
| 2006/0160184 | A1 * | 7/2006 | Mattheus Hoogenboom .............. C07K 16/005 435/69.1 |
| 2006/0280747 | A1 | 12/2006 | Fuh Gernaine et al. |
| 2007/0071675 | A1 | 3/2007 | Wu et al. |
| 2007/0071742 | A1 | 3/2007 | Fang et al. |
| 2007/0134759 | A1 | 6/2007 | Nishiya et al. |
| 2007/0141065 | A1 | 6/2007 | Fuh et al. |
| 2007/0166305 | A1 | 7/2007 | Hanai et al. |
| 2007/0269369 | A1 | 11/2007 | Gegg et al. |
| 2007/0274985 | A1 | 11/2007 | Dubel et al. |
| 2007/0274998 | A1 | 11/2007 | Utku |
| 2007/0287170 | A1 | 12/2007 | Davis et al. |
| 2008/0063641 | A1 | 3/2008 | Huang et al. |
| 2008/0187954 | A1 | 8/2008 | Kallmeier et al. |
| 2008/0234183 | A1 | 9/2008 | Hallbrink et al. |
| 2008/0241884 | A1 | 10/2008 | Shitara et al. |
| 2009/0023811 | A1 | 1/2009 | Biadatti et al. |
| 2009/0060910 | A1 | 3/2009 | Johnson |
| 2009/0155275 | A1 | 6/2009 | Wu et al. |
| 2009/0162359 | A1 * | 6/2009 | Klein ..................... C07K 16/22 424/136.1 |
| 2009/0162360 | A1 * | 6/2009 | Klein ..................... C07K 16/22 424/136.1 |
| 2009/0175851 | A1 | 7/2009 | Klein et al. |
| 2009/0194692 | A1 | 8/2009 | Kobaru |
| 2009/0203078 | A1 | 8/2009 | Ogawa et al. |
| 2009/0232811 | A1 | 9/2009 | Klein et al. |
| 2009/0304715 | A1 * | 12/2009 | Masuho ............. C07K 16/2887 424/173.1 |
| 2010/0015133 | A1 | 1/2010 | Igawa et al. |
| 2010/0081796 | A1 | 4/2010 | Brinkmann et al. |
| 2010/0111967 | A1 | 5/2010 | Baehner et al. |
| 2010/0254989 | A1 | 10/2010 | Bossenmaier et al. |
| 2010/0256338 | A1 | 10/2010 | Brinkmann et al. |
| 2010/0256339 | A1 | 10/2010 | Bossenmaier |
| 2010/0256340 | A1 | 10/2010 | Brinkmann et al. |
| 2010/0286374 | A1 | 11/2010 | Kannan et al. |
| 2010/0316645 | A1 | 12/2010 | Imhof-Jung et al. |
| 2010/0322934 | A1 | 12/2010 | Imhof-Jung et al. |
| 2010/0322935 | A1 | 12/2010 | Croasdale et al. |
| 2011/0054151 | A1 | 3/2011 | Lazar et al. |
| 2012/0149879 | A1 | 6/2012 | Brinkmann et al. |
| 2012/0164726 | A1 | 6/2012 | Klein et al. |
| 2012/0177637 | A1 | 7/2012 | Hoogenboom et al. |
| 2012/0184718 | A1 | 7/2012 | Bruenker et al. |
| 2012/0225071 | A1 | 9/2012 | Klein et al. |
| 2012/0237506 | A1 | 9/2012 | Bossenmaier et al. |
| 2012/0237507 | A1 | 9/2012 | Bossenmaier et al. |
| 2013/0022601 | A1 | 1/2013 | Brinkmann et al. |
| 2013/0045492 | A1 | 2/2013 | Babb et al. |
| 2013/0058936 | A1 | 3/2013 | Bruenker et al. |
| 2013/0058937 | A1 | 3/2013 | Auer et al. |
| 2013/0060011 | A1 | 3/2013 | Bruenker et al. |
| 2013/0078249 | A1 | 3/2013 | Ast et al. |
| 2013/0156772 | A1 | 6/2013 | Bossenmaier et al. |
| 2013/0266568 | A1 | 10/2013 | Brinkmann et al. |
| 2013/0267686 | A1 | 10/2013 | Brinkmann et al. |
| 2013/0273054 | A1 | 10/2013 | Bossenmaier et al. |
| 2014/0112914 | A1 | 4/2014 | Nezu et al. |
| 2014/0154254 | A1 | 6/2014 | Kannan et al. |
| 2014/0199294 | A1 | 7/2014 | Mimoto et al. |
| 2014/0249296 | A1 | 9/2014 | Ploegh |
| 2014/0294810 | A1 | 10/2014 | Lowman et al. |
| 2014/0322756 | A1 | 10/2014 | Arathoon et al. |
| 2014/0370019 | A1 | 12/2014 | Bruenker et al. |
| 2014/0370020 | A1 | 12/2014 | Kuramochi et al. |
| 2015/0232541 | A1 | 8/2015 | Fenn |
| 2015/0232560 | A1 | 8/2015 | Heindl et al. |
| 2015/0274845 | A1 | 10/2015 | Bruenker et al. |
| 2015/0291704 | A1 | 10/2015 | Beck |
| 2015/0315296 | A1 | 11/2015 | Schaefer et al. |
| 2015/0344570 | A1 | 12/2015 | Igawa et al. |
| 2016/0039937 | A1 | 2/2016 | Yamasaki et al. |
| 2016/0075785 | A1 | 3/2016 | Ast et al. |
| 2016/0130347 | A1 | 5/2016 | Bruenker et al. |
| 2016/0168259 | A1 | 6/2016 | Igawa |
| 2016/0208019 | A1 | 7/2016 | Bacac et al. |
| 2016/0222132 | A1 | 8/2016 | Keyt et al. |
| 2016/0238600 | A1 | 8/2016 | Hoogenboom et al. |
| 2016/0319036 | A1 | 11/2016 | Bruenker |
| 2017/0029529 | A1 | 2/2017 | Croasdale et al. |
| 2017/0037121 | A1 | 2/2017 | Schlothauer |
| 2017/0037153 | A1 | 2/2017 | Skolaut et al. |
| 2017/0044246 | A1 | 2/2017 | Schlothauer |

(56) References Cited

U.S. PATENT DOCUMENTS

| | | | |
|---|---|---|---|
| 2017/0096485 | A1 | 4/2017 | Bacac et al. |
| 2017/0096495 | A1 | 4/2017 | Bacac et al. |
| 2017/0114135 | A1 | 4/2017 | Codarri-Deak et al. |
| 2017/0114141 | A1 | 4/2017 | Amann et al. |
| 2017/0114146 | A1 | 4/2017 | Klein et al. |
| 2017/0129962 | A1 | 5/2017 | Regula et al. |
| 2017/0145116 | A1 | 5/2017 | Regula et al. |
| 2017/0247467 | A1 | 8/2017 | Amann et al. |
| 2017/0253670 | A1 | 9/2017 | Klein et al. |
| 2017/0306018 | A1 | 10/2017 | Vu et al. |
| 2017/0306036 | A1 | 10/2017 | Vu et al. |
| 2017/0349669 | A1 | 12/2017 | Sabine et al. |
| 2018/0037633 | A1 | 2/2018 | Bossenmaier et al. |
| 2019/0153071 | A1 | 5/2019 | Klein |

FOREIGN PATENT DOCUMENTS

| | | | |
|---|---|---|---|
| CN | 1176659 | A | 3/1998 |
| CN | 1232039 | A | 10/1999 |
| CN | 1603345 | A | 4/2005 |
| CN | 101065151 | A | 10/2007 |
| CN | 101205255 | A | 6/2008 |
| CN | 101218251 | A | 7/2008 |
| CN | 101355966 | A | 1/2009 |
| EP | 0 307 434 | B1 | 3/1989 |
| EP | 0 307 434 | B2 | 3/1989 |
| EP | 0 637 593 | A1 | 2/1995 |
| EP | 1 331 266 | A1 | 7/2003 |
| EP | 1 870 458 | A1 | 12/2007 |
| EP | 1 870 459 | A1 | 12/2007 |
| EP | 1 925 319 | A1 | 5/2008 |
| EP | 2 050 764 | A1 | 4/2009 |
| EP | 2 443 154 | B1 | 4/2012 |
| EP | 2 554 669 | A1 | 2/2013 |
| EP | 2 647 707 | A1 | 10/2013 |
| EP | 2 728 002 | A1 | 5/2014 |
| EP | 2 787 078 | A1 | 10/2014 |
| EP | 2 940 135 | A1 | 11/2015 |
| JP | 2008-531049 | A | 8/2008 |
| JP | 2011-506510 | A | 3/2011 |
| JP | 2012-525149 | A | 10/2012 |
| JP | 2013-539461 | A | 10/2013 |
| JP | 2015-502373 | A | 1/2015 |
| RU | 2005/124281 | A | 1/2006 |
| RU | 2295537 | C2 | 3/2007 |
| WO | WO-1993/01161 | A1 | 1/1993 |
| WO | WO-1993/06217 | A1 | 4/1993 |
| WO | WO-1993/10819 | A1 | 6/1993 |
| WO | WO-1993/16185 | A2 | 8/1993 |
| WO | WO-1993/16185 | A3 | 8/1993 |
| WO | WO-1994/09131 | A1 | 4/1994 |
| WO | WO-1994/10202 | A1 | 5/1994 |
| WO | WO-1994/29350 | A2 | 12/1994 |
| WO | WO-1994/29350 | A3 | 12/1994 |
| WO | WO-1994/29351 | A2 | 12/1994 |
| WO | WO-1994/29351 | A3 | 12/1994 |
| WO | WO-1995/09917 | A1 | 4/1995 |
| WO | WO-1996/27011 | A1 | 9/1996 |
| WO | WO-1996/27612 | A1 | 9/1996 |
| WO | WO-1997/01580 | A1 | 1/1997 |
| WO | WO-1997/014719 | A1 | 4/1997 |
| WO | WO-1997/028267 | A1 | 8/1997 |
| WO | WO-1997/028267 | C1 | 8/1997 |
| WO | WO-1997/30087 | A1 | 8/1997 |
| WO | WO-1998/10431 | A1 | 3/1998 |
| WO | WO-1998/10431 | C1 | 3/1998 |
| WO | WO-1998/45331 | A2 | 10/1998 |
| WO | WO-1998/45331 | A3 | 10/1998 |
| WO | WO-1998/45332 | A2 | 10/1998 |
| WO | WO-1998/45332 | A3 | 10/1998 |
| WO | WO-1998/48032 | A2 | 10/1998 |
| WO | WO-1998/48032 | A3 | 10/1998 |
| WO | WO-1998/50431 | A2 | 11/1998 |
| WO | WO-1998/50431 | A3 | 11/1998 |
| WO | WO-1998/58964 | A1 | 12/1998 |
| WO | WO-1999/22764 | A1 | 5/1999 |
| WO | WO-1999/37791 | A1 | 7/1999 |
| WO | WO-1999/51642 | A1 | 10/1999 |
| WO | WO-1999/54342 | A1 | 10/1999 |
| WO | WO-1999/66951 | A2 | 12/1999 |
| WO | WO-1999/66951 | A3 | 12/1999 |
| WO | WO-1999/66951 | C1 | 12/1999 |
| WO | WO-2000/05265 | A2 | 2/2000 |
| WO | WO-2000/05265 | A3 | 2/2000 |
| WO | WO-2000/35956 | A1 | 6/2000 |
| WO | WO-2000/61739 | A1 | 10/2000 |
| WO | WO-2001/29246 | A1 | 4/2001 |
| WO | WO-2001/77342 | A1 | 10/2001 |
| WO | WO-2001/85795 | A1 | 11/2001 |
| WO | WO-2001/90192 | A2 | 11/2001 |
| WO | WO-2001/90192 | A3 | 11/2001 |
| WO | WO-2002/02781 | A1 | 1/2002 |
| WO | WO-2002/31140 | A1 | 4/2002 |
| WO | WO-2002/33073 | A1 | 4/2002 |
| WO | WO-2002/096948 | A2 | 12/2002 |
| WO | WO-2002/096948 | A3 | 12/2002 |
| WO | WO-2002/096948 | A9 | 12/2002 |
| WO | WO-2003/011878 | A2 | 2/2003 |
| WO | WO-2003/011878 | A3 | 2/2003 |
| WO | WO-2003/030833 | A2 | 4/2003 |
| WO | WO-2003/030833 | A3 | 4/2003 |
| WO | WO-2003/035835 | A2 | 5/2003 |
| WO | WO-2003/035835 | A3 | 5/2003 |
| WO | WO-2003/055993 | A1 | 7/2003 |
| WO | WO-2003/057134 | A2 | 7/2003 |
| WO | WO-2003/057134 | A3 | 7/2003 |
| WO | WO-2003/073238 | A2 | 9/2003 |
| WO | WO-2003/073238 | A3 | 9/2003 |
| WO | WO-2003/084570 | A1 | 10/2003 |
| WO | WO-2003/085107 | A1 | 10/2003 |
| WO | WO-2003/085119 | A1 | 10/2003 |
| WO | WO-2003/097105 | A1 | 11/2003 |
| WO | WO-2003/106501 | A1 | 12/2003 |
| WO | WO-2004/003019 | A2 | 1/2004 |
| WO | WO-2004/003019 | A3 | 1/2004 |
| WO | WO-2004/032961 | A1 | 4/2004 |
| WO | WO-2004/056312 | A2 | 7/2004 |
| WO | WO-2004/056312 | A3 | 7/2004 |
| WO | WO-2004/058298 | A1 | 7/2004 |
| WO | WO-2004/065540 | A2 | 8/2004 |
| WO | WO-2004/065540 | A3 | 8/2004 |
| WO | WO-2004/072117 | A2 | 8/2004 |
| WO | WO-2004/072117 | A3 | 8/2004 |
| WO | WO-2004/106375 | A1 | 12/2004 |
| WO | WO-2005/000900 | A1 | 1/2005 |
| WO | WO-2005/001025 | A2 | 1/2005 |
| WO | WO-2005/001025 | A3 | 1/2005 |
| WO | WO-2005/004809 | A2 | 1/2005 |
| WO | WO-2005/004809 | A3 | 1/2005 |
| WO | WO-2005/005635 | A2 | 1/2005 |
| WO | WO-2005/005635 | A3 | 1/2005 |
| WO | WO-2005/011735 | A1 | 2/2005 |
| WO | WO-2005/018572 | A2 | 3/2005 |
| WO | WO-2005/018572 | A3 | 3/2005 |
| WO | WO-2005/027966 | A2 | 3/2005 |
| WO | WO-2005/027966 | A3 | 3/2005 |
| WO | WO-2005/033778 | A2 | 4/2005 |
| WO | WO-2005/033778 | A3 | 4/2005 |
| WO | WO-2005/035586 | A1 | 4/2005 |
| WO | WO-2005/035727 | A2 | 4/2005 |
| WO | WO-2005/035727 | A3 | 4/2005 |
| WO | WO-2005/035778 | A1 | 4/2005 |
| WO | WO-2005/044853 | A2 | 5/2005 |
| WO | WO-2005/044853 | A3 | 5/2005 |
| WO | WO-2005/044859 | A2 | 5/2005 |
| WO | WO-2005/044859 | A3 | 5/2005 |
| WO | WO-2005/051422 | A1 | 6/2005 |
| WO | WO-2005/051976 | A2 | 6/2005 |
| WO | WO-2005/051976 | A3 | 6/2005 |
| WO | WO-2005/053742 | A1 | 6/2005 |
| WO | WO-2005/063816 | A2 | 7/2005 |
| WO | WO-2005/063816 | A3 | 7/2005 |
| WO | WO-2005/074524 | A2 | 8/2005 |
| WO | WO-2005/074524 | A3 | 8/2005 |

(56) References Cited

FOREIGN PATENT DOCUMENTS

WO WO-2005/092925 A2 10/2005
WO WO-2005/092925 A3 10/2005
WO WO-2005/100402 A1 10/2005
WO WO-2006/020258 A2 2/2006
WO WO-2006/020258 A3 2/2006
WO WO-2006/029879 A2 3/2006
WO WO-2006/029879 A3 3/2006
WO WO-2006/031370 A2 3/2006
WO WO-2006/031370 A3 3/2006
WO WO-2006/034488 A2 3/2006
WO WO-2006/034488 A3 3/2006
WO WO-2006/044908 A2 4/2006
WO WO-2006/044908 A3 4/2006
WO WO-2006/045049 A1 4/2006
WO WO-2006/068953 A2 6/2006
WO WO-2006/068953 A3 6/2006
WO WO-2006/082515 A2 8/2006
WO WO-2006/082515 A3 8/2006
WO WO-2006/091209 A2 8/2006
WO WO-2006/091209 A3 8/2006
WO WO-2006/093794 A1 9/2006
WO WO-2006/103100 A2 10/2006
WO WO-2006/103100 A3 10/2006
WO WO-2006/106905 A1 10/2006
WO WO-2006/113665 A2 10/2006
WO WO-2006/113665 A3 10/2006
WO WO-2006/114700 A2 11/2006
WO WO-2006/114700 A3 11/2006
WO WO-2006/116260 A2 11/2006
WO WO-2006/116260 A3 11/2006
WO WO-2006/132352 A1 12/2006
WO WO-2007/024715 A2 3/2007
WO WO-2007/024715 A3 3/2007
WO WO-2007/031875 A2 3/2007
WO WO-2007/031875 A3 3/2007
WO WO-2007/044323 A2 4/2007
WO WO-2007/044323 A3 4/2007
WO WO-2007/044887 A2 4/2007
WO WO-2007/044887 A3 4/2007
WO WO-2007/048037 A2 4/2007
WO WO-2007/048037 A3 4/2007
WO WO-2007/068895 A1 6/2007
WO WO-2007/084181 A2 7/2007
WO WO-2007/084181 A3 7/2007
WO WO-2007/085837 A1 8/2007
WO WO-2007/089445 A2 8/2007
WO WO-2007/089445 A3 8/2007
WO WO-2007/095338 A2 8/2007
WO WO-2007/095338 A3 8/2007
WO WO-2007/108013 A2 9/2007
WO WO-2007/108013 A3 9/2007
WO WO-2007/109254 A2 9/2007
WO WO-2007/110205 A2 10/2007
WO WO-2007/110205 A3 10/2007
WO WO-2007/146959 A2 12/2007
WO WO-2007/146959 A3 12/2007
WO WO-2007/147901 A1 12/2007
WO WO-2007/149010 A1 12/2007
WO WO-2008/005828 A2 1/2008
WO WO-2008/005828 A3 1/2008
WO WO-2008/017963 A2 2/2008
WO WO-2008/017963 A3 2/2008
WO WO-2008/022349 A2 2/2008
WO WO-2008/022349 A3 3/2008
WO WO-2008/027236 A2 3/2008
WO WO-2008/027236 A3 3/2008
WO WO-2008/077077 A2 6/2008
WO WO-2008/077077 A3 6/2008
WO WO-2008/077546 A1 7/2008
WO WO-2008/100624 A2 8/2008
WO WO-2008/100624 A3 8/2008
WO WO-2008/132568 A2 11/2008
WO WO-2008/132568 A3 11/2008
WO WO-2009/018386 A1 2/2009
WO WO-2009/021745 A1 2/2009
WO WO-2009/021754 A2 2/2009
WO WO-2009/021754 A3 2/2009
WO WO-2009/023843 A1 2/2009
WO WO-2009/032782 A2 3/2009
WO WO-2009/032782 A3 3/2009
WO WO-2009/080251 A1 7/2009
WO WO-2009/080252 A1 7/2009
WO WO-2009/080253 A1 7/2009
WO WO-2009/080254 A1 7/2009
WO WO-2009/089004 A1 7/2009
WO WO-2009/126944 A1 10/2009
WO WO2010006060 A2 1/2010
WO WO-2010/034441 A1 4/2010
WO WO-2010/040508 A1 4/2010
WO WO-2010/040508 A8 4/2010
WO WO-2010/040508 A9 4/2010
WO WO-2010/045193 A1 4/2010
WO WO-2010/065882 A1 6/2010
WO WO2010006060 A3 6/2010
WO WO-2010/084197 A1 7/2010
WO WO-2010/087994 A2 8/2010
WO WO-2010/087994 A3 8/2010
WO WO-2010/108127 A1 9/2010
WO WO-2010/112193 A1 10/2010
WO WO-2010/112194 A1 10/2010
WO WO-2010/115552 A1 10/2010
WO WO-2010/115589 A1 10/2010
WO WO-2010/115589 A8 10/2010
WO WO-2010/129304 A2 11/2010
WO WO-2010/129304 A3 11/2010
WO WO-2010/136172 A1 12/2010
WO WO-2010/145792 A1 12/2010
WO WO-2010/145793 A1 12/2010
WO WO-2011/003557 A1 1/2011
WO WO-2011/028952 A1 3/2011
WO WO-2011/034605 A2 3/2011
WO WO-2011/034605 A3 3/2011
WO WO-2011/090754 A1 7/2011
WO WO-2011/090762 A1 7/2011
WO WO-2011/097603 A1 8/2011
WO WO-2011/118739 A1 9/2011
WO WO-2011/143545 A1 11/2011
WO WO-2012/023053 A2 2/2012
WO WO-2012/023053 A3 2/2012
WO WO-2012/025525 A1 3/2012
WO WO-2012/025530 A1 3/2012
WO WO2012045671 A1 4/2012
WO WO-2012/058768 A1 5/2012
WO WO-2012/073985 A1 6/2012
WO WO-2012/075037 A1 6/2012
WO WO-2012/116927 A1 9/2012
WO WO-2012/131555 A2 10/2012
WO WO-2012/131555 A3 10/2012
WO WO-2012/143379 A1 10/2012
WO WO-2012/148873 A2 11/2012
WO WO-2012/148873 A3 11/2012
WO WO-2013/002362 A1 1/2013
WO WO-2013/003555 A1 1/2013
WO WO-2013/012733 A1 1/2013
WO WO-2013/026832 A1 2/2013
WO WO-2013/026833 A1 2/2013
WO WO-2013/026835 A1 2/2013
WO WO-2013/065708 A1 5/2013
WO WO-2013/092001 A1 6/2013
WO WO-2013/092716 A1 6/2013
WO WO-2013/096291 A2 6/2013
WO WO-2013/096291 A3 6/2013
WO WO-2013/150043 A1 10/2013
WO WO-2013/157953 A1 10/2013
WO WO-2013/157954 A1 10/2013
WO WO-2013/174873 A1 11/2013
WO WO-2014/012085 A2 1/2014
WO WO-2014/012085 A3 1/2014
WO WO-2014/049003 A1 4/2014
WO WO-2014/081955 A1 5/2014
WO WO-20141082179 A1 6/2014
WO WO-2014/104165 A1 7/2014
WO WO-2014/144357 A1 9/2014
WO WO-2015/101588 A1 7/2015

(56) References Cited

FOREIGN PATENT DOCUMENTS

WO WO-2016/016299 A1 2/2016
WO WO-2016/055432 A2 4/2016
WO WO-2016/055432 A3 4/2016
WO WO-2016/087416 A1 6/2016
WO WO-2017/055385 A1 4/2017
WO WO-2017/055392 A1 4/2017
WO WO-2017/055393 A1 4/2017

OTHER PUBLICATIONS

Davis (Protein Engineering, Design & Selection, vol. 23, No. 4, p. 195-202, 2010) (Year: 2010).*
Krugman (The Journal of Immunology, vol. 159, p. 244-249, 1997) (Year: 1997).*
Tao (J. Exp. Med., vol. 173, p. 1025-1028, 1991) (Year: 1991).*
Greenwood (Eur. J. Immunology, vol. 23, p. 1098-1104, 1993) (Year: 1993).*
Pleas (The Journal of Biology Chemistry, vol. 274, No. 33, p. 23508-23514, 1999) (Year: 1999).*
Agata et al. "Expression of the PD-1 Antigen on the Surface of Stimulated Mouse T and B Lymphoctes," *Int. Immunology* 8(5):765-772, (1996).
Aggarwal et al.. "Fibroblast Activation Protein Peptide Substrates Identified from Human Collagen I Derived Gelatin Cleavage Sites," *Biochemistry* 47(3):1076-1086, (Jan. 22, 2008).
Alt et al. "Novel Tetravalent and Bispecific IgG-Like Antibody Molecules Combining Single-chain Diabodies With the Immunoglobulin γ1 Fc or CH3 Region," *FEBS Lett.* 454(1-2):90-94, (Jul. 2, 1999).
Anonymous. "Production in Yeasts of Stable Antibody Fragments," *Expert Opinion on Therapeutic Patents* 7(2):179-183, (1997).
Anthony, R.M. et al. "A Recombinant IgG Fc That Recapitulates the Antiinflammatory Activity of IVIG," *Science,* 320(5874):373-376, (2008).
Armour, K.L. et al. "Recombinant human IgG molecules lacking Fcγ receptor I binding and monocyte triggering activities," *Eur. J. Immunol.* 29:2613-2624, (1999).
Atwell et al. "Stable Heterodimers From Remodeling the Domain Interface of a Homodimer Using a Phage Display Library," *J. Mol. Biol.* 270 (1):26-35 (1997).
Ausubel et al. Short Protocols in Molecular Biology, Greene Publishing and Wiley Interscience, New York, New York, (Table of Contents), (1987).
Avgeris et al. "Kallikrein-Related Peptidase Genes as Promising Biomarkers for Prognosis and Monitoring of Human Malignancies," *Biol. Chem* 391(5):505-511, (May 2010).
Bacac et al. "A Novel Carcinoembryonic Antigen T-Cell Bispecific Antibody (CEA TCB) for the Treatment of Solid Tumors," *Clin. Cancer Res.* 22(13):3286-3297, (2016, e-pub. Feb. 9, 2016).
Bao et al. "HER2-Mediated Upregulation of MMP-1 is Involved in Gastric Cancer Cell Invasion," *Arch Biochem Biophys* 499(1-2):49-55, (Jul. 2010).
Barnes et al. "Advances in Animal Cell Recombinant Protein Production: GS-NS0 Expression System," *Cytotechnology* 32 (2):109-23 (Feb. 2000).
Barnes et al. "Characterization of the Stability of Recombinant Protein Production in the GS-NS0 Expression System," *Biotechnol Bioeng.* 73(4):261-70 (May 2001).
Baserga et al. "The IGF-1 Receptor in Cancer Biology," *Int. J. Cancer* 107:873-877, (2003).
Beckman et al. "Antibody Constructs in Cancer Therapy. Protein Engineering Strategies to Improve Exposure in Solid Tumors," *Cancer* 109(2):170-179, (Jan. 15, 2007, e-pub. Dec. 11, 2006).
Bendig. "Humanization of Rodent Monoclonal Antibodies by CDR Grafting," *Methods: A companion to Methods in Enzymology* 8:83-93 (1995).
Berkman, R.A. et al. "Expression of the Vascular Permeability Factor/Vascular Endothelial Growth Factor Gene in Central Nervous System Neoplasms," *J. Clin. Invest.* 91:153-159, (Jan. 1993).
Bera et al. "A Bivalent Disulfide-Stabilized Fv With Improved Antigen Binding to erbB2," *J. Mol. Biol.* 281(3):475-483, (Aug. 21, 1998).
Bird et al. "Single-Chain Antigen-Binding Proteins," *Science* 242(4877):423-6, (Oct. 21, 1988).
Bird et al. "Single-Chain Antigen-Binding Proteins," *Science* 244(4903):409, *Erratum,* (Apr. 28, 1989).
Boado, R.J. et al. "Engineering and Expression of a Chimeric Transferrin Receptor Monoclonal Antibody for Blood-Brain Barrier Delivery in the Mouse," *Biotechnology and Bioengineering* 102(4):1251-1258, Mar. 1, 2009.
Boado et al. "IgG-Single Chain Fv Fusion Protein Therapeutic for Alzheimer's Disease: Expression in CHO Cells and Pharmacokinetics and Brain Delivery in the Rhesus Monkey," *Biotechnology and Bioengineering* 105(3):627-635, (Feb. 15, 2010).
Boado, R.J. et al. "Selective Targeting of a TNFR Decoy Receoptor Pharmaceutical to the Primate Brain as a Receptor-Specific IgG Fusion Protein," *J. of Biotechnology* 146(1-2):84-91, (Mar. 1, 2010).
Boado, R.J. et al. "Drug Targeting of Erythropoietin Across the Primate Blood-Brain Barrier With an IgG Molecular Trojan Horse," *J. Pharmacology and Experimental Therapeutics* 333(3):961-969, (Jun. 1, 2010).
Boerner et al. "Production of Antigen-Specific Human Monoclonal Antibodies From In Vitro-Primed Human Splenocytes," *J. Immunol.* 147(1):86-95, (Jul. 1991).
Borgström et al. "Complete Inhibition of Angiogenesis and Growth of Microtumors by Anti-Vascular Endothelial Growth Factor Neutralizing Antibody: Novel Concepts of Angiostatic Therapy from Intravital Videomicroscopy," *Cancer Research* 56:4032-4039, (1996).
Bostrom et al. "Variants of the Antibody Herceptin That Interact With HER2 and VEGF at the Antigen Binding Site," *Science* 323:1610-1614, (2009).
Briggs et al. "Cystatin E/M Suppresses Legumain Activity and Invasion of Human Melanoma," *BMC Cancer* 10(17):1-13, (Jan. 2010).
Brinkmann. "Disulfide-Stabilized Fv Fragments," Chapter 14 in 2 in Antibody Engineering, Kontermaan et al. eds. vol. 2, Springer-Verlag, Berlin Heidelberg, Germany, pp. 181-189, (Apr. 30, 2010).
Brinkmann et al. "A Recombinant Immunotoxin Containing a Disulfide-Stabilized Fv Fragment," *PNAS* 90(16):7538-7542, (1993).
Brocks et al. "A TNF Receptor Antagonistic scFv, Which is Not Secreted in Mammalian Cells, is Expressed as a Soluble Mono- and Bivalent scFv Derivative in Insect Cells," *Immunotechnology* 3:173-184, (1997).
Brorson et al. "Mutational Analysis of Avidity and Fine Specificity of Anti-Levan Antibodies," *J. Immunol.* 163:6694-6701 (1994).
Brown, L.F. et al. "Expression of Vascular Permeability Factor (Vascular Endothelial Growth Factor) and its Receptors in Breast Cancer," *Human Pathol.* 26(1):86-91, (Jan. 1995).
Brown, L.F. et al. "Expression of Vascular Permeability Factor (Vascular Endothelial Growth Factor) and its Receptors in Adenocarcinomas of the Gastrointestinal Tract," *Cancer Res.* 53:4727-4735, (Oct. 1, 1993).
Brüggemann et al. "Comparison of the Effector Functions of Human Immunoglobulins Using a Matched Set of Chimeric Antibodies," *J Exp Med.* 166(5):1351-61, (Nov 1987).
Brüggemann et al. "Designer Mice: The Production of Human Antibody Repertoires in Transgenic Animals," *Year in Immuno.* 7:33-40, (1993).
Brummell et al. "Probing the Combining Site of an Anti-Carbohydrate Antibody by Saturation-Mutagenesis: Role of the Heavy-Chain CDR3 Residues," *Biochemistry* 32(4):1180-1187 (1993).
Brunhouse et al. "Isotypes of IgG: Comparison of the Primary Structures of Three Pairs of Isotypes Which Differ in Their Ability to Activate Complement," *Mol Immunol.* 16(11): 907-917 (Nov. 1979).
Brünker et al. "RG7386, A Novel Tetravalent FAP-DR5 Antibody, Effectively Triggers FAP-Dependent, Avidity-Driven DR5 Hyperclustering and Tumor Cell Apoptosis," *Mol. Cancer Ther.* 15(5):946-957, (May 2016, e-pub. Apr. 1, 2016).
Budtschanow et al. "System of Humoral Immunity Antibodies (Theme 2)," Guidance Manual for General Immunology, *Twer*

(56) References Cited

OTHER PUBLICATIONS (2008) p. 3, English Translation, 3 pages, (5 pages both English Equivalent and Russian Reference).
Burgess et al. "Possible Dissociation of the Heparin-Binding and Mitogenic Activities of Heparin-Binding (Acidic Fibroblast Growth Factor-1 From Its Receptor-Binding Activities by Site-Directed Mutagenesis of a Single Lysine Residue," *Journal of Cell Biology* 111:2129-2138, (Nov. 1990).
Burks et al. "In vitro Scanning Saturation Mutagenesis of an Antibody Binding Pocket," *PNAS* 94(2):412-417 (1997).
Burton et al. "The C1q Receptor Site on Immunoglobulin G," *Nature* 288(5789):338-344, (Nov. 27, 1980).
Caron et al. "Engineered humanized dimeric forms of IgG are more effective antibodies," *J. Exp. Med.* 176(4):1191-1195, (Oct. 1, 1992).
Carro et al. "Serum insulin-like growth factor I regulates brain amyloid-β levels," *Nature Medicine* 8(12):1390-1397, (2002, e-pub. Nov. 4, 2002).
Carter et al. "Humanization of an Anti-P185$^{HER2}$ Antibody for Human Cancer Therapy," *Proc Natl Acad. Sci. USA.* 89(10): 4285-4289 (May 1992).
Carter. "Bispecific Human IgG by Design," *Immunol. Methods* 248:7-15, (2001).
Carter, P.J. "Potent Antibody Therapeutics by Design," *Nature Reviews Immunology* 6:343-357, (May 2006).
Casset et al. "A Peptide Mimetic of an Anti-CD4 Monoclonal," *Biochem and Biophys Res Comm.* 307:198-205, (2003).
Castoldi et al. "Molecular Characterization of Novel Trispecific ErbB-cMet-IGF1R Antibodies and Their Antigen-Binding Properties," *Prot. Engin. Des. Selection* 25:551-560, (2012).
Castoldi et al. "TetraMabs: Simultaneous Targeting of Four Oncogenic Receptor Tyrosine Kinases for Tumor Growth Inhibition in Heterogeneous Tumor Cell Populations," *Protein Engineering, Design & Selection* 29(10):467-475, (2016, e-pub Aug. 29, 2016).
Cėspedes et al. "Mouse Models in Oncogenesis and Cancer Therapy," *Clin. Transl. Oncol.* 8(5):318-329 (2006).
Chan, L.A. et al. "Variable Region Domain Exchange in Human IgGs Promotes Antibody Complex Formulation with Accompanying Structural Changes and Altered Effector Functions," *Molecular Immunology* 41(5):527-538. (2004).
Chames P. et al. "Bispecific antibodies for cancer therapy," *Current Opinion in Drug Discovery & Development,* 12(2):276-283, (2009).
Chan, A.C. et al. "Therapeutic Antibodies for Autoimmunity and Inflammation," *Nat. Rev. Immunol.* 10(5):301-316, (May 2010).
Charlton. "Expression and Isolation of Recombinant Antibody Fragments in *E. coli*" Chapter 14 *in Methods in Molecular Biology,* B.K.C. Lo, ed. Humana Press, Totowa, NJ, 248:245-254, (2003).
Chen et al. "Improved Variants of SrtA for Site-Specific Conjugation on Antibodies and Proteins With High Efficiency," *Scientific Reports* 6(31899):1-12, (Aug. 18, 2016).
Chernaia, "[Cathepsin L From Human Brain Tumor. Purification and Contents]." Ukr Biokhim Zh. 70(5):97-103, (Sep.-Oct. 1998). (English Translation of Abstract.) (Article in Russian).
Cheung, A.H. et al. "Endothelial Tie2/Tek Ligands Angiopoietin-1 (ANGPT1) and Angiopoietin-2 (ANGPT2): Regional Localization of the Human Genes to 8q22.3-q23 and 8p23," *Genomics* 48(3):389-391, (Mar. 15, 1998).
Chicheportiche et al. "TWEAK, a New Secreted Ligand in the Tumor Necrosis Factor Family That Weakly Induces Apoptosis," *J. Biol. Chem.* 272(51):32401-32410, (1997).
Chin, J.W. et al. "Addition of p-azido-L-Phenylalanine to the Genetic Code of *Escherichia coli,*" *J. Am. Chem. Soc.* 124(31):9026-9027, (2002).
Chin, J.W. et al. "In vivo Photocrosslinking With Unnatural Amino Acid Mutagenesis," *ChemBioChem,* 3(11):1135-1137, (2002).
Chin J.W. et al."Addition of a Photocrosslinking Amino Acid to the Genetic Code of *Escherichia coli,*" *Proc. Natl. Acad. Sci. U.S.A.* 99(17):11020-11024, (2002).
Chinai et al. "New Immunotherapies Targeting the PD-1 Pathway," *Trends in Pharmacological Sciences* 36(9):587-595, (Sep. 2015), 21 pages.
Chitnis et al. "The Type 1 Insulin-Like Growth Factor Receptor Pathway," *Clin. Cancer Res.* 14(20):6364-6370, (Oct. 16, 2008).
Chowdhury. "Engineering Hot Spots for Affinity Enhancement of Antibodies," Chapter 11 *in Methods in Molecular Biology,* Welschof, M. et al. ed. Humana Press, Totowa, NJ, 207:179-196, (2008).
Chung et al. "Development of a Novel Albumin-Binding Prodrug That Is Cleaved by Urokinase-Type-Plasminogen Activator (uPA)," *Bioorg Med Chem Lett.* 16(19):5157-5163 (Oct. 1, 2006).
Clancy, K.W. et al. "Sortase transpeptidases: insights into mechanism, substrate specificity, and inhibition," *Biopolymers,* 94(4):385-396,(2010).
Clynes et al. "Fc Receptors are Required in Passive and Active Immunity to Melanoma," *Proc. Natl. Acad. Sci. USA* 95:652-656, (1998).
Cohen et al. "Nonchromosomal Antibiotic Resistance in Bacteria: Genetic Transformation of *Escherichia coli* by R-factor DNA," *Proc. Natl. Acad. Sci. USA* 69(8):2110-2114 (Aug. 1972).
Cole et al. "The EBV-Hybridoma Technique and Its Application to Human Lung Cancer," *Monoclonal Antibodies and Cancer Therapy,* New York: Alan R. Liss, Inc. pp. 77-96 (1985).
Coleman. "Effects of Amino Acid Sequence Changes on Antibody-Antigen Interactions," *Research in Immunol.* 145(1):33-38, (1994).
Coloma and Morrison. "Design and Production of Novel Tetravalent Bispecific Antibodies," *Nature Biotechnology* 15(2):159-163 (Feb. 1997).
Connolly, D.T. et al. "Human Vascular Permeability Factor," *J. Biol. Chem.* 264(33):20017-20024, (Nov. 25, 1989).
Cordingley et al. "Substrate Requirements of Human Rhinovirus 3C Protease for Peptide Cleavage in vitro," *J. Biol. Chem.* 265(16):9062-9065, (1990).
Cortesio et al. (Mar. 10, 2008). "Calpain 2 and PTP1B function in a Novel Pathway With Src to Regulate Invadopodia Dynamics and Breast Cancer Cell Invasion," *J. Cell Biol.* 180(5):957-971.
Coxon et al. "Combined Treatment of Angiopoietin and VEGF Pathway Antagonists Enhances Antitumor Activity in Preclinical Models of Colon Carcinoma," *99th AACR Annual Meeting,* Abstract #1113, (Apr. 2008).
Cragg et al. "Complement-Mediated Lysis by Anti-CD20 mAb Correlates with Segregation Into Lipid Rafts," *Blood* 101(3):1045-1052, (Feb. 1, 2003.).
Cragg, et al. "Antibody Specificity Controls in Vivo Effector Mechanisms of Anti-CD20 Reagents," *Blood* 103(7):2738-2743, (Apr. 1, 2004).
Croasdale et al. "Development of Tetravalent IgG 1 Dual Targeting IGF-1 R-EGFR Antibodies With Potent Tumor Inhibition," *Archives of Biochemistry and Biophysics* 526:206-218, (2012, e-pub. Mar. 21, 2012).
Crawford et al. "Matrix Metalloproteinase-7 Is Expressed by Pancreatic Cancer Precursors and Regulates Acinar-To-Ductal Metaplasia in Exocrine Pancreas," *J. Clin. Invest.* 109(11):1437-1444, (Jun. 2002).
Cruse, J.M. et al. 2nd ed. CRC Press (2003) p. 37, 316-317.
Cudic et al. "Extracellular proteases as targets for drug development," *Curr. Protein Pept Sci* 10(4):297-307, (Aug. 2009).
Cuesta et al. "Multivalent Antibodies: When Design Surpasses Evolution," *Trends Biotech.* 28:355-362, (2010).
Cullen et al. "Granzymes in Cancer and Immunity," *Cell Death Differ* 17(4):616-623, (Apr. 2010).
Cunningham et al. "High-Resolution Epitope Mapping of hGH-Receptor Interactions by Alanine-Scanning Mutagenesis," *Science* 244:1081-1085, (Jun. 2, 1989).
Daëron. "Fe Receptor Biology," *Annu. Rev. Immunol.* 15:203-234, (1997).
Dall'Acqua, W. et al. "Contribution of Domain Interface Residues to the Stability of Antibody CH3 Domain Homodimers," Biochemistry, 37:9266-9273, (1998).
Davis et al. "SEEDbodies: Fusion Proteins Based on Strand-Exchange Engineered Domain (SEED) $C_H3$ Heterodimers in an Fc Analogue Platform for Asymmetric Binders or Immunofusions and

(56) References Cited

OTHER PUBLICATIONS

Bispecific Antibodies," *Protein Engineering Design & Selection* 23(4):195-202, (2010, e-pub. Feb. 4, 2010).
Davies et al. "Expression of GnTIII in a Recombinant Anti-CD20 CHO Production Cell Line: Expression of Antibodies With Altered Glycoforms Leads to an Increase in ADCC Through Higher Affinity for FcγRIII," *Biotechnol. Bioeng.* 74:288-294, (2001).
De Haard et al. "A Large Non-Immunized Human Fab Fragment Phage Library That Permits Rapid Isolation and Kinetic Analysis of High Affinity Antibodies," *The Journal of Biological Chemistry* 274(26):18218-18230, (Jun. 25, 1999).
De Haas et al. "Fcy Receptors of Phagocytes," *J. Lab. Clin. Med.* 126(4):330-341, (Oct. 1995).
Dennis. "Off by a Whisker," *Nature* 442:739-741, (2006).
Deyev. "Multivalency: The Hallmark of Antibodies Used for Optimization of Tumor Targeting by Design," *Bioessays* 30(9):904-918, (2008).
Dimmock, N.J. et al. "Valency of Antibody Binding to Virions and Its Determination by Surface Plasmon Resonance," *Rev. Med. Virol.* 14:123-135, (2004).
Donaldson et al. "Design and development of Masked Therapeutic Antibodies to Limit Off-Target Effects: Application to Anti-EGFR Antibodies," *Cancer Biology & Therapy* 8(22):2145-2150, (Nov. 15, 2009).
Dufner et al. "Harnessing Phage and Ribosome Display for Antibody Optimization," *Trends Biotechol.* 24(11):523-29 (2006).
Duncan et al. "The Binding Site for Clq on IgG," *Nature* 332:738-40, (Apr. 21, 1988).
Durocher et al. "High-Level and High-Throughput Recombinant Protein Production by Transient Transfection of Suspension-Growing Human 293-EBNA1 cells," *Nucleic Acids Research* 30(2e9):nine pages, (2002).
Dvorak, H. et al. "Vascular Permeability Factor/Vascular Endothelial Growth Factor, Microvascular Hyperpermeability, and Angiogenesis," *Am. J. Pathol.* 146(5):1029-1039, (May 1995).
Edelman et al. "The Covalent Structure of an Entire γG Immunoglobulin Molecule," *Proc. Natl. Acad. Sci. USA* 63:78-85, (1969).
Fiedler and Skerra. "Purification and Characterisation of His-Tagged Antibody Fragments," Chapter 17 *in Antibody Engineering,* Kontermann and Dubel (Eds.), Springer Lab Manuals, pp. 243-256, (2001).
Fenn et al. "Crystal Structure of an Anti-Ang2 CrossFab Demonstrates Complete Structural and Functional Integrity of the Variable Domain," *PLOS ONE* 8(4):e61953 (Apr. 1, 2013).
Ferrara, N. et al. "The Biology of Vascular Endothelial Growth Factor," *Endocr. Rev.* 18(1):4-25, (1997).
Fischer et al. "Bispecific Antibodies: Molecules That Enable Novel Therapeutic Strategies," *Pathobiology* 74:3-14, (2007).
Flatman et al. "Process Analytics for Purification of Monoclonal Antibodies," *J. Chromatogr. B* 848:79-87, (2007).
Friend, P.J. et al. "Phase I Study of an Engineered Aglycosylated Humanized CD3 Antibody in Renal Transplant Rejection," *Transplantation,* 68(11):1632-1637,(1999).
Fujimori et al. "A Modeling Analysis of Monoclonal Antibody Percolation Through Tumors: A Binding-Site Barrier," *J. Nuc. Med.* 31(7):1191-1198, (Jul. 1990).
Galamb et al. "Inflammation, Adenoma and cancer: Objective Classification of Colon Biopsy Specimens With Gene Expression Signature," *Dis Markers* 25(1):1-16, (2008).
Gazzano-Santoro et al. "A Non-radioactive Complement-Dependent Cytotoxicity Assay for Anti-CD20 Monoclonal Antibody," *J. Immunol. Methods* 202:163-171, (1997).
Geisse et al. "Eukaryotic Expression Systems: A Comparison," *Protein Expression and Purification* 8:271-282 (1996).
Gerngross. "Advances in the Production of Human Therapeutic Proteins in Yeasts and Filamentous Fungi," *Nat. Biotech.* 22(11):1409-1414, (Nov. 2004).
Gerspach et al. "Target-Selective Activation of a TNF Prodrug by Urokinase-Type Plasminogen Activator (uPA) Mediated Proteolytic Processing at the Cell Surface," *Cancer Immunol. Immunother* 55:1590-1600 (2006).
Gold et al. "A Novel Bispecific, Trivalent Antibody Construct for Targeting Pancreatic Carcinoma," *Cancer Res.* 68(12):4819-4826, (2008).
Goldenberg et al. "Bi-Specific Antibodies that Bind Specific Target Tissue and Targeted Conjugates," Derwent Information Ltd. 12 pages, (2012).
Graham et al. "A New Technique for the Assay of Infectivity of Human Adenovirus 5 DNA," *Virology* 52 (2):456-467, (1973).
Graham et al. "Characteristics of a Human Cell Line Transformed by DNA from Human Adenovirus Type 5," *J. Gen Virol.* 36:59-72, (1977).
Greenwood et al. "Structural Motifs Involved in Human IgG Antibody Effector Functions," *Eur. J. Immunology* 23(5)1 098-1104, (May 1993).
Grote et al. "Bispecific Antibody Derivatives Based on Full-Length IgG Formats," Chapter 16 in *Methods in Molecular Biology* 901:247-263, (2012).
Gunasekaran et al. "Enhancing Antibody Fc heterodimer Formation Through Electrostatic Steering Effects: Applications to Bispecific Molecules and Monovalent IgG," *The Journal of Biological Chemistry* 285(25):19637-19646, (Jun. 18, 2010).
Guyer et al. "Immunoglobulin Binding by Mouse Intestinal Epithelial Cell Receptors," *J. Immunol.* 117(2):587-593, (Aug. 1976).
Hatfield, K.J. et al. "Antiangiogenic therapy in Acute Myelogenous Leukemia: Targeting of Vascular Endothelial Growth Factor and Interleukin 8 as Possible Antileukemic Strategies," *Curr.. Cancer Drug Targets,* 5(4):229-248, (2005).
Hartog et al. "The Insulin-like Growth Factor 1 Receptor in Cancer: Old Focus, New Future," *European Journal of Cancer* Pergamon Press, Oxford, GB, 43(13):1895-1904, (Aug. 23, 2007).
Hellings et al. "Interleukin-17 Orchestrates the Granulocyte Influx Into Airways After Allergen Inhalation in a Mouse Model of Allergic Asthma" *Am. J. Respir. Cell Mol. Biol.* 28:42-50, (2003).
Hellstrom et al. "Antitumor Effects of L6, an IgG2a Antibody That Reacts with Most Human Carcinomas," *Proc. Natl. Acad. Sci. USA* 83:7059-7063, (Sep. 1986).
Hellstrom et al. "Strong Antitumor Activities of IgG3 Antibodies to a Human Melanoma-Associated Ganglioside," *Proc. Natl. Acad. Sci. USA* 82:1499-1502, (Mar. 1985).
Henry et al. "Clinical implications of Fibroblast Activation Protein in Patients With Colon Cancer," *Clin Cancer Res.* 13(6):1736-1741, (Mar. 15, 2007).
Herberman, "Immunodiagnosis of Cancer," in Fleisher (ed.), "The Clinical Biochemistry of Cancer," p. 347 (American Association of Clinical Chemists (1979).
Hezareh et al. "Effector Function Activities of a Panel of Mutants of a Broadly Neutralizing Antibody against Human Immunodeficiency Virus Type 1," *Journal of Virology* 75(24):12161-12168, (Dec. 2001).
Hollander. "Bispecific Antibodies for Cancer Therapy," *Immunotherapy* 1(2):211-222, (Mar. 2009).
Holliger et al. "Engineered Antibody Fragments and the Rise of Single Domains," *Nat Biotechnol.* 23(9):1126-1136, (Sep. 2005).
Hoogenboom and Winter. "By-Passing Immunisation. Human Antibodies From Synthetic Repertoires of Germline $V_H$ Gene Segments Rearranged in vitro," *J Mol Biol.* 227 (2):381-388, (Sep. 20, 1992).
Hoogenboom et al. "Overview of Antibody Phage-Display Technology and Its Applications," Chapter 1 *in Methods in Molecular Biology,* O'Brien et al. ed. Human Press, Totowa, Nj, 178:1-37, (2001).
Huber, R. et al. "Crystallographic Structure Studies of an IgG Molecule and an Fc Fragment," *Nature,* 264:415-420, (1976).
Hudson et al. "Engineered Antibodies," *Nat. Med.* 9:129-134, (2003).
Hust et al. "Single Chain Fab (scFab) Fragment," *BMC Biotechnology* 7(14):1-15, (Mar. 8, 2007).
Huston, J.S. et al. "Medical Applications of Single-Chain Antibodies," *Intern. Rev. Immunol.* 10(2-3):195-217, (1993).

(56) References Cited

OTHER PUBLICATIONS

Huston et al. "Protein Engineering of Antibody Binding Sites: Recovery of Specific Activity in an Anti-Digoxin Single-Chain Fv analogue Produced in *Escherichia coli," Proc. Natl. Acad. Sci. U.S.A.* 85(16):5879-5883, (Aug. 1988).
Ibragimova et al. "Stability of the β-Sheet of the WW Domain: A Molecular Dynamics Simulation Study," *Biophysical Journal* 77:2191-2198, (Oct. 1999).
Idusogie et al. "Mapping of the C1q binding Site on Rituxan, A Chimeric Antibody With a Human IgG1 Fc," *The Journal of Immunology* 164:4178-4184, (2000).
Ilangovan, U. et al. "Structure of sortase, the transpeptidase that anchors proteins to the cell wall of *Staphylococcus aureus," Proc. Natl. Acad. Sci. U.S.A.* 98(11):6056-6061, (2001).
Ishida et al. "Induced Expression of PD-1, A Novel Member of the immunoglobulin Gene Superfamily, Upon Programmed Cell Death," *EMBO J.* 11(11):3887-3895, (1992).
Jackman et al. "Development of a Two-part Strategy to Identify a Therapeutic Human Bispecific Antibody That Inhibits IgE Receptor Signaling," *The Journal of Biological Chemistry* 285(27):20850-20859, (Jul. 2, 2010).
Jakobovits et al. "Analysis of Homozygous Mutant Chimeric Mice: Deletion of the Immunoglobulin Heavy-Chain Joining Region Blocks B-cell Development and Antibody Production," *Proc. Natl. Acad. Sci. USA* 90(6) :2551-2555, (Mar. 15, 1993).
Jakobovits et al. "Germ-line Transmission and Expression of a Human-derived Yeast Artificial Chromosome," *Nature* 362:255-258, (Mar. 1993).
Jang et al. "The Structural Basis for DNA Binding by an Anti-DNA Autoantibody," *Mol. Immunol.* 35(18):1207-1217 (1998).
Jefferis et al. "IgG-Fc-Mediated Effector Functions: Molecular Definition of Interaction Sites for Effector Ligands and the Role of Glycosylation," *Immunol Rev.* 163:59-76, (1998).
Jendreyko et al. "Simultaneous, Phenotypic Knockout of VEGF-R2 and Tie-2 With an Intradiabody Enhances Antiangiogenic Effects In Vivo," Therapieoptimierung and Risikostratifizierung, Scripps Research Institute, 218:143-151, (2006).
Jia et al."A Novel Trifunctional IgG-like Bispecific Antibody to Inhibit HIV-1 Infection and Enhance Lysis of HIV by Targeting Activation of Complement," *Virology Journal* 7(142):1-4, (Jun. 29, 2010).
Jiang, X.R. et al. "Advances in the Assessment and Control of the Effector Functions of Therapeutic Antibodies," *Nat. Rev. Drug Discov.* 10(2):101-111, (2011).
Johnson et al. "Kabat Database and its applications: 30 years after the first variability plot," *Nucleic Acids Research* 28(1):214-218, (2000).
Johnson et al. "Construction of Single-Chain Fv Derivatives Monoclonal Antibodies and their Production in *Escherichia coli," Methods Enzymol.* 203:88-98, (1991).
Kabat et al. "Evolutionary and structural Influences on Light Chain Constant ($C_L$) Region of Human and Mouse Immunoglobulins," *Proc. Natl. Acad. Sci. USA* 72(7):2785-2788, (Jul. 1975).
Kabat et al. Sequences of Proteins of Immunological Interest (Table of Contents and Introduction), 5th edition, Bethesda, MD: Public Health Service, NIH, vol. 1, (1991).
Kabat et al. "Sequences of Proteins of Immunological Interest," National Institutes of Health, vol. 1, Fifth Edition, pp. 647-723, (1991).
Kam et al. "Carbon Nanotubes as Multifunctional Biological Transporters and Near-Infrared Agents for Selective Cancer Cell Destruction," *Proc. Natl. Acad. Sci. USA* 102(33):11600-11605, (Aug. 16, 2005).
Kanda et al. "Comparison of Cell Lines for Stable Production of Fucose-Negative Antibodies With Enhanced ADCC," *Biotechnol. Bioeng.* 94(4):680-688, (Jul. 5, 2006; e-published Apr. 11, 2006).
Karadag et al. "ADAM-9 (MDC-9/meltrin-γ), A Member of the a Disintegrin and Metalloproteinase Family, Regulates Myeloma-Cell-Induced Interleukin-6 Production in Osteoblasts by Direct Interaction With the αvβ5 Integrin," *Blood* 107(8):3271-3278, (Apr. 2006).
Kaufman. "Overview of Vector Design for Mammalian Gene Expression," *Molecular Biotechnology* 16:151-160, (2000).
Kazama et al. "Hepsin, a Putative Membrane-Associated Serine Protease, Activates Human Factor VII and Initiates a Pathway of Blood Coagulation on the Cell Surface Leading to Thrombin Formation," *JBC* 270:66-72, (1995).
Keck, P.J. et al."Vascular Permeability Factor, an Endothelial Cell Mitogen Related to PDGF," *Science* 246:1309-1312, (1989).
Kim et al. "Inhibition of Vascular Endothelial Growth Factor-Induced Angiogenesis Suppresses Tumour Growth In Vivo," *Nature* 362:841-844, (1993).
Kim et al. "Localization of the Site of the Murine IgG1 Molecule that is Involved in Binding to the Murine intestinal Fc Receptor," *Eur. J. Immunol.* 24:2429-2434, (1994).
Kim, I. et al. "Molecular Cloning and Characterization of a Novel Angiopoietin Family Protein, Angiopoietin-3," *FEBS Let.* 443:353-56, (1999).
Kim, I. et al. "Molecular Cloning, Expression, and Characterization of Angiopoietin-Related Protein. Angiopoietin-Related Protein Induces Endothelial Cell Sprouting," *J. Biol. Chem.* 274(37):26523-26528, (Sep. 1999).
Klein et al. "Progress in Overcoming the Chain Association Issue in Bispecific Heterodimeric IgG Antibodies" *mAbs* 4(6):653-663, (2012).
Klein et al. "The Use of CrossMAb Technology for the Generation of Bi- and Multispecific Antibodies," *MABS.* 8(6):1010-1020, (2016).
Kleinschmidt et al. "Design of a Modular Immunotoxin Connected by Polyionic Adapter Peptides," *J. Mol. Biol.* 327(2):445-452, (Mar. 21, 2003).
Kobayashi et al. "Similarities in the Biodistribution of Iodine-Labeled Anti-Tac Single-Chain Disulfide-Stabilized Fv Fragment and Anti-Tac Disulfide-Stabilized Fv Fragment," *Nuclear Medicine & Biology* 25:387-393, (1998).
Kobayshi et al. "Tryptophan H33 Plays an Important Role in Pyrimidine (6-4) Pyrimidone Photoproduct Binding by a High-Affinity Antibody," *Protein Engineering* 12(10):879-844 (1999).
Kodukula et al. "Biosynthesis of Phosphatidylinositol Glycan-Anchored Membrane Proteins. Design of a Simple Protein Substrate to Characterize the Enzyme That Cleaves the COOH-Terminal Signal Peptide," *The Journal of Biological Chemistry* 266(7):4464-4470 (Mar. 5, 1991).
Komiyama et al. "IL-17 Plays an Important Role in the Development of Experimental Autoimmune Encephalomyelitis," *J Immunol* 177:566-573, (2006).
Kotake et al. "IL-17 in Synovial Fluids From Patients With Rheumatoid Arthritis Is a Potent Stimulator of Osteoclastogenesis," *J. Clin. Invest.* 103:1345-1352, (1999).
Krugmann et al. "Structural Requirements for Assembly of Dimeric IgA Probed by Site-Directed Mutagenesis of J Chain and a Cysteine Residue of the α-chain CH2 Domain," *The Journal of Immunology* 159:244-249, (1997).
Kumar et al. "Molecular Cloning and Expression of the Fabs of Human Autoantibodies in *Escherichia coli," J. Biol. Chem.* 275(45):35129-35136, (Nov. 10, 2000).
Labrijn et al. "Species-Specific Determinants in the IgG CH3 Domain Enable Fab-Arm Exchange by Affecting the Noncovalent CH3—CH3 Interaction Strength," *The Journal of Immunology* 187:3238-3246, (2011, e-pub. Aug. 12, 2011).
Lamkanfi et al. "Inflammasomes: Guardians of Cytosolic Sanctity," *Immunol. Rev.* 227(1):95-105, (Jan. 2009).
Lazar et al. "Transforming growth factor α: Mutation of aspartic acid 47 and leucine 48 results in different biological activities," *Molecular and Cellular Biology* 8(3):1247-1252, (Mar. 1988).
Lee et al. "Using Substrate Specificity of Antiplasmin-Cleaving Enzyme for Fibroblast Activation Protein Inhibitor Design," *Biochemistry* 48(23):5149-5158, (Jun. 16, 2009).
Lee et al. "Generation and Characterization of a Novel Single-Gene-Encoded Single-Chain Immunoglobulin Molecule With Antigen Binding Activity and Effector Functions" *Mol Immunol.* 36(1):61-71, (1999).
Leeman et al. "The Structure, Regulation, and Function of Human Matrix Metalloproteinase-13," *Crit. Rev Biochem Mol. Biol.* 37(3):149-166, (2002).

(56) References Cited

OTHER PUBLICATIONS

Leitzgen et al. "Assembly of Immunoglobulin Light Chains as a Prerequisite for Secretion," *Journal of Biological Chemistry* 272(5):3117-3123, (Jan. 31, 1997).
Leung, D.W. et al."Vascular Endothelial Growth Factor is a Secreted Angiogenic Mitogen," *Science* 246:1306-1309, (Dec. 8, 1989).
Levary et al. "Protein-Protein fusion catalyzed by sortase A," *PLOS One* 6:e18342.1-e18342.6, (2011).
Lewis, M.L. et al. "Generation of Bispecific IgG Antibodies by Structure-Based Design on an Orthogonal Fab Interface," *Nature Biotechnology* 32(2):191-198, (Feb. 1, 2014).
Li et al. "Optimization of Humanized IgGs in Glycoengineered *Pichia pastoris,*" *Nat. Biotech.* 24(2):210-215, (Feb. 2006; e-published Jan. 22, 2006).
Lifely et al. "Glycosylation and Biological Activity of CAMPATH-1H Expressed in Different Cell Lines and Grown Under Different Culture Conditions," *Glycobiology* 5(8):813-822, (Dec. 1995).
Lin et al. "Structure-Function Relationships in Glucagon: Properties of Highly Purified des-his-, monoiodo-, and [Des-Asn$^{28}$, Thr$^{29}$](homoserine lactone$^{27}$)-glucagon," *Biochemistry USA* 14:1559-1563, (1975).
Liang et al. "Cross-species Vascular Endothelial Growth Factor (VEGF)-blocking Antibodies Completely Inhibit the Growth of Human Tumor Xenografts and Measure the Contribution of Stromal VEGF," *Journal of Biological Chemistry* 281(2):951-961, (2006).
Liotta et al. "Metastatic Potential Correlates With Enzymatic Degradation of Basement Membrane Collagen," *Nature* 284(5751) 67-68, (Mar. 6, 1980).
Liu et al. "Clinical and Imaging Diagnosis of Primary Hepatic Lymphoma," *J First Mil Med. Univ,* 25(10):1290-1292, three pages, (2005). (Translation of the Abstract Only.).
Lodish et al. "Post-Translational Modifications and Quality Control in the Rough ER," Chapter 17, Section 17.6 *in Molecular Cell Biology,* 4th edition, W.H. Freeman and Company, New York, pp. 707-712, (1999).
Lopez-Otin et al. "The Regulatory Crosstalk Between Kinases and Proteases in Cancer," *Nat. Rev. Cancer* 10(4):278-292, (Apr. 2010).
Love et al. "Recombinant Antibodies Possessing Novel Effector Functions," *Methods in Enzymology* 178:515-527, (1989).
Lu et al. "A Fully Human Recombinant IgG-Like Bispecific Antibody to Both the Epidermal growth Factor Receptor and the Insulin-Like Growth Factor Receptor for Enhanced Antitumor Activity," *The Journal of Biological Chemistry* 280(20):19665-19672, (May 20, 2005).
Lu et al. "ADAMTS1 and MMP1 Proteolytically Engage EGF-like Ligands in an Osteolytic Signaling Cascade for Bone Metastasis," *Genes Dev.* 23(16):1882-1894, (Aug. 2009).
Lukas et al. "Inhibition of C1-Mediated Immune Hemolysis by Monomeric and Dimeric Peptides from the Second Constant Domain of Human Immunoglobulin G," *The Journal of Immunolgy* 127(6):2555-2560, (Dec. 1981).
Lund et al. "Oligosaccharide-protein interactions in IgG can modulate recognition by Fcγ receptors," *FASEB Journal* 9:115-119, (1995).
Lynch et al. "TWEAK Induces Angiogenesis and Proliferation of Endothelial Cells," *J. Biol. Chem.* 274(13):8455-8459, (Mar. 26, 1999).
Madej, M.P. et al. "Engineering of an anti-epidermal growth factor receptor antibody to single chain format and labeling by sortase A-mediated protein ligation," *Biotechnology and Bioengineering* 109(6):1461-1470, (2012).
Maisonpierre, P.C. et al. "Angiopoietin-2, a Natural Antagonist for Tie2 that Disrupts in vivo Angiogenesis," *Science* 277:55-60, (Jul. 4, 1997).
Makrides. "Components of Vectors for Gene Transfer and Expression in Mammalian Cells," *Protein Expression and Purification* 17:183-202, (1999).
Mallender et al "Comparative Properties of the Single Chain Antibody and Fv Derivatives of mAb 4-4-20. Relationship Between Interdomain Interactions and the High Affinity for Fluorescein Ligand," *Journal of Biological Chemistry* 271(10):5338-5346, (Mar. 8, 1996).
Mamoune et al. "Calpain-2 as a Target for Limiting Prostate Cancer Invasion," *Cancer Res.* 63(15):4632-4640, (Aug. 2003).
Marks et al. "By-Passing Immunization: Human Antibodies From V-gene Libraries Displayed on Phage," *J Mol Biol.* 222(3):581-597, (Dec. 5, 1991).
Marsters et al. "Identification of a Ligand for the Death-Domain-Containing Receptor Apo3," *Curr. Biol.* 8(9):525-528, (1998).
Marvin et al. "Recombinant Approaches to IgG-like Bispecific Antibodies," *Acta Pharmacol. Sin.* 26:649-658, (2005).
Marvin et al. "Bispecific antibodies for Dual-Modality Cancer Therapy: Killing Two Signaling Cascades With One Stone," *Curr. Opin. Drug Discov. Devl.* 9:184-193, (2006).
Mather. "Establishment and Characterization of Two Distinct Mouse Testicular Epithelial Cell Lines," *Biol. Reprod.* 23:243-251, (1980).
Mather et al. "Culture of Testicular Cells in Hormone-Supplemented Serum-Free Medium," *Annals N.Y. Acad. Sci.* 383:44-68, (1982).
Matrisian. "Cancer Biology: Extracellular Proteinases in Malignancy," *Curr. Biol.* 9(20):R776-R778, (Oct. 1999).
Mattern, J. et al. "Association of Vascular Endothelial Growth Factor Expression With Intratumoral Microvessel Density and Tumour Cell Proliferation in Human Epidermoid Lung Carcinoma," *Brit. J. Cancer* 73:931-934, (1996).
Matusevicius et al. "Interleukin-17 mRNA Expression in Blood and CSF Mononuclear Cells is Augmented in Multiple Sclerosis," *Multiple Sclerosis* 5:101-104, (1999).
McLean, G.R. et al. "A Point Mutation in the CH3 Domain of Human IgG3 Inhibits Antibody Secretion Without Affecting Antigen Specificity," *Molecular Immunology,* 42:1111-1119, (2005).
Meissner et al. "Transient Gene Expression: Recombinant Protein Production with Suspension-Adapted HEK293-EBNA Cells," *Biotechnology and Bioengineering* 75:197-203, (2001).
Melnyk et al. "Vascular Endothelial Growth Factor Promotes Tumor Dissemination by a Mechanism Distinct from Its Effect on Primary Tumor Growth," *Cancer Research* 56:921-924, (1996).
Merchant et al. "An Efficient Route to Human Bispecific IgG," *Nature Biotechnology* 16:677-681, (1998).
Metz et al. "Bispecific Antibody Derivatives With Restricted Binding Functionalities that are Activated by Proteolytic Processing," *Prot. Eng. Des. Sel.* 25:571-580, (2012).
Metz, S. et al. "Bispecific Digoxigenin-Binding Antibodies for targeted Payload Delivery," *Proc. Natl. Acad. Sci. U.S.A.* 108 (20):8194-8199, (May 17, 2011).
Michaelson et al. "Anti-Tumor Activity of Stability-Engineered IgG-Like Bispecific Antibodies Targeting TRAIL-R2 and LTβR," *MAbs* 1(2):128-141, (Mar. 2009, e-pub. Mar. 11, 2009).
Milstein et al. "Hybrid Hybridomas and Their Use in Immunohistochemistry," *Nature* 305:537-540, (Oct. 6, 1983).
Miller et al. "Design, Construction, and In Vitro Analyses of Multivalent Antibodies," *J. Immunol.* 170:4854-4861, (2003).
Mimura et al. "Role of Oligosaccharide Residues of IgG1-Fc in FcγRIIb Binding," *The Journal of Biological Chemistry* 276(49): 45539-45547, (Dec. 7, 2001).
Minn et al. "Genes that Mediate Breast Cancer Metastasis to Lung," *Nature* 436(7050):518-524, (Jul. 2005).
Mirny, L. et al. "Protein Folding Theory: From Lattice to All-Atom Models," *Annu. Rev. Biophys. Biomol. Struct.* 30:361-96, (2001).
Mizukami, Y. et al. "Induction of Interleukin-8 Preserves the Angiogenic Response in HIF-1α-Deficient Colon Cancer Cells," *Nat. Med.* 11(9):992-997, (2005).
Möhlmann S. et al. "In vitro sortagging of an antibody fab fragment: overcoming unproductive reactions of sortase with water and lysine side chains," *Chembiochem: A European Journal of Chemical Biology,* 12(11):1774-1780, (2011).
Morgan et al. "The N-terminal End of the $C_H2$ Domain of Chimeric Human IgG1 anti-HLA-DR is Necessary for C1q, FcγRI and FcγRIII Binding," *Immunology* 86:319-324, (1995).
Morrison et al. "Chimeric Human Antibody Molecules: Mouse Antigen-Binding Domains with Human Constant Region Domains," *Proc. Natl. Acad. Sci. USA* 81(21) :6851-6855, (Nov. 1984).

(56) References Cited

OTHER PUBLICATIONS

Morrison et al. "Variable Region Domain Exchange Influences the Functional Properties of IgG," *Journal of Immunology, American Association of Immunologists* 160:2802-2808, (Jan. 1, 1998).
Morrison. "Two Heads are Better than One," *Nature Biotechnology* 25(11):1233-1234, (Nov. 2007).
Morrison. "Success in Specification," *Nature* 368:812-813, (Apr. 1994).
Müller et al. "Recombinant Bispecific Antibodies for Cellular Cancer Immunotherapy," *Current Opinion in Molecular Therapeutics* 9:319-326, (2007).
Müller et al. "Bispecific Antibodies," Chapter 2 in Handbook of Therapeutic Antibodies, Dübel, S. ed. Wiley-VCH Verlag GmbH & Company KGaA, Weinheim, pp. 345-378, (2007).
Müller et al. "The First Constant Domain ($C_H1$ and $C_L$) of an Antibody Used as Heterodimerization Domain for Bispecific Miniantibodies," *FEBS Letters* 422:259-264, (1998).
Mukhopadhyay et al. "Matrix Metalloproteinase-12 Is a Therapeutic Target for Asthma in Children and Young Adults," *J. Allergy Clin Immunol.* 126:70-76, (2010).
Myatt et al. "Pathogenic Potential of Human Monoclonal Immunoglobulin Light Chains: Relationship of in vitro Aggregation to in vivo Organ Deposition," *Proc. Natl. Acad. Sci. USA* 91:3034-3038, (Apr. 1994).
Nagaoka et al. "Single Amino Acid Substitution in the Mouse IgG1 Fc Region Induces Drastic Enhancement of the Affinity to Protein A," *Protein Engineering* 16(4):243-245, (2003).
Netzel-Arnett et al. "Sequence Specificities of Human Fibroblast and Neutrophil Collagenases," *J. Biol. Chem.* 266(11):6747-6755, (Apr. 15, 1991).
Netzel-Arnett et al. "Comparative Sequence Specificities of Human 72- and 92-kDa Gelatinases (type IV collagenases) and PUMP (matrilysin)," *Biochemistry* 32(25):6427-6432, (Jun. 29, 1993).
Neuberger et al. "A Hapten-Specific Chimaeric IgE Antibody With Human Physiological Effector Function," *Nature* 314:268-270, (Mar. 21, 1985).
Niwa et al. "IgG subclass-Independent Improvement of Antibody-Dependent Cellular Cytotoxicity by Fucose Removal From $Asn^{297}$-Linked Oligosaccharides," *J. Immunol. Methods* 306:151-160, (2005).
Norderhaug et al. "Versatile Vectors for Transient and Stable Expression of Recombinant Antibody Molecules in Mammalian Cells," *Journal of Immunological Methods* 204:77-87, (1997).
Noren, C.J. et al. "A General Method for Site-Specific Incorporation of Unnatural Amino Acids into Proteins," *Science* 244:182-188, (1989).
Novellino, L. et al. "A Listing of Human Tumor Antigens Recognized by T Cells: Mar. 2004 Update," *Cancer Immunol. Immunother,* 54(3):187-207, (2005).
Novotný, J. et al. "Structural invariants of antigen binding: Comparison of immunoglobulin $V_L$-$V_H$ and $V_L$-$V_L$ domain dimmers," *Proc. Natl. Acad. Sci. USA,* 82:4592-4596, (1985).
Ohno et al. "Antigen-Binding Specificities of Antibodies Are Primarily Determined by Seven Residues of $V_H$," *Proc. Natl. Acad. Sci. USA* 82(9):2945-2949, (May 1985).
Okazaki et al. "Fucose Depletion from Human IgG1 Oligosaccharide Enhances Binding Enthalpy and Association Rate Between IgG1 and FcγRIIIa," *J. Mol. Biol.* 336:1239-1249, (2004).
Oliner et al. "Suppression of Angiogenesis and Tumor Growth by Selective Inhibition of Angiopoietin-2," *Cancer Cell* 6:507-516, (2004).
Orcutt, et al. "A Modular IgG-scFv Bispecific Antibody Topology," *Protein Engineering, Design & Selection* 23(4):221-228, (Apr. 2010, e-pub. Dec. 17, 2009).
Orlandi et al. "Cloning Immunoglobulin Variable Domains for Expression by the Polymerase Chain Reaction," *Proc. Natl. Acad. Sci. USA* 86:3833-3837, (May 1989).
Pace et al. "How to Measure and Predict the Molar Absorption Coefficient of a Protein," *Protein Science* 4(11): 2411-2423, (Nov. 1995).
Pakula et al. "Genetic Analysis of Protein Stability and Function," *Annu. Rev. Genet.* 23:289-310, (1989).
Pan, Q. et al. "Blocking Neuropilin-1 Function Has an Additive Effect with nti-VEGF to Inhibit Tumor Growth," *Cancer Cell* 11 :53-67, (Jan. 2007).
Pardridge, W.M. "Drug Transport Across the Blood-Brain Barrier," *J. of Cerebral Blood Flow & Metabolism* 32(11):1959-1972, (Aug. 29, 2012).
Parmiani, G. et al. "Unique Human Tumor Antigens: Immunobiology and Use in Clinical Trials," *J. Immunol,* 178(4):1975-1979, (2007).
Paul. "Immunoglobulins: Structure and Function," in Fundamental Immunolgy, Jeske, D.D. et al.New York, New York, Raven Press, p. 131-165. (1 page translation of 7.9.1 Disculfide Bonds), (1984).
Paul. "Structure and Function of Immunoglobulins," Chapter 9 in *Fundamental Immunology,* Third Edition, Raven Press, New York, New York, pp. 292-295, (1993).
Petkova et al. "Enhanced Half-Life of Genetically Engineered Human IgG1 Antibodies in a Humanized FcRn Mouse Model: Potential Application in Humorally Mediated Autoimmune Disease," *Int'l. Immunol.* 18(12):1759-1769, (2006).
Pleass et al. "Identification of Residues in the CH2/CH3 Domain Interface of IgA Essential for Interaction With the Human fcα Receptor (Fcα R) CD89," *The Journal of Biology Chemistry* 274(33):23508-23514, (Aug. 13, 1999).
Pluckthun. "Antibodies from *Escherichia coli*" Chapter 11 *in The Pharmacology of Monoclonal Antibodies: Handbook of Pharmacology,* Rosenberg and Moore, eds. Berlin:Springer-Verlag, vol. 113, pp. 269-315, (1994).
Plückthun et al. "New Protein Engineering Approaches to Multivalent and Bispecific Antibody Fragments," *Immunotechnology* 3:83-105, (1997).
Popp M.W. et al. "Making and Breaking Peptide Bonds: Protein Engineering Using Sortase," Angewandte *Chemie,* 50(22):5024-5032, (2011).
PreScission Protease, GE Healthcare Catalogue No. 27/0843-01, located at http://www.gelifesciences.com/webapp/wcs/stores/servlet/productById/en/GELifeScience, last visited on Jul. 10, 2013, one page.
Presta, L.G. "Molecular Engineering and Design of Therapeutic Antibodies," *Current Opinion in Immunology* 20:460-470, (2008).
Radaev et al. "Recognition of IgG by Fcγ Receptor," *The Journal of Biological Chemistry* 276(19):16478-16483, (May 11, 2001).
Rajagopal et al. "A Form of Anti-Tac(Fv) Which is Both Single-chain and Disulfide Stabilized: Comparison with its single-chain and Disulfide-stabilized Homologs," *Protein Engineering* 10(12):1453-1459, (1997).
Raju. "Glycosylation Variations with Expression Systems and Their Impact on Biological Activity of Therapeutic Immunoglobulins," *BioProcess International* 1(4): 44-53, (Apr. 2003).
Ravetch et al. "Fc Receptors," *Annu. Rev. Immunol.* 9:457-92, (1991).
Rawlings. "A Large and Accurate Collection of Peptidase Cleavages in the MEROPS Database," *Database* (Oxford), pp. 1-14, (2009, e-pub. Nov. 2, 2009).
Reiter et al. "Stabilization of the Fv Fragments in Recombinant Immunotoxins by Disulfide Bonds Engineered into Conserved Framework Regions," *Biochemistry* 33:5451-5449, (1994).
Reiter et al. "Improved Binding and Antitumor Activity of a Recombinant Anti-ErbB2 Immunotoxin by Disulfide Stabilization of the Fv Fragment," *JBC* 269:18327-18331, (1994).
Reiter et al. "Engineering interchain Disulfide Bonds Into Conserved Framework Regions of Fv fragments: Improved Biochemical Characteristics of Recombinant Immunotoxins Containing Disulfide-Stabilized Fv," *Protein Eng.* 7(5):697-704, (May 1994).
Reiter et al. "Cytotoxic and antitumor Activity of a Recombinant Immunotoxin Composed of Disulfide-Stabilized Anti-Tac Fv Fragment and Truncated *Pseudomonas* Exotoxin," *International Journal of Cancer* 58:142-149, (1994).
Reiter et al. "Antitumor Activity and Pharmacokinetics in Mice of a Recombinant Immunotoxin Containing a Disulfide-Stabilized Fv Fragment," *Cancer Research* 54:2714-2718, (1994).

(56) References Cited

OTHER PUBLICATIONS

Reiter et al. "Antibody Engineering of Recombinant Fv immunotoxins for Improved Targeting of Cancer: Disulfide-Stabilized Fv Immunotoxins," *Clin. Cancer Res.* 2(2):245-252, (Feb. 1, 1996).
Reiter et al. "Disulfide Stabilization of Antibody Fv: Computer Predictions and Experimental Evaluation," *Protein Engineering* 8:1323-1331, (1995).
Reiter et al. "Construction of a Functional Disulfide-Stabilized TCR Fv Indicates That Antibody and TCR Fv Frameworks Are Very Similar in Structure," *Immunity* 2:281-287, (1995).
Reiter et al. "Engineering Antibody Fv Fragments for Cancer Detection and Therapy: Disulfide-Stabilized Fv Fragments," *Nature Biotechnology* 14:1239-1245, (1996).
Remington'S Pharmaceutical Sciences, Table of Contents, 2 pages, (1980).
Ren, Y. et al. "Macrophage Migration Inhibitory Factor Stimulates Angiogenic Factor Expression and Correlates With Differentiation and Lymph Node Status in Patients With Esophageal Squamous Cell Carcinoma," *Ann. Surg.* 242:55-63, (2005).
Reyes, A.E. et al. "Pharmacokinetics of a Novel One Armed Antibody to C-Met in Mice, Rats and Monkeys," Genentech, Inc. *Amer. Assn. Pharm. Sci.* 10:S1, (2008).
Ridgway et al. "'Knobs-into-holes' Engineering of antibody $C_H3$ domains for heavy chain heterodimerization," *Protein Engineering* 9(7):617-621, (1996).
Riechmann et al. "Reshaping Human Antibodies for Therapy," *Nature* 332:323-327, (Mar. 24, 1988).
Ripka et al. "Two Chinese Hamster Ovary Glycosylation Mutants Affected in the Conversion of GDP-Mannose to GDP-Fucose," *Arch. Biochem. Biophys.* 249(2):533-545, (Sep. 1986).
Roitt et al. "Immunology," English Translation by McElroy Translation Company, Moscow "Mir" (2000), p. 110-111, eight pages.
Roitt A. et al. "Multispecific Antibodies Comprising Full Length Antibodies and Single Chain Fab Fragments," *Immunology,* English Translation, Moscow:Mir, pp. 388-389, (2000).
Rose et al. "Quantitative Analysis of the Interaction Strength and Dynamics of Human IgG4 Half Molecules by Native Mass Spectrometry," *Structure* 19:1274-1282, (Sep. 7, 2011).
Rossi, E.A. et al. "Multivalent Anti-CD20/Anti-CD22 Bispecific Antibody Fusion Proteins Made by the DNL Method Show Potent Lymphoma Cytotoxicity," *Blood, American Society of Hematology* 108(11):707A, Poster Board No. Session 673-II, Abstract No. 2495, from $48^{th}$ Annual Meeting of the American Society of Hematology, Orland, Florida, Dec. 9-12, 2006, (2006).
Routledge, E.G. et al. "The Effect of Aglycosylation on the Immunogenicity of a Humanized Therapeutic CD3 Monoclonal Antibody," *Transplantation,* 60(8):847-853, (1995).
Routier et al. "The Glycosylation Pattern of a Humanized IgGI Antibody (D1.3) Expressed in CHO Cells," *Glycoconjugate Journal* 14:201-207, (1997).
Roux, K.H. et al. "Comparisons of the ability of human IgG3 hinge mutants, IgM, IgE, and IgA2, to form small immune complexes: a role for flexibility and geometry," *J. Immunol.* 161(8):4083-4090, (1998).
Rudikoff et al. "Single Amino Acid Substitution Altering Antigen-Binding Specificity," *Proc. Natl. Acad. Sci. USA* 79: 1979-1983, (1982).
Rudnick et al. "Affinity and Avidity in Antibody-Based Tumor Targeting," *Cancer Biotherapy & Radiopharmaceuticals* 24(2):155-161, (2009).
Ruppert et al. "Protease Levels in Breast, Ovary and Other Gynecological Tumor Tissues: Prognostic Importance in Breast Cancer," *Cancer Detect. Prev.* 21(5):452-459, (1997).
Sakamoto et al. "Enzyme-Mediated Site-Specific Antibody-Protein Modification Using a ZZ Domain as a Linker," *BioConjugate Chem.* 21:2227-2293 (2010, e-pub. Nov. 11, 2010).
Salfeld, J.G. "Isotype Selection in Antibody Engineering," *Nat. Biotechnol.* 25(12):1369-1372, (Dec. 2007).
Sambrook et al. Molecular Cloning: A Laboratory Manual "The Table of Contents" Cold Spring Harbor, New York: Cold Spring Harbor Laboratory Press, (1989).
Schaefer et al. "Immunoglobulin domain Crossover as a Generic Approach for the Production of Bispecific IgG Antibodies," *Proc. Natl. Acad. Sci. U.S.A.* 108(27):11187-11192, (Jul. 5, 2011, e-pub. Jun. 20, 2011).
Schaefer et al. "Heavy and Light Chain Pairing of Bivalent Quadroma and Knobs-Into-Holes Antibodies Analyzed by UHR-ESI-QTOF Mass Spectrometry," *mAbs* 8(1):49-55, (Jan. 2016).
Schanzer et al. "XGFR*, a Novel Affinity-Matured Bispecific Antibody Targeting IGF-1 R and EGFR With Combined Signaling Inhibition and Enhanced Immune Activation for the Treatment of Pancreatic Cancer," *MABS* 8(4):811-827, (2016).
Scheuer et al. "Anti-Tumoral, Anti-Angiogenic and Anti-Metastatic Efficacy of a Tetravalent Bispecific Antibody (TAvi6) Targeting VEGF-A and Angiopoietin-2," *MABS* 8(3):562-573, (2016).
Schlaeger. "The Protein Hydrolysate, Primatone RL, is a Cost Effective Multiple Growth Promoter of Mammalian Cell Culture in Serum-containing and Serum-free Media and Displays Anti-apoptosis Properties," *Journal of Immunological Methods* 194:191-199, (1996).
Schlaeger et al. "Transient Gene Expression in Mammalian Cells Grown in Serum-free Suspension Culture," *Cytotechnology* 30:71-83, (1999).
Schlatter et al. "On the Optimal Ratio of Heavy to Light Chain Genes for Efficient Recombinant Antibody Production by CHO Cells," *Biotechnol. Prog.* 21:122-133, (2005).
Schmidt et al. "Suppression of Metastasis Formation by a Recombinant Single Chain Antibody-Toxin Targeted to Full-length and Oncogenic Variant EGF Receptors," *Oncogene* 18:1711-1721, (1999).
Schmiedl et al. "Expression of a Bispecific dsFv-$dsFv^1$ Antibody Fragment in *Escherichia coli," Protein Engineering* 13(10):725-734, (Oct. 2000).
Schmiedl et al. "Effects of Unpaired Cysteines on Yield, Solubility and Activity of Different Recombinant Antibody Constructs Expressed in *E. coli" Journal of Immunological Methods* 242:101-114, (2000).
Schoonjans, et al. "Fab Chains as an Efficient Heterodimerization Scaffold for the Production of Recombinant Bispecific and Trispecific Antibody Derivatives," *Journal of Immunology* 165:7050-7057, (2000).
Schwartz et al. "A Superactive Insulin: (B10-aspartic acid]insulin(human)," *Proc. Natl. Acad. Sci. USA* 84:6408-6411, (Sep. 1987).
Scott et al. "Biologic Protease Inhibitors as Novel Therapeutic Agents," *Biochimie* 92(11):1681-1688, (Nov. 2010).
Sensi, M. et al. "Unique Tumor Antigens: Evidence for Immune Control of Genome Integrity and immunogenic Targets for T Cell-Mediated Patient-Specific Immunotherapy," *Clin. Cancer Res.* 12(17):5023-5032, (2006).
Shen et al. "Single variable Domain Antibody as a Versatile Building Block for the Construction of IgG-like Bispecific Antibodies," *Journal of Immunological Methods* 318:65-74, (2007).
Shen et al. "Single Variable Domain-IgG fusion: A Novel Recombinant Approach to Fc Domain-Containing Bispecific Antibodies," *J. of Biological Chemistry* 281(16):10706-10714, (Apr. 21, 2006, e-pub. Feb. 15, 2006).
Shields et al. "High Resolution Mapping of the Binding Site on Human IgG1 for FcγRI, FcγRII, FcγRIII and FcRn and Design of IgG1 Variants with Improved Binding to the FcγR," *Journal of Biological Chemistry* 276 (9):6591-6604, (2001).
Shields et al. "Lack of Fucose on Human IgG1 N-Linked Oligosaccharide Improves Binding to Human FcγRIII and Antibody-dependent Cellular Toxicity," *J Biol Chem.* 277(30):26733-26740, (Jul. 26, 2002).
Shinkawa et al. "The Absence of Fucose but Not the Presence of galactose or Bisecting N-Acetylglucosamine of Human IgG1 Complex-Type Oligosaccharides Shows the Critical Role of Enhancing Antibody-Dependent Cellular cytotoxicity," *J. Biol. Chem.* 278 (5) 3466-3473, (2003).
Simmons et al. "Expression of Full-Length Immunoglobulins in *Escherichia coli*: Rapid and Efficient Production of Aglycosylated Antibodies," *Journal of Immunological Methods* 263:133-147, (2002).

(56) References Cited

OTHER PUBLICATIONS

Simon et al. "Antibody Domain Mutants Demonstrate Autonomy of the Antigen Binding Site," *The EMBO Journal* 9(4):1051-1056, (1990).
Singer, M. and Berg, P. "Genes and Genomes," Moscoer, *MIR* 1(1998) 63-64 (With English Translation.
Smith-Gill et al. "Contributions of Immunoglobulin Heavy and Light Chains to Antibody Specificity for Lysozyme and Two Haptens," *J. Immunol.* 139(12):4135-4144, (Dec. 15, 1987).
Sondermann, P. et al. "The 3.2-A Crystal Structure of the Human IgG1 Fc Fragment-FcγRIII Complex," *Nature,* 406:267-273, (2000).
Song et al. "Light Chain of Natural Antibody Plays a Dominant Role in Protein Antigen Binding," *Biochem. Biophys. Res. Comm.* 268(2):390-394, (Feb. 16, 2000).
Stetler-Stevenson et al. "Progelatinase A Activation During Tumor Cell Invasion," *Invasion Metastasis* 14(1-6):259-268, (1994-1995).
Stevenson et al. "A Chimeric Antibody With Dual Fc Regions (bisFabFc) Prepared by Manipulations at the IgG Hinge," *Anti-cancer Drug Des.* 3(4):219-230, (Mar. 1989).
Stork et al. "A Novel Tri-Functional Antibody Fusion Protein With Improved Pharmacokinetic Properties Generated by Fusing a Bispecific Single-Chain Diabody With an Albumin-Binding Domain From Streptococcal Protein G," *Protein Eng. Des. Sel.* 20(11):569-576, (Nov. 2007, e-pub. Nov. 3, 2007).
Strop, P. et al. "Generating Bispecific Human IgG1 and IgG2 Antibodies from Any Antibody Pair," *Journal of Molecular Biology,* 420(3):204-219, (2012).
Surati, M. et al. "Role of MetMAb (OA-5D5) in c-MET Active lung Malignancies," *Expert Opin. Biol. Ther.* 11(12):1655-1662, (2011).
Ta, H.T. et al. "Enzymatic Single-Chain Antibody Tagging a Universal Approach to Targeted Molecular Imaging and Cell Homing in Cardiovascular Disease," *Circulation Research,* 109(4):365-373, (2011).
Talmadge et al. "Murine Models to Evaluate Novel and Conventional Therapeutic Strategies for Cancer," *Am. J. Pathol.* 170(3):793-804, (Mar. 2007).
Tao et al. "The Differential Ability of Human IgG1 and IgG4 to Activate Complement is Determined by the COOH-terminal Sequence of the $C_H2$ Domain," *J. Exp. Med* 173:1025-1028, (Apr. 1991).
Terpe. "Overview of Tag Protein Fusions: From Molecular and Biochemical Fundamentals to Commercial Systems," *Appl Microbiol Biotechnol* 60:523-533, (2003; e-pub. Nov. 7, 2002).
Thies, M.J. et al. "Folding and Association of the Antibody Domain $C_H3$: Prolyl Isomerization Preceeds Dimerization," *J. Mol. Biol.* 293:67-79, (1999).
Thommesen et al. "Lysine 322 in the Human IgG3 $C_H2$ Domain Is Crucial for Antibody Dependent Complement Activation," *Molecular Immunology* 37:995-1004, (2000).
Thurber et al. "Antibody Tumor Penetration: Transport Opposed by Systemic and Antigen-Mediated Clearance," *Adv. Drug Deliv. Rev.* 60(12):1421-1434, (Sep. 2008, e-pub. Apr. 24, 2008).
Ton-That, H. et al. "Purification and Characterization of Sortase, the Transpeptidase That Cleaves Surface Proteins of *Staphylococcus aureus* at the LPXTG Motif," *Proc. Natl. Acad. Sci. U.S.A.* 96(22):12424-12429, (1999).
Torres, M. et al. "Variable-Region-Identical Antibodies Differing in Isotype Demonstrate Differences in Fine Specificity and Idiotype," *The Journal of Immunology,* 174:2132, (2005).
Tripathi et al. "Laminin-332 is a Substrate for Hepsin, a Protease Associated With Prostate Cancer Progression," *JBC* 283:30576-30584, (2008).
Tsukiji S. et al. "Sortase-Mediated Ligation: A Gift from Gram-Positive Bacteria to Protein Engineering," *Chembiochem,* 10(5):787-798, (2009).
Ueki et al. "Expression of Hepatocyte Growth Factor and its Receptor c-met Proto-Oncogene in Hepatocellular Carcinoma," *Hepatology* 25(4):862-866, (1997).
Umaña et al. "Engineered Glycoforms of an Antineuroblastoma IgG1 with Optimized Antibody-Dependent Cellular Cytotoxic Activity," *Nature Biotechnology* 17(2):176-180 (Feb. 1999).
Urlaub et al. "Isolation of Chinese Hamster Cell Mutants Deficient in Dihydrofolate Reductase Activity," *Proc. Natl. Acad. Sci. USA* 77(7):4216-4220, (Jul. 1980).
Vallböhmer, D. et al. "Molecular Determinants of Cetuximab Efficacy," *J Clin. Oncol.* 23(15):3536-3544, (2005).
Van Dijk and Van De Winkel. "Human Antibodies as Next Generation Therapeutics," *Curr Opin Chem Biol.* 5(4): 368-74, (Aug. 2001).
Van Spriel et al. "Immunotherapeutic Perspective for Bispecific Antibodies," *Immunology Today* 21(8):391-397, (Aug. 2000).
Van't Veer et al. "Gene Expression Profiling Predicts Clinical Outcome of Breast Cancer," *Nature* 415(6871):530-536, (Jan. 2002).
Vazquez-Ortiz et al. "Overexpression of Cathepsin F, Matrix Metalloproteinases 11 and 12 in Cervical Cancer," *BMC Cancer* 5:68, (Jun. 30, 2005).
Velasco et al. "Human cathepsin O. Molecular Cloning From a Breast Carcinoma, Production of the Active Enzyme in *Escherichia coli,* and Expression Analysis in Human Tissues," *J. Biol Chem.* 269(43):27136-27142, (Oct. 28, 1994).
Veveris-Lowe et al. "Seminal Fluid Characterization for Male Fertility and Prostate Cancer: Kallikrein-Related Serine Proteases and whole Proteome Approaches," *Semin Thromb Hemost.* 33(1):87-99, (2007).
Vijayalakshmi. "Antibody Purification Methods," *Applied Biochemistry and Biotechnology* 75:93-102, (1998).
Virnekäs et al. "Trinucleotide Phosphoramidites: Ideal Reagents for the Synthesis of Mixed Oligonucleotides for Random Mutagenesis," *Nucleic Acids Res.* 22(25):5600-5607, (Dec. 25, 1994).
Voskoglou-Nomikos et al. "Clinical Predictive Value of the in Vitro Cell Line, Human Xenograft, and Mouse Allograft Preclinical Cancer Models," *Clin. Can. Res.* 9:4227-4239, (Sep. 15, 2003).
Wagner et al. "Bispecific antibody Generated With Sortase and Click Chemistry Has Broad Antiinfluenza Virus Activity," *Proc. Natl. Acad. Sci. USA* 111:16820-16825, (Nov. 25, 2014).
Walker et al. "Efficient and Rapid Affinity Purification of Proteins Using Recombinant Fusion Proteases," *Bio/Technology* 12:601-605, (1994).
Wallash et al. "Heregulin-Dependent Regulation of HER2/neu Oncogenic Signaling by Heterodimerization With HER3," *Embo J.* 14(17):4267-4275, (1995).
Wang, L. et al. "Expanding the Genetic Code," *Chem. Commun (Camb.),* 7:1-11, (2002).
Ward, E.S. et al. "The Effector Functions of Immunoglobulins: Implications for Therapy" Ther. *Immunol.* 2:77-94, (1995).
Ward et al. "Binding Activities of a Repertoire of Single Immunoglobulin Variable Domains Secreted From *Escherichia coli,*" Nature 341:544-546, (Oct. 12, 1989).
Warren et al. "Regulation by Vascular Endothelial Growth Factor of Human Colon Cancer Tumorigenesis in a Mouse Model of Experimental Liver Metastasis," *J. Clin. Invest.* 95:1789-1797, (1995).
Webber et al. "Preparation and Characterization of a Disulfide-Stabilized Fv Fragment of the Anti-Tac Antibody: Comparison With Its Single-Chain Analog," *Molecular Immunology* 32:249-258, (1995).
Werner et al. "Appropriate Mammalian Expression Systems for Biopharmaceuticals," *Drug Research* 48(8):870-880, (1998).
Wielockx et al. "Matrilysin (matrix metalloproteinase-7): A New Promising Drug Target in Cancer and Inflammation?," *Cytokine Growth Factor Rev.* 15(2-3):111-115, (Apr.-Jun. 2004).
Willems et al. "Optimizing Expression and Purification From Cell Culture Medium of Trispecific Recombinant Antibody Derivatives," *Journal of Chromatography B* 786:161-176, (2003).
Witte M.D. et al. "Preparation of Unnatural N-To-N and C-To-C Protein Fusions," *Proceedings of the National Academy of Sciences of the United States of America,* 109(30):11993-11998, (2012).
Woof et al. "Human Antibody-Fc Receptor Interactions Illuminated by Crystal Structures," *Nat. Rev. Immunol.* 4:1-11, (2004).
Wright et al. "ADAM28: A Potential Oncogene Involved in Asbestos-Related Lung Adenocarcinomas," *Genes Chromosomes Cancer* 49(8):688-698, (Aug. 2010).
Wright and Morrison, "Effect of Glycosylation on Antibody Function: Implications for Genetic Engineering," *Trends in Biotechnology* 15:26-32, (1997).

(56) References Cited

OTHER PUBLICATIONS

Wu et al. "Simultaneous Targeting of Multiple Disease Mediators by a Dual-Variable-Domain Immunoglobulin," *Nature Biotechnology* 25(11):1290-1297, (Nov. 2007).
Xie et al. "A New Format of Bispecific Antibody: Highly Efficient Heterodimerization, Expression and Tumor Cell Lysis," *J. of Immunol. Methods* 296:95-101, (2005).
Yancopoulos, G.D. et al. "Vascular-Specific Growth Factors and Blood Vessel Formation," *Nature* 407:242-248, (Sep. 14, 2000).
Yu, Y.J. et al. "Developing Therapeutic Antibodies for Neurodegenerative Disease," *Neurotherapeutics* 10(3):459-472, (Apr. 3, 2013).
Zeidler et al. "Simultaneous Activation of T Cells and Accessory Cells by a New Class of Intact Bispecific Antibody Results in Efficient Tumor Cell Killing," *Journal of Immunology* 163:1246-1252, (1999).
Ziolkowska et al. "High Levels of IL-17 in Rheumatoid Arthritis Patients: IL-15 Triggers In Vitro IL-17 Production via Cyclosporin A-Sensitive Mechanism," *J. Immunol.* 164:2832-2838, (2000).
Zuo et al. "An Efficient Route to the Production of an Igg-Like Bispecific Antibody," *Protein Engineering* 13(5):361-367, (2000).
Patentee's Submission dated Jun. 11, 2012, for European Patent No. 1 957 533, filed on Oct. 23, 2006, Reply to Communication Pursuant to Article 94(3) EPC dated Dec. 2, 2011, 7 pages.
Chinese Office Action dated Mar. 28, 2012, for Chinese Application No. 200880120258.8, 10 pages.
Korean Office Action dated Feb. 24, 2012, for Korean Patent Application No. 20107013773, 6 pages.
Citations from Israeli Office Action, dated Feb. 29, 2012, in Israeli Patent Application No. 205285, 2 pages.
Japanese Office Action dated Aug. 14, 2012, for Japanese Patent Application No. 2010-538440, 12 pages.
Japanese Office Action dated Aug. 14, 2012, for Japanese Patent Application No. 2010-538441, 11 pages.
Korean Office Action dated Jan. 31, 2012, for Korean Patent Application No. 2010-7013760, 11 pages.
European Search Report dated Mar. 14, 2006, for European Patent Application No. 07024864.6, 8 pages.
European Search Report dated Aug. 31, 2009, for European Patent Application No. 09005108.7, 6 pages.
Taiwanese Search Report for Taiwanese Patent Application No. 099110151, filed on Apr. 1, 2010, Completion of Search Sep. 12, 2012, 1 page.
International Search Report dated Aug. 5, 2010, for PCT Application No. PCT/EP2010/003559, filed on Jun. 14, 2010, 10 pages.
Russian Office Action dated Apr. 18, 2013, for Russian Patent Application No. 2010 129 539, 3 pages.
Russian Office Action dated Oct. 8, 2014, for Russian Patent Application No. 2012 100 865, 3 pages.
International Search Report dated Jul. 29, 2013, for PCT Patent Application No. PCT/EP2013/060529, filed on May 22, 2013, 7 pages.
International Search Report dated Dec. 6, 2011, for PCT Patent Application No. PCT/EP2011/064476 filed on Aug. 23, 2011, 7 pages.
International Search Report dated Dec. 6, 2011, for PCT Patent Application No. PCT/EP2011/064468 filed on Aug. 23, 2011, 7 pages.
International Search Report dated Sep. 9, 2015, for PCT Application No. PCT/EP2015/057165, filed on Apr. 1, 2015, 5 pages.
International Search Report, dated Sep. 29, 2015 for PCT/EP2015/067369, filed on Jul. 29, 2015, 5 pages.
International Search Report dated Jan. 16, 2015, for PCT Application No. PCT/EP2014/071531, filed on Oct. 8, 2014, 6 pages.
International Preliminary Report on Patentability for PCT Application No. PCT/EP2014/079353, dated Jul. 12, 2016, filed Dec. 29, 2014, 9 pages.
International Search Report for PCT Application No. PCT/EP2014/079353, dated Apr. 20, 2015, filed Dec. 29, 2014, 6 pages.
International Search Report dated May 8, 2014, for PCT Patent Application No. PCT/EP2013/063258, filed on Jun. 25, 2013, 7 pages.
Written Opinion of the International Searching Authority dated Jul. 29, 2013, for PCT Patent Application No. PCT/EP2013/060529, filed on May 22, 2013, 7 pages.
Written Opinion of the International Searching Authority dated Dec. 6, 2011, for PCT Patent Application No. PCT/EP2011/064476 filed on Aug. 23, 2011, 4 pages.
Written Opinion International for PCT Application No. PCT/EP2014/079353, dated Apr. 20, 2015, filed Dec. 29, 2014, 9 pages.
Written Opinion of the International Searching Authority dated Dec. 6, 2011, for PCT Patent Application No. PCT/EP2011/064468 filed on Aug. 23, 2011, 4 pages.
Written Opinion dated Sep. 9, 2015, for PCT Application No. PCT/EP2015/057165, filed on Apr. 1, 2015, 7 pages.
Written Opinion dated Jan. 16, 2015, for PCT Application No. PCT/EP2014/071531, filed on Oct. 8, 2014, 5 pages.
Todorovska, A. et al. (2001). "Design and Application of Diabodies, Triabodies and Tetrabodies for Cancer Targeting," J. of Immunological Methods 248 :47-66.
Zhang, Z. et al. "Human Polyvalent Immunoglobulin for Treatment," Foreign Medicine Blood, Transfusion and Hematology 23(6):365, (Dec. 31, 2000). Abstract No. 229. With English Translation.

* cited by examiner

A

B mAu
t[min]
1
2
0
1.0
2.0
3.0
0 2 4 6 8 10 12

SEQUENCE LISTING

<160> NUMBER OF SEQ ID NOS: 9

<210> SEQ ID NO 1
<211> LENGTH: 445
<212> TYPE: PRT
<213> ORGANISM: Artificial Sequence
<220> FEATURE:
<223> OTHER INFORMATION: Description of Artificial Sequence: Synthetic
c-Met 5D5 MoAb-Dimer ("CH3-wt") - modified heavy
chain a) VL-CH1-CH2-CH3 polypeptide

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

-continued

Arg Asp Glu Leu Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 2
<211> LENGTH: 453
<212> TYPE: PRT
<213> ORGANISM: Artificial Sequence
<220> FEATURE:
<223> OTHER INFORMATION: Description of Artificial Sequence: Synthetic c-Met 5D5 MoAb-Dimer ("CH3-wt") - modified heavy chain b) VH-CL-CH2-CH3 polypeptide

<400> SEQUENCE: 2

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Thr Phe Thr Ser Tyr
20 25 30

Trp Leu His Trp Val Arg Gln Ala Pro Gly Lys Gly Leu Glu Trp Val
35 40 45

Gly Met Ile Asp Pro Ser Asn Ser Asp Thr Arg Phe Asn Pro Asn Phe
50 55 60

Lys Asp Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Thr Tyr Arg Ser Tyr Val Thr Pro Leu Asp Tyr Trp Gly Gln Gly
100 105 110

Thr Leu Val Thr Val Ser Ser Ala Ser Val Ala Ala Pro Ser Val Phe
115 120 125

Ile Phe Pro Pro Ser Asp Glu Gln Leu Lys Ser Gly Thr Ala Ser Val
130 135 140

Val Cys Leu Leu Asn Asn Phe Tyr Pro Arg Glu Ala Lys Val Gln Trp
145 150 155 160

Lys Val Asp Asn Ala Leu Gln Ser Gly Asn Ser Gln Glu Ser Val Thr
165 170 175

Glu Gln Asp Ser Lys Asp Ser Thr Tyr Ser Leu Ser Ser Thr Leu Thr
180 185 190

Leu Ser Lys Ala Asp Tyr Glu Lys His Lys Val Tyr Ala Cys Glu Val
195 200 205

Thr His Gln Gly Leu Ser Ser Pro Val Thr Lys Ser Phe Asn Arg Gly
210 215 220

Glu Cys Asp Lys Thr His Thr Cys Pro Pro Cys Pro Ala Pro Glu Leu
225 230 235 240

Leu Gly Gly Pro Ser Val Phe Leu Phe Pro Pro Lys Pro Lys Asp Thr
245 250 255

-continued

```
Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 3
<211> LENGTH: 440
<212> TYPE: PRT
<213> ORGANISM: Artificial Sequence
<220> FEATURE:
<223> OTHER INFORMATION: Description of Artificial Sequence: Synthetic
      IGF1R AK18 MoAb-Dimer ("CH3-wt") - modified heavy
      chain a) VL-CH1-CH2-CH3 polypeptide

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
```

-continued

```
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
    210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
                325                 330                 335

Arg Glu Pro Gln Val Tyr Thr Leu Pro Pro Ser Arg Asp Glu Leu Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
            420                 425                 430

Ser Leu Ser Leu Ser Pro Gly Lys
        435                 440


<210> SEQ ID NO 4
<211> LENGTH: 452
<212> TYPE: PRT
<213> ORGANISM: Artificial Sequence
<220> FEATURE:
<223> OTHER INFORMATION: Description of Artificial Sequence: Synthetic
      IGF1R AK18 MoAb-Dimer ("CH3-wt") - modified heavy
      chain b) VH-CL-CH2-CH3 polypeptide

<400> SEQUENCE: 4

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60
```

```
Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Val Ala Ala Pro Ser Val Phe Ile
        115                 120                 125

Phe Pro Pro Ser Asp Glu Gln Leu Lys Ser Gly Thr Ala Ser Val Val
    130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
        195                 200                 205

His Gln Gly Leu Ser Ser Pro Val Thr Lys Ser Phe Asn Arg Gly Glu
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 5
<211> LENGTH: 445

-continued

<212> TYPE: PRT
<213> ORGANISM: Artificial Sequence
<220> FEATURE:
<223> OTHER INFORMATION: Description of Artificial Sequence: Synthetic
Her3 205 MoAb-Dimer ("CH3-wt") - modified heavy
chain a) VL-CH1-CH2-CH3 polypeptide

<400> SEQUENCE: 5

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln

```
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 6
<211> LENGTH: 454
<212> TYPE: PRT
<213> ORGANISM: Artificial Sequence
<220> FEATURE:
<223> OTHER INFORMATION: Description of Artificial Sequence: Synthetic
      Her3 205 MoAb-Dimer ("CH3-wt") - modified heavy
      chain b) VH-CL-CH2-CH3 polypeptide

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
            20                  25                  30

Tyr Ile Ser Trp Val Arg Gln Ala Pro Gly Gln Gly Leu Glu Trp Met
        35                  40                  45

Gly Trp Ile Tyr Ala Gly Thr Gly Ser Pro Ser Tyr Asn Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Arg Asp Tyr Tyr Ser Asn Ser Leu Thr Tyr Trp Gly Gln
            100                 105                 110

Gly Thr Leu Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285
```

-continued

```
Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450


<210> SEQ ID NO 7
<211> LENGTH: 446
<212> TYPE: PRT
<213> ORGANISM: Artificial Sequence
<220> FEATURE:
<223> OTHER INFORMATION: Description of Artificial Sequence: Synthetic
      IGF1R AK18 MoAb-Dimer - modified heavy chain
      a) VL-CH1-CH2-CH3 with IgA-CH3 domain polypeptide

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175
```

-continued

```
Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
    210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Asn Thr
                325                 330                 335

Phe Arg Pro Glu Val His Leu Leu Pro Pro Pro Ser Glu Glu Leu Ala
            340                 345                 350

Leu Asn Glu Leu Val Thr Leu Thr Cys Leu Ala Arg Gly Phe Ser Pro
        355                 360                 365

Lys Asp Val Leu Val Arg Trp Leu Gln Gly Ser Gln Glu Leu Pro Arg
    370                 375                 380

Glu Lys Tyr Leu Thr Trp Ala Ser Arg Gln Glu Pro Ser Gln Gly Thr
385                 390                 395                 400

Thr Thr Phe Ala Val Thr Ser Ile Leu Arg Val Ala Ala Glu Asp Trp
                405                 410                 415

Lys Lys Gly Asp Thr Phe Ser Cys Met Val Gly His Glu Ala Leu Pro
            420                 425                 430

Leu Ala Phe Thr Gln Lys Thr Ile Asp Arg Leu Ala Gly Lys
        435                 440                 445


<210> SEQ ID NO 8
<211> LENGTH: 458
<212> TYPE: PRT
<213> ORGANISM: Artificial Sequence
<220> FEATURE:
<223> OTHER INFORMATION: Description of Artificial Sequence: Synthetic
      IGF1R AK18 MoAb-Dimer - modified heavy chain
      b) VH-CL-CH2-CH3 with IgA-CH3 domain polypeptide

<400> SEQUENCE: 8

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
```

-continued

```
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Val Ala Ala Pro Ser Val Phe Ile
        115                 120                 125

Phe Pro Pro Ser Asp Glu Gln Leu Lys Ser Gly Thr Ala Ser Val Val
    130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
        195                 200                 205

His Gln Gly Leu Ser Ser Pro Val Thr Lys Ser Phe Asn Arg Gly Glu
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Asn Thr Phe Arg Pro Glu
            340                 345                 350

Val His Leu Leu Pro Pro Pro Ser Glu Glu Leu Ala Leu Asn Glu Leu
        355                 360                 365

Val Thr Leu Thr Cys Leu Ala Arg Gly Phe Ser Pro Lys Asp Val Leu
    370                 375                 380

Val Arg Trp Leu Gln Gly Ser Gln Glu Leu Pro Arg Glu Lys Tyr Leu
385                 390                 395                 400

Thr Trp Ala Ser Arg Gln Glu Pro Ser Gln Gly Thr Thr Thr Phe Ala
                405                 410                 415

Val Thr Ser Ile Leu Arg Val Ala Ala Glu Asp Trp Lys Lys Gly Asp
            420                 425                 430

Thr Phe Ser Cys Met Val Gly His Glu Ala Leu Pro Leu Ala Phe Thr
        435                 440                 445

Gln Lys Thr Ile Asp Arg Leu Ala Gly Lys
    450                 455
```

<210> SEQ ID NO 9
<211> LENGTH: 5
<212> TYPE: PRT

-continued

```
<213> ORGANISM: Artificial Sequence
<220> FEATURE:
<223> OTHER INFORMATION: Description of Artificial Sequence: Synthetic
      5xHis tag

<400> SEQUENCE: 9

His His His His His
1               5
```

NUCLEIC ACID ENCODING DUAL FC ANTIGEN BINDING PROTEINS

CROSS-REFERENCE TO RELATED APPLICATIONS

The present application is a divisional of U.S. patent application Ser. No. 13/406,411, filed on Feb. 27, 2012, which claims priority under 35 USC § 119(a) to European patent application number EP 11156320.1, filed 28 Feb. 2011, the contents of which are incorporated herein by reference.

SEQUENCE LISTING

The content of the following submission on ASCII text file is incorporated herein by reference in its entirety: a computer readable form (CRF) of the Sequence Listing (file name: 146392015610SEQLIST.TXT, date recorded: Jul. 23, 2018, size: 33 KB).

TECHNICAL FIELD

The present invention relates to antigen binding proteins comprising two Fc parts, methods for their production, pharmaceutical compositions containing said antigen binding proteins, and uses thereof.

BACKGROUND OF THE INVENTION

In the last two decades various engineered antibody derivatives, either mono or- multispecific, either mono- or multivalent have been developed and evaluated (see e.g. Holliger, P., et al., Nature Biotech. 23 (2005) 1126-1136; Fischer, N., and Léger O., Pathobiology 74 (2007) 3-14).

US 2004/0033561 refers to the DNA and the production of monovalent monobodies by co-expression of a heavy chain and a modified heavy chain. However during expression a considerably amount of undesired homodimer is formed as by-product, which is difficult to separate from the desired heterodimeric monobodies, as the homodimer and the heterodimer have the same or similar molecular weights. WO 2007/048037 refers to monovalent IgGs which corresponds to the heterodimeric monobodies of US 2004/0033561, but which can have a tagging moiety attached to the heavy chain for easier purification of the heterodimer from the difficult-to-separate homodimeric by-product.

SUMMARY OF THE INVENTION

The invention comprises an antigen binding protein comprising a) two modified heavy chains of an antibody which specifically binds to an antigen, wherein VH of each heavy chain is replaced by the VL of said antibody, said modified heavy chains being associated with each other via their CH domains of the Fc part;

b) two modified heavy chains of said antibody wherein CH1 of each heavy chain is replaced by CL of said antibody, said modified heavy chains being associated with each other via their CH domains of the Fc part;

and wherein the VL domains of the heavy chains of a) are associated with the VH domains of the heavy chains of b), and the CH1 domains of the heavy chains of a) are associated with the CL domains of the heavy chains of b).

In one embodiment the antigen binding protein according to the invention is characterized in that the CH3 domains of the Fc part of the modified heavy chains of a) and the CH3 domains of the Fc part of the modified heavy chains of b) are of the same isotype.

In one embodiment the antigen binding protein according to the invention is characterized in that the CH2 and CH3 domains of the Fc part of the modified heavy chains of a) and the CH2 and CH3 domains of the Fc part of the modified heavy chains of b) are of the same isotype.

In one embodiment the antigen binding protein according to the invention is characterized in that the CH2 and CH3 domains of the Fc part of the modified heavy chains of a) and the CH2 and CH3 domains of the Fc part of the modified heavy chains of b) are of the IgG isotype.

In one embodiment the antigen binding protein according to the invention is characterized in that the CH2 and CH3 domains of the Fc part of the modified heavy chains of a) and the CH2 and CH3 domains of the Fc part of the modified heavy chains of b) are of the IgG1 isotype.

In one embodiment the antigen binding protein according to the invention is characterized in comprising a) two modified heavy chains comprising the amino acid sequence of SEQ ID NO:1; and b) two modified heavy chains comprising the amino acid sequence of SEQ ID NO:2;

a) two modified heavy chains comprising the amino acid sequence of SEQ ID NO:3; and b) two modified heavy chains comprising the amino acid sequence of SEQ ID NO:4; or a) two modified heavy chains comprising the amino acid sequence of SEQ ID NO:5; and b) two modified heavy chains comprising the amino acid sequence of SEQ ID NO:6.

In one embodiment the antigen binding protein according to the invention is characterized in that either the two modified heavy chains of a), or the two modified heavy chains of b), are further modified by the amino acid substitutions S364G, L368F, D399K and K409D (wherein the amino acid positions are numbered according to the EU Index of Kabat).

In one embodiment the antigen binding protein according to the invention is characterized in that a) two modified heavy chains comprising the amino acid sequence of SEQ ID NO:1; and b) two modified heavy chains comprising the amino acid sequence of SEQ ID NO:2;

wherein either the two modified heavy chains of a), or the two modified heavy chains of b), are further modified by the amino acid substitutions S364G, L368F, D399K and K409D (wherein the amino acid positions are numbered according to the EU Index of Kabat);

a) two modified heavy chains comprising the amino acid sequence of SEQ ID NO:3; and b) two modified heavy chains comprising the amino acid sequence of SEQ ID NO:4;

wherein either the two modified heavy chains of a), or the two modified heavy chains of b), are further modified by the amino acid substitutions S364G, L368F, D399K and K409D (wherein the amino acid positions are numbered according to the EU Index of Kabat);

or a) two modified heavy chains comprising the amino acid sequence of SEQ ID NO:5; and
b) two modified heavy chains comprising the amino acid sequence of SEQ ID NO:6 wherein either the two modified heavy chains of a), or the two modified heavy chains of b), are further modified by the amino acid substitutions S364G, L368F, D399K and K409D (wherein the amino acid positions are numbered according to the EU Index of Kabat).

In one embodiment the antigen binding protein according to the invention is characterized in that the CH3 domains of the Fc part of the modified heavy chains of a) and the CH3 domains of the Fc part of the modified heavy chains of b) are of a different isotype.

In one embodiment the antigen binding protein according to the invention is characterized in that the CH3 domains of the Fc part of the modified heavy chains of a) are of the IgG1 isotype;

and the CH3 domains of the Fc part of the modified heavy chains of b) are of the IgA isotype.

In one embodiment the antigen binding protein according to the invention is characterized in comprising a) two modified heavy chairs comprising the amino acid sequence of SEQ ID NO:7; and
b) two modified heavy chains comprising the amino acid sequence of SEQ ID NO:4.

In one embodiment the antigen binding protein according to the invention is characterized in comprising a) two modified heavy chains comprising the amino acid sequence of SEQ ID NO:3; and
b) two modified heavy chains comprising the amino acid sequence of SEQ ID NO:8.

In one embodiment the antigen binding protein according to the invention is characterized in that The CH2 and CH3 domains of the Fc part of the modified heavy chains of a) are of the IgG1 isotype;

and the CH2 and CH3 domains of the Fc part of the modified heavy chains of b) are of the IgA isotype.

In one embodiment the antigen binding protein according to the invention is characterized in that the CH2 domain of the Fc parts of a) and b) are of IgG1 isotype, and the antigen binding protein is afucosylated with an amount of fucose of 80% or less (preferably of 65% to 5%) of the total amount of oligosaccharides (sugars) at Asn297 is of human IgG1 isotype.

The invention further comprises a method for the preparation of an antigen binding protein according to the invention comprising the steps of a) transforming a host cell with vectors comprising nucleic acid molecules encoding an antigen binding protein according to the invention
b) culturing the host cell under conditions that allow synthesis of said antigen binding protein molecule; and
c) recovering said antigen binding protein molecule from said culture.

The invention further comprises nucleic acid encoding the antigen binding protein according to the invention.

The invention further comprises vectors comprising nucleic acid encoding the antigen binding protein according to the invention.

The invention further comprises host cell comprising said vectors.

The invention further comprises composition, preferably a pharmaceutical or a diagnostic composition of an antigen binding protein according to the invention.

The invention further comprises pharmaceutical composition comprising an antigen binding protein according to the invention.

The invention further comprises method for the treatment of a patient in need of therapy, characterized by administering to the patient a therapeutically effective amount of an antigen binding protein according to the invention.

It has now been found that the antigen binding proteins according to the invention have valuable characteristics such as biological or pharmacological activities (as e.g. enhanced ADCC compared to parent antibodies). They can be used e.g. for the treatment of diseases such as cancer. The antigen binding proteins according to the invention have furthermore highly valuable pharmacokinetic properties (like e.g. AUC0-inf, Cmax or C0).

DESCRIPTION OR THE FIGURES

Figure 1B:
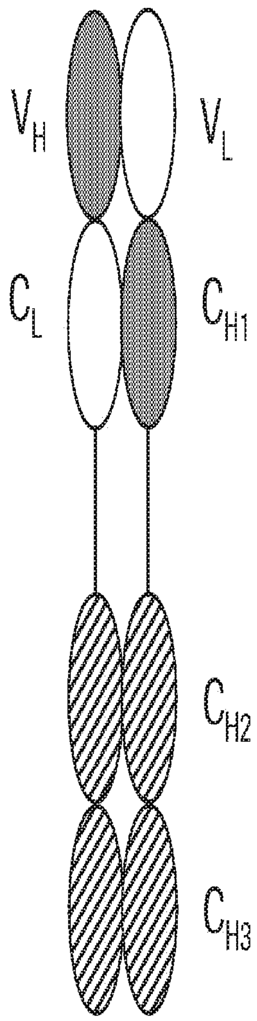

FIGS. 1A and B: FIG. 1A) Schematic structure of the antigen binding protein according to the invention (abbreviated MoAb-Dimer) with CH1-CL, crossover. FIG. 1B) Scheme of the major byproduct—monovalent antibody monomer (MoAb) with CH1-CL crossover (abbreviated MoAb).

Figure 1C:
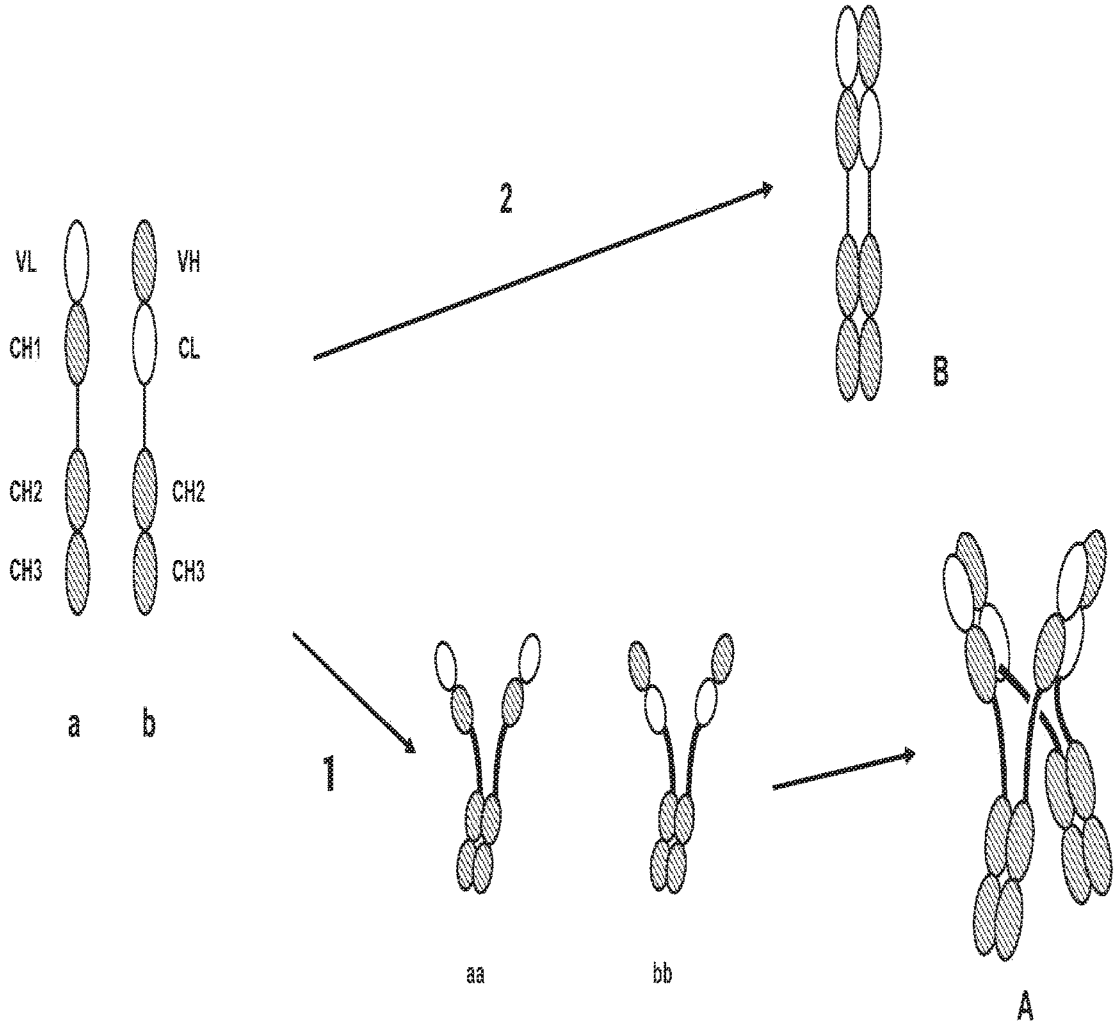

FIG. 1C: C) Association of two modified heavy chains a and b: Heterodimerisation of two different chains (a with b) directly leads to the monovalent antibody B (route 2). Homodimerisation of two identical chains (a with a and b with b) leads to the putative intermediates aa and bb (via route 1) that can associate to form "MoAb-Dimer" A. Modification of the CH3-CH3 contacts may affect distribution of products A (MoAb-Dimer) and B (MoAb). Modifications that favor heterodimerisation (e.g. knobs into holes) will increase the relative amount of compound B via route 2, whereas modifications that maintain attractive interactions between identical chains but lead to repulsion of different chains (e.g. CH3 domains of a and b taken from different isotypes) will favor route 1 and thus increase the amount of A. White: light chain domains. Dashed: heavy chain domains.

Figure 2A:
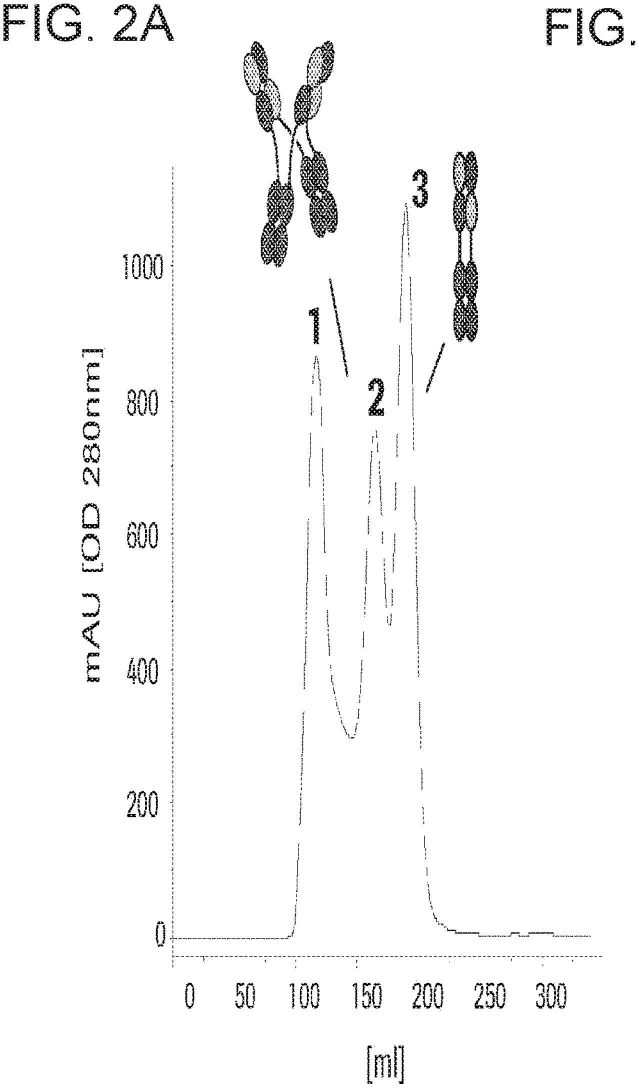
Figure 2B:
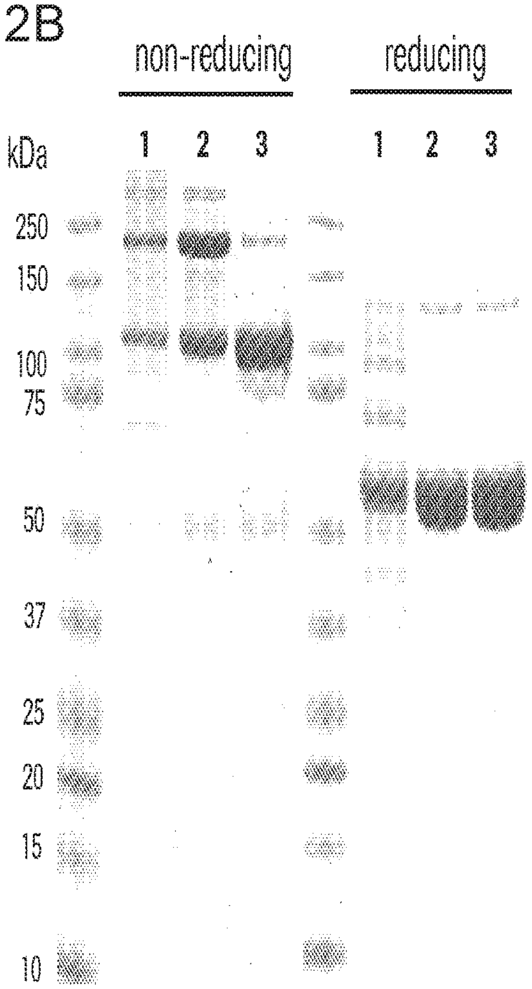

FIG. 2: Biochemical characterization of MoAb-Dimer c-Met (5D5 MoAb-Dimer ("CH3-wt")) (CH3-wt refers to the unchanged, wild type CH3 domain). (A) Protein A purified antibody was separated on an SUPERDEX® (dextran covalently bonded to crosslinked agarose) (200 26/60 column. (B) Peak fractions (1, 2, 3) were pooled and subjected to SDS-PAGE under non-reducing and reducing conditions. Polyacrylamide gels were stained with Coomassie Blue dye. Individual peaks correspond to MoAb (3), MoAb-Dimer (2) and a higher molecular weight aggregate (1).

Figure 3A:
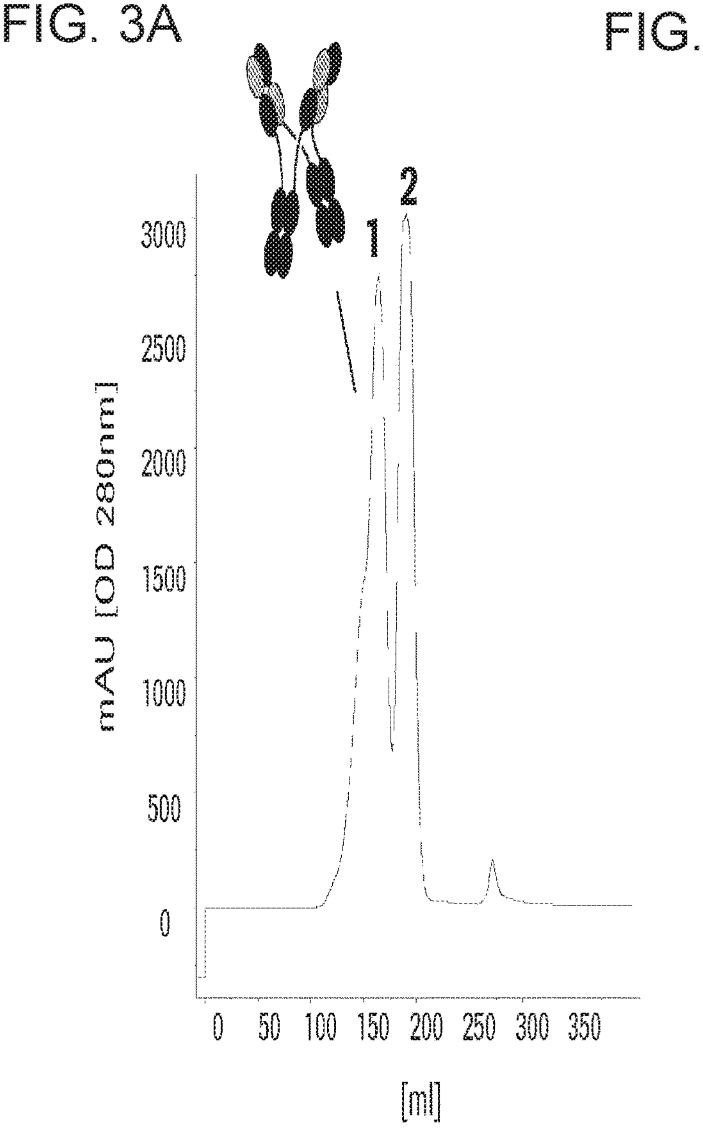
Figure 3B:
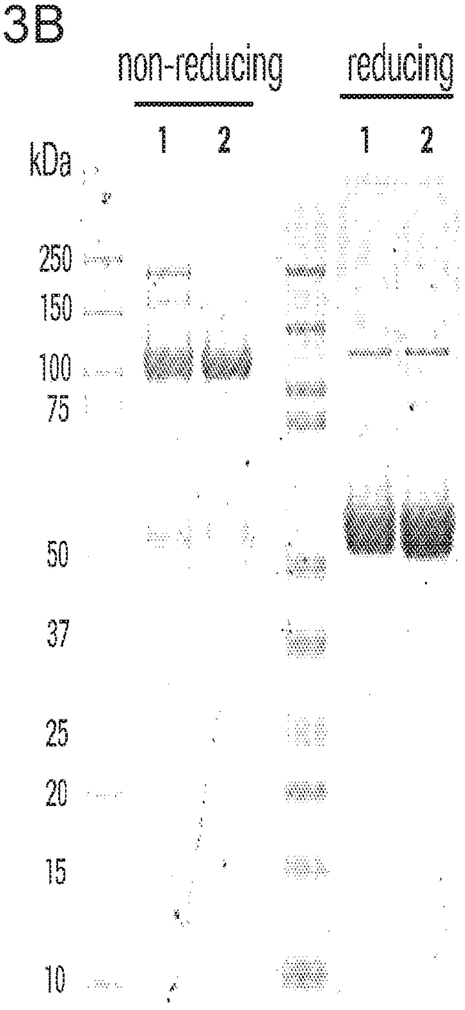
Figure 3C:
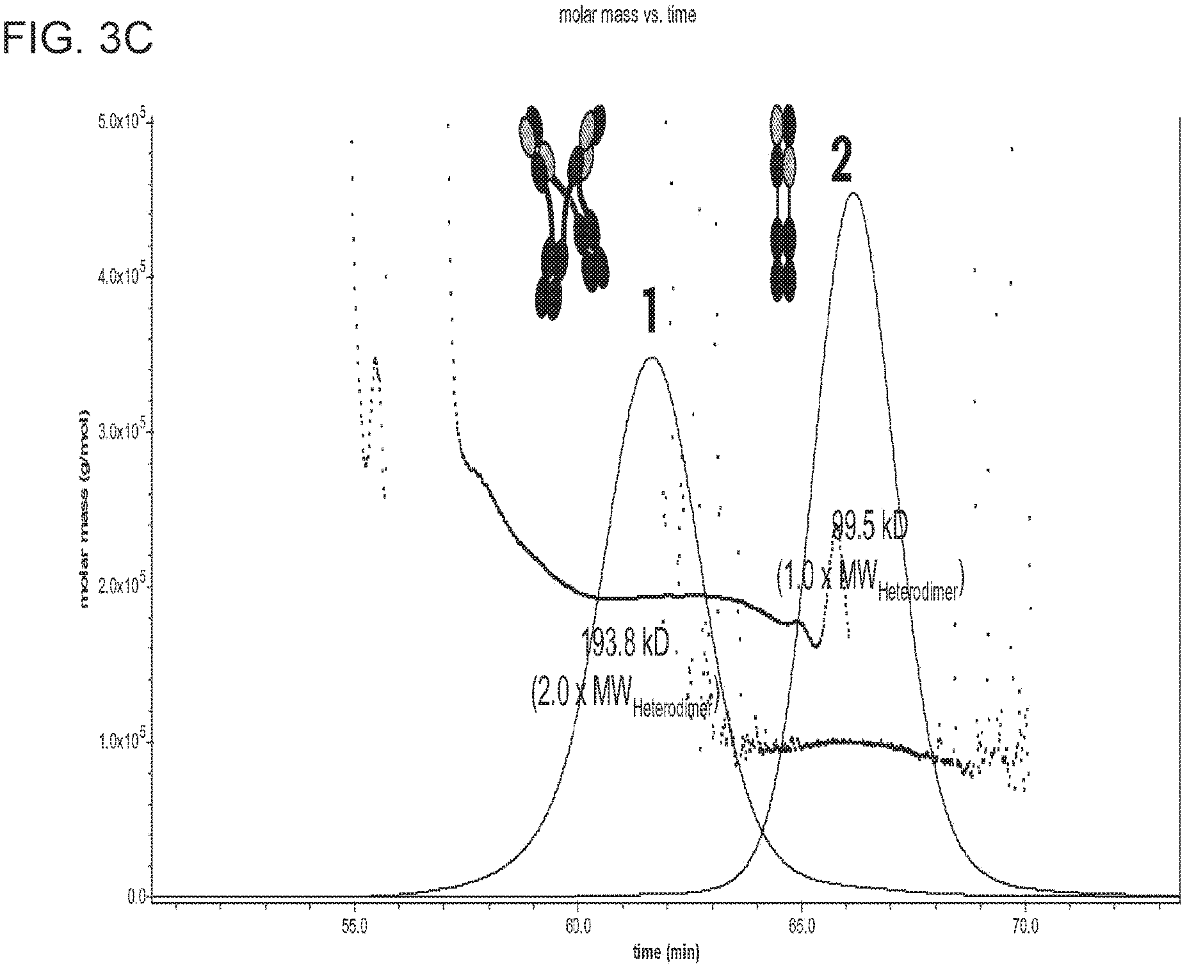

FIG. 3: Biochemical characterization of MoAb-Dimer IGF-IR (IGF-IR AK18 MoAb-Dimer ("CH3-wt")) (CH3-wt refers to the unchanged, wild type CH3 domain). (A) Protein A purified antibody was separated on an SUPERDEX® 200 26/60 column. (B) Peak fractions (1, 2) were pooled and subjected to SDS-PAGE under non-reducing and reducing conditions. Polyacrylamide gels were stained with Coomassie Blue dye. Individual peaks correspond to MoAb (2)

and MoAb-Dimer (1). C) The molecular mass of the peaks fractions 1 and 2 was investigated by SEC-MALLS.

Figure 4A:
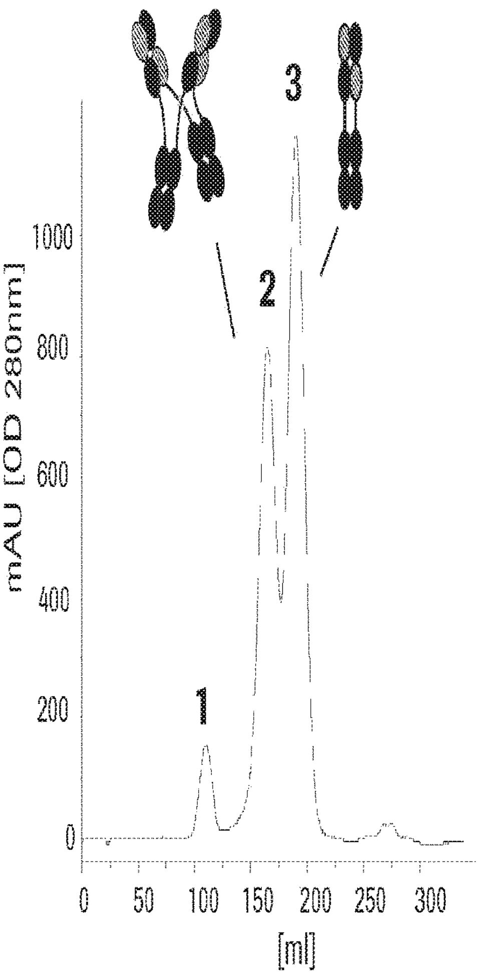
Figure 4B:
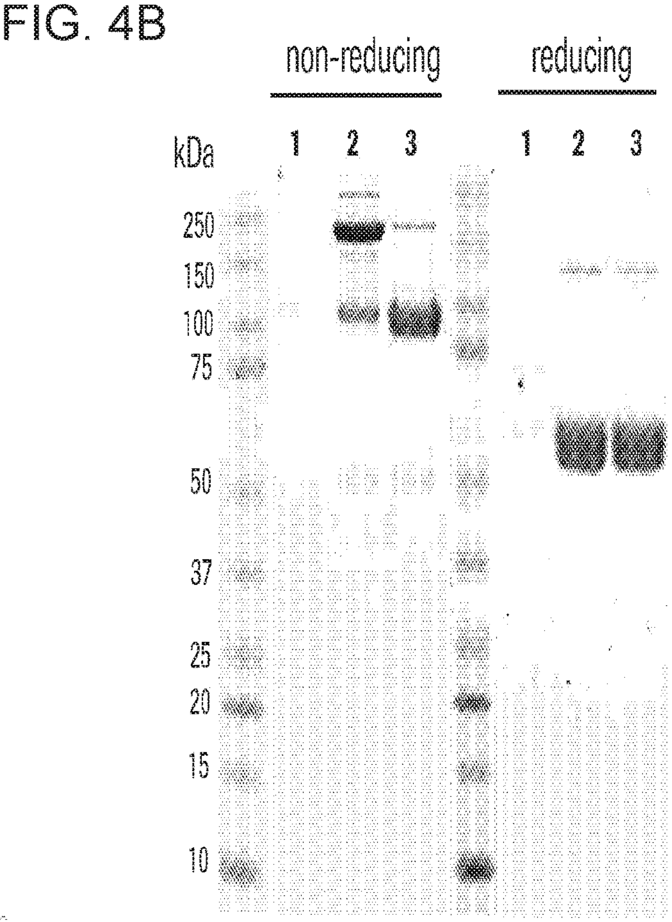

FIGS. 4A & 4B: Biochemical characterization of Her3 205 MoAb-Dimer ("CH3-wt") (CH3-wt refers to the unchanged, wild type CH3 domain). (FIG. 4A) Protein A purified antibody was separated on an Superdex 200 26/60 column. (FIG. 4B) Peak fractions (1, 2) were pooled and subjected to SDS-PAGE under non-reducing and reducing conditions. Polyacrylamide gels were stained with Coomassie Blue dye. Individual peaks correspond to MoAb (3), MoAb-Dimer (2) and a higher molecular weight aggregate (1).

Figure 5:
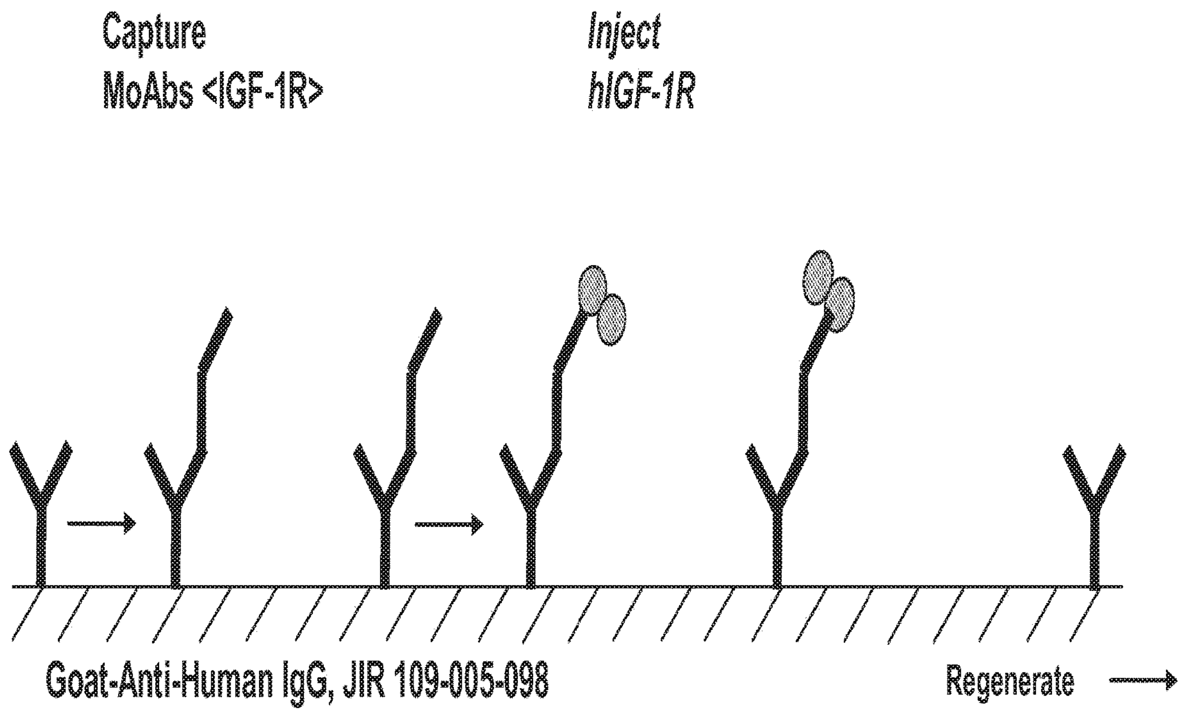

FIG. 5: Schematic picture of the surface plasmon resonance assay applied to analyze the IGF-1R binding affinity. An anti human lgG antibody (JIR 109-005-098) was immobilized on the surface of a CM5 biosensorchip and subsequently captured MoAb or MoAb-Dimer antibodies. Further injection of recombinant lGF-1R ectodomain confirmed functionality of antigen binding sites in MoAb and MoAb-Dimer molecules.

Figure 6A:
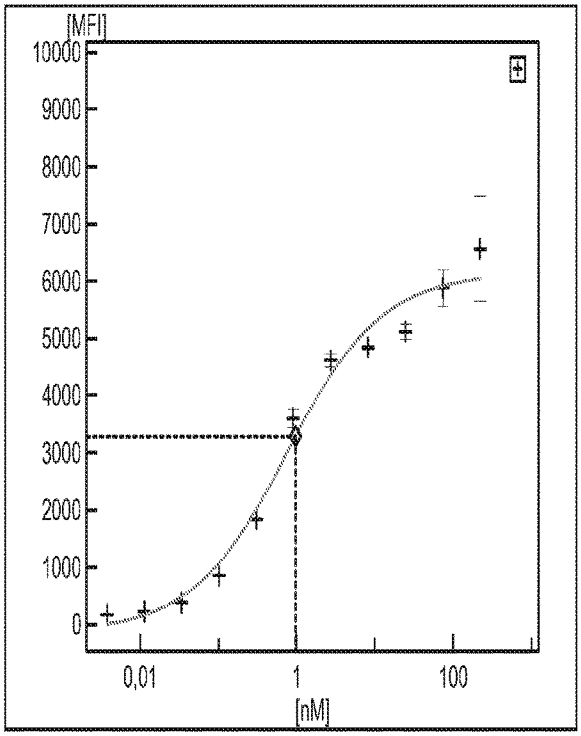
Figure 6B:
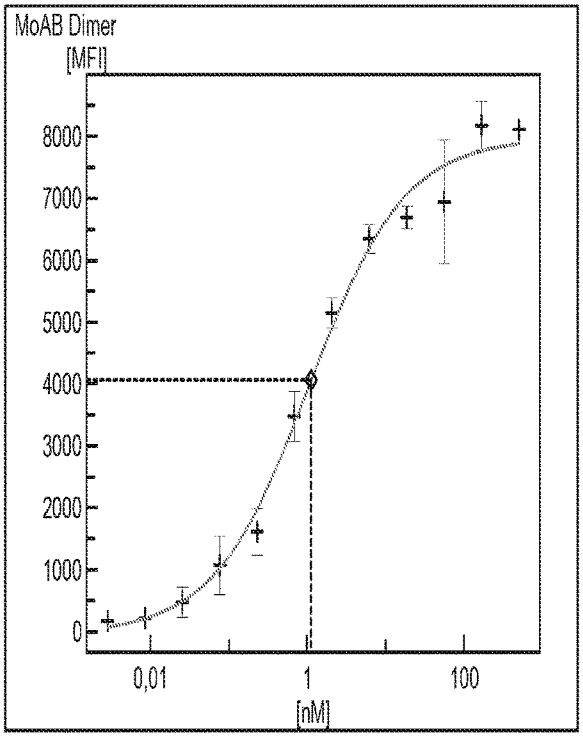

FIGS. 6A & 6B: Cellular binding of MoAb-Dimer (IGF-1R AK18 MoAb-Dimer ("CH3-wt") (B) and parent antibody Mab IGF-1R (A) to A549 cells with flow cytometric analysis. A549 cells were incubated with a dilution series of the indicated antibodies. Bound antibodies were visualized with an Fc-binding secondary fluorophor coupled antibody.

Figure 7:
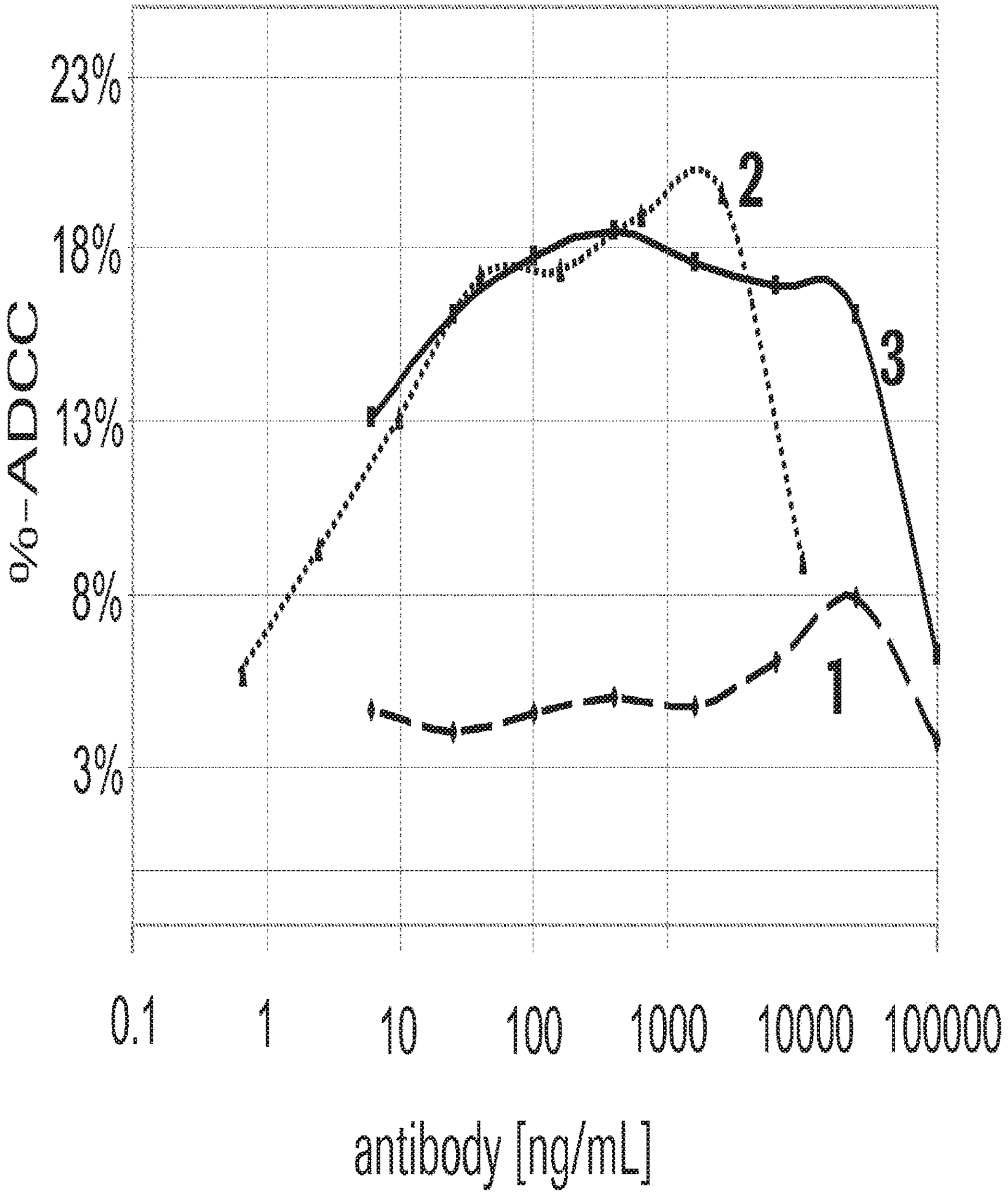

FIG. 7: ADCC Assay with IGF1R Mab non-glycoengineered (non-ge) and glycoengineered (ge) and non-glycoengineered IGF-1R MoAb-Dimer (IGF1R AK18 MoAb-Dimer ("CH3-wt")). Donor derived peripheral blood mononuclear cells (PBMC) were incubated with prostate cancer cells (DU145) in the presence of non-ge IGF1R Mab (1), ge IGF1R Mab (2) and non-ge IGF1R AKI8 MoAb-Dimer ("CH3-wt") (3).

Figure 8:
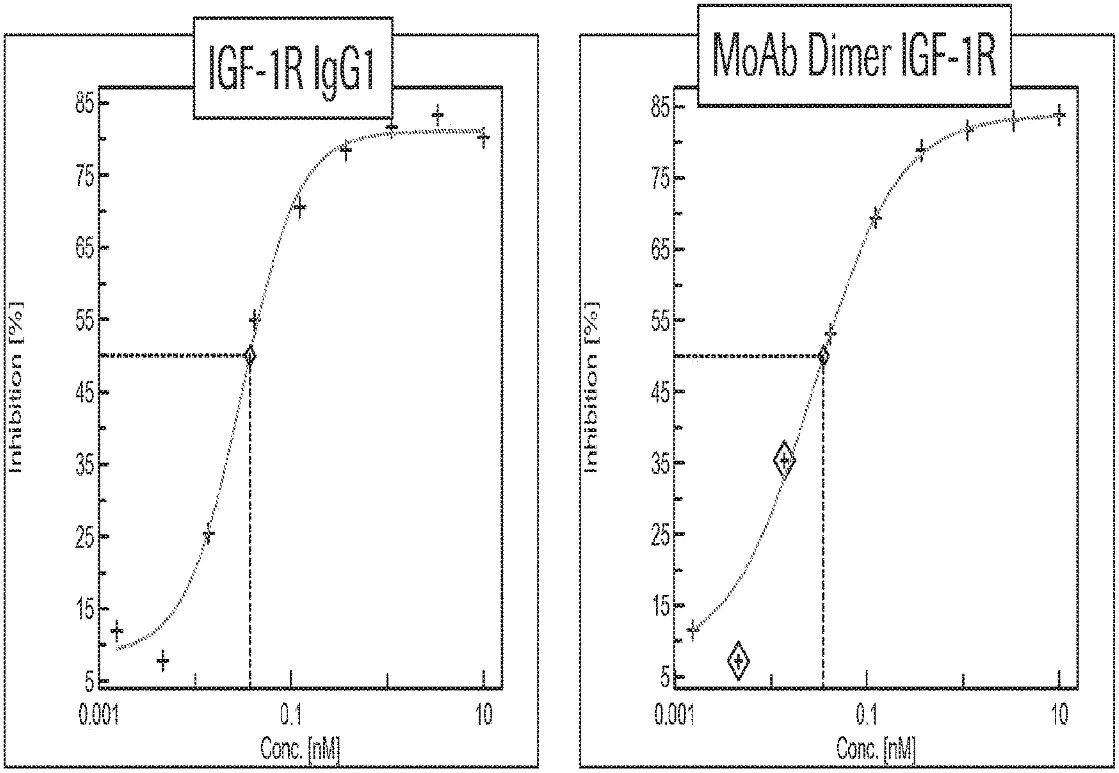

FIG. 8: Internalization of IGF-1R was assessed in HT29 cells following incubation with IGF-1R IgG1 (Mab IGF-1R) antibody and IGF-1R MoAb-Dimer (IGF 1R AK18 MoAb-Dimer ("CH3-wt")). The graph depicts total IGF-1R levels upon antibody exposure which were determined in an ELISA-based assay setup.

Figure 9:
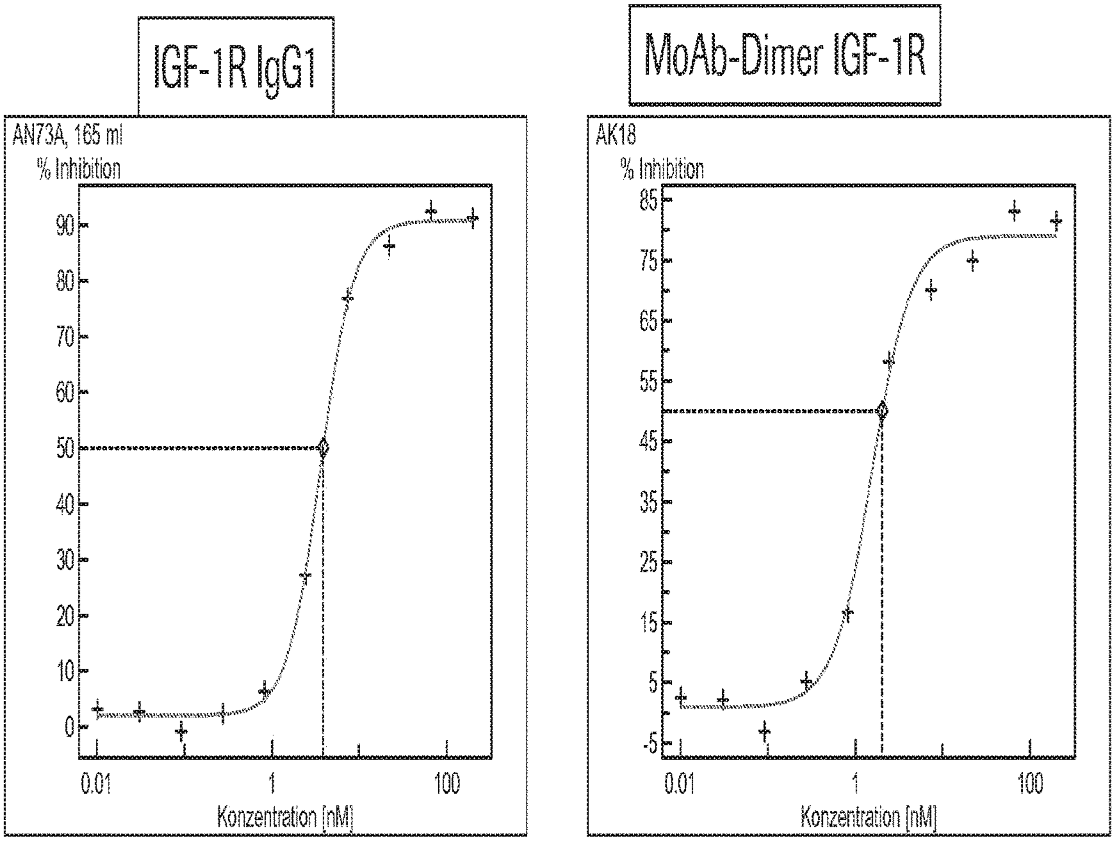
Figures 10A, 10B, 10C, 10D, 10E, 10F, 10G, 10H:
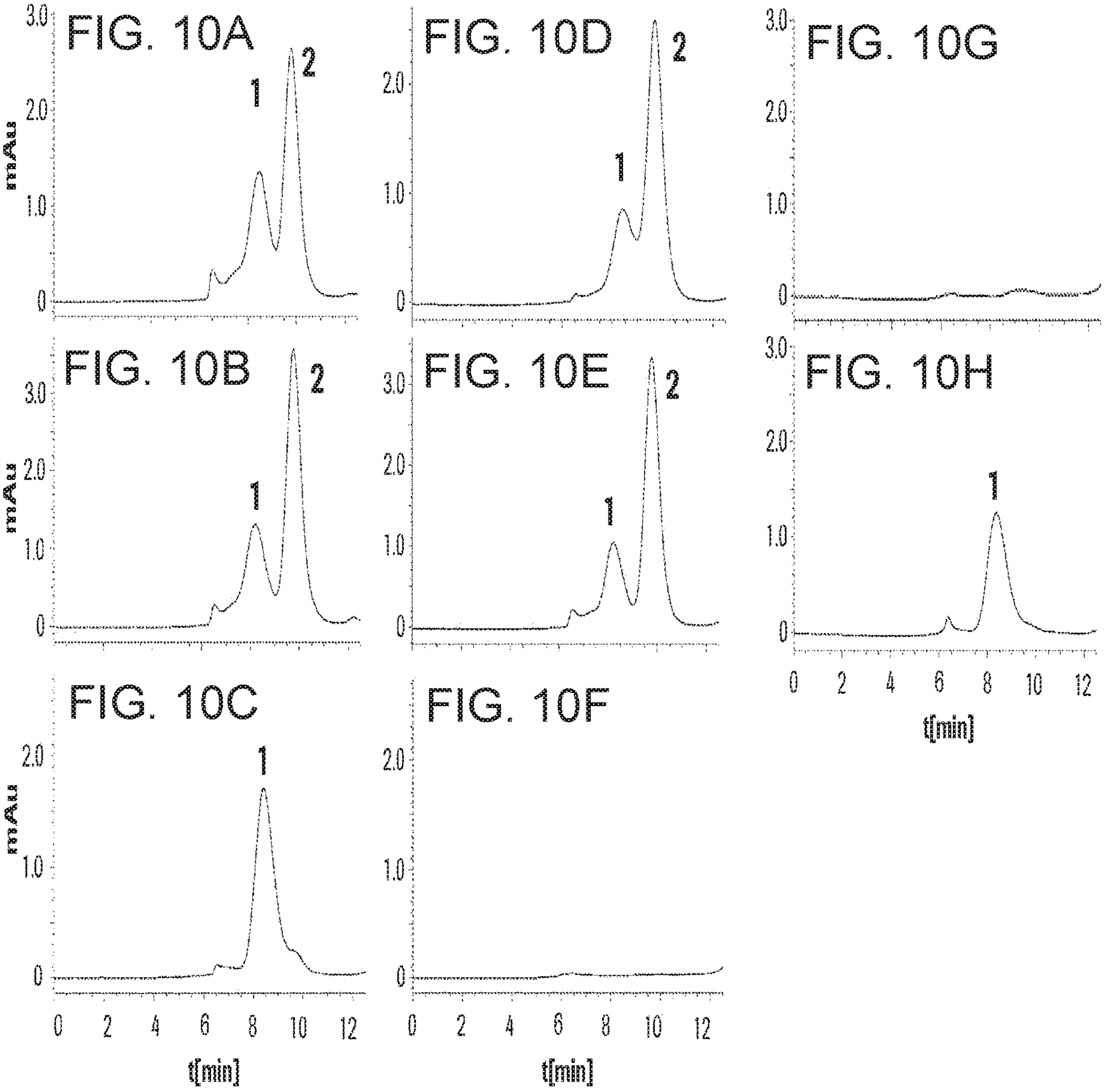

FIG. 9: Autophosphorylation of IGF-1R was assessed following incubation of 3T3-IGF-1R cells with IGF-1R IgG1 antibody and IGF-1R MoAb-Dimer (IGF1R AK18 MoAb-Dimer ("CH3-wt")) in the presence of 10 nM IGF-1. The graph depicts phospho IGF-1R levels upon antibody exposure which were determined in an ELISA-based assay setup.

FIGS. 10A-10H: Analysis of obtained MoAb-Dimer (=antigen binding protein according to the invention) versus MoAb-monomer (=monovalent byproduct) ratios as determined by HPLC. Different antibody with wild type CH3 (CH3-wt) domains and modified CH3 domains were transiently expressed and the ratios of dimer versus monomer determined.

Figure 11:
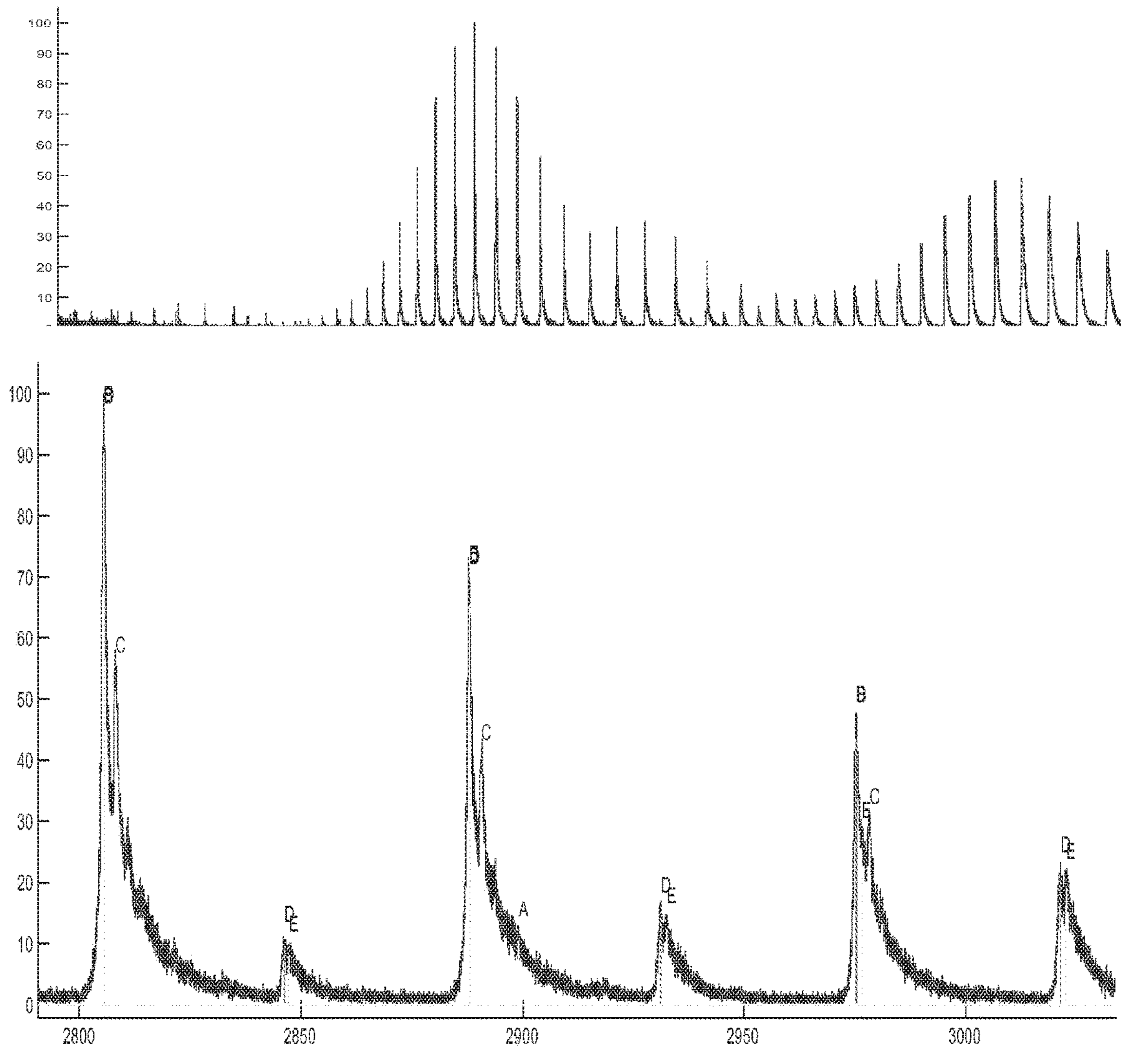
Figure 12:
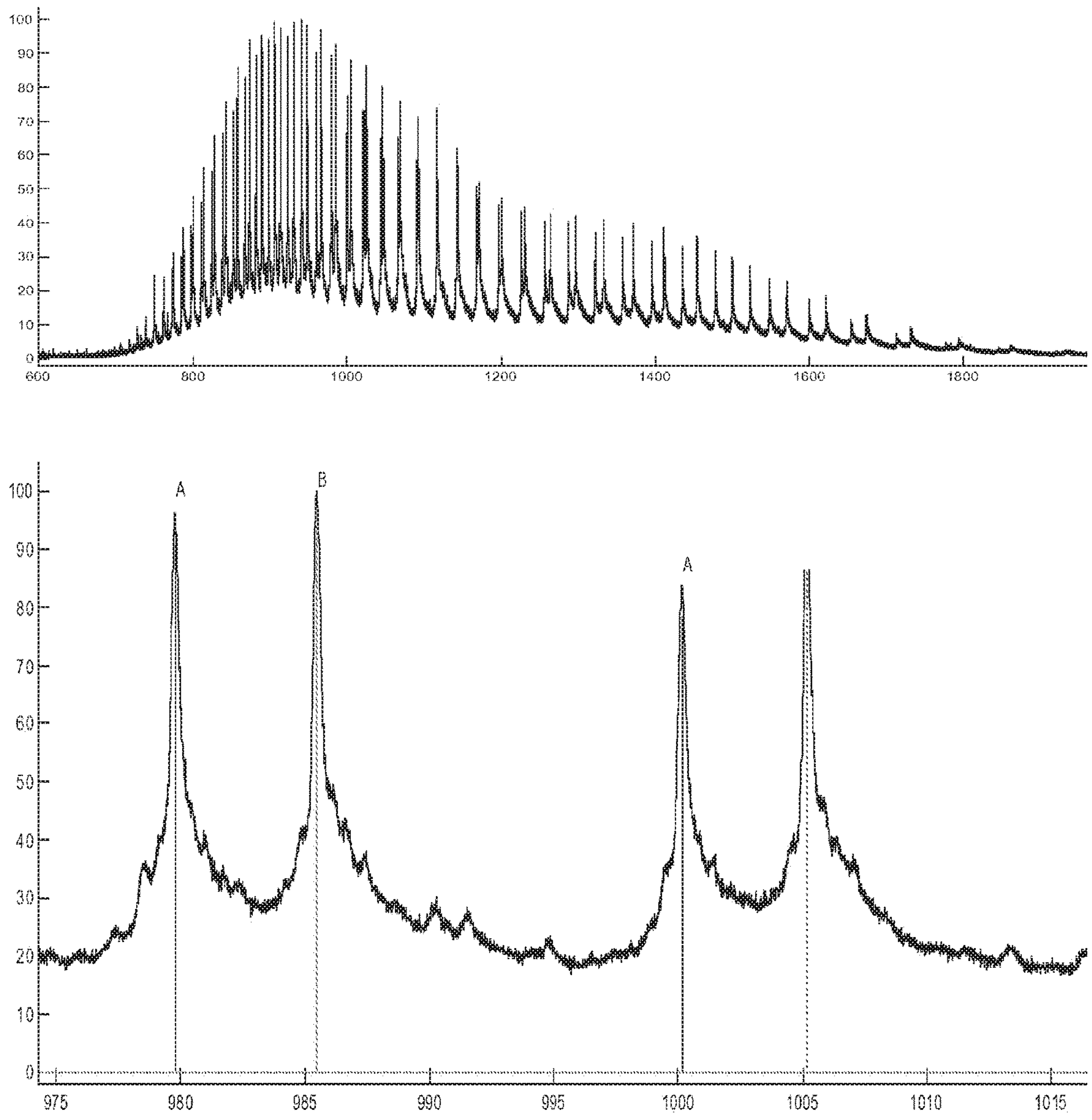

FIG. 11: ESI-MS spectrum of the IGF-1R MoAb Dimer (SEC fraction 1) under non reducing condition and after deglycosylation FIG. 12: ESI-MS spectrum of the IGF-1R MoAb Dimer (SEC fraction 1) after degylcosylation and reduction.

DETAILED DESCRIPTION OF THE INVENTION

The invention comprises an antigen binding protein comprising a) two modified heavy chains of an antibody which specifically binds to an antigen, wherein VH of each heavy chain is replaced by the VL of said antibody, said modified heavy chains being associated with each other via their CH domains of the Fc part;

b) two modified heavy chains of said antibody wherein CHI of each heavy chain is replaced by CL of said antibody, said modified heavy chains being associated with each other via their CH domains of the Fc part;

and wherein the VL domains of the heavy chains of a) are associated with the VH domains of the heavy chains of b), and the CH1 domains of the heavy chains of a) are associated with the CL domains of the heavy chains of b).

In one embodiment the antigen binding protein according to the invention is characterized in that the CH3 domains of the Fc part of the modified heavy chains of a) and the CH3 domains of the Fc part of the modified heavy chains of b) are of the same isotype.

In one embodiment the antigen binding protein according to the invention is characterized in that the CH2 and CH3 domains of the Fc part of the modified heavy chains of a) and the CH2 and CH3 domains of the Fc part of the modified heavy chains of b) are of the same isotype.

In one embodiment the antigen binding protein according to the invention is characterized in that the CH2 and CH3 domains of the Fc part of the modified heavy chains of a) and the CH2 and CH3 domains of the Fc part of the modified heavy chains of b) are of the IgG isotype.

In one embodiment the antigen binding protein according to the invention is characterized in that the CH2 and CH3 domains of the Fc part of the modified heavy chains of a) and the CH2 and CH3 domains of the Fc part of the modified heavy chains of b) are of the IgG1 isotype.

In one embodiment the antigen binding protein according to the invention is characterized in comprising a) two modified heavy chains comprising the amino acid sequence of SEQ ID NO:1; and b) two modified heavy chains comprising the amino acid sequence of SEQ ID NO:2;

a) two modified heavy chains comprising the amino acid sequence of SEQ ID NO:3; and b) two modified heavy chains comprising the amino acid sequence of SEQ ID NO:4; or a) two modified heavy chains comprising the amino acid sequence of SEQ ID NO:5; and b) two modified heavy chains comprising the amino acid sequence of SEQ ID NO:6.

To improve the yields of the antigen binding protein according to the invention (i.e. to improve MoAb dimer over MoAb monomer ratio (see Example 9)), the IgG1 CH3 domains of a) can be modified further by mutations so that the IgG1 CH3 domains of a) and the natural (wt) IgG1 CH3 domains of b) differ. The modification/mutation has to be carried out in a way to maintain attractive interactions between identical chains but lead to repulsion of different chains (see also FIG. 1C).

In one embodiment the antigen binding protein according to the invention is characterized in that either the two modified heavy chains of a), or the two modified heavy chains of b), are further modified by the amino acid substitutions S364G, L368F, D399K and K409D (wherein the amino acid positions are numbered according to the EU index of Kabat).

The EU Index numbering system of Kabat is described in Kabat, et al., Sequences of Proteins of Immunological Interest, 5th ed., Public Health Service, National Institutes of Health, Bethesda, Md. (1991).

In one embodiment the antigen binding protein according to the invention is characterized in that a) two modified heavy chains comprising the amino acid sequence of SEQ ID NO:1; and b) two modified heavy chains comprising the amino acid sequence of SEQ ID NO:2;

wherein either the two modified heavy chains of a), or the two modified heavy chains of b), are further modified by the amino acid substitutions S364G, L368F, D399K and K409D (wherein the amino acid positons are numbered according to the EU Index of Kabat);

a) two modified heavy chains comprising the amino acid sequence of SEQ ID NO:3; and b) two modified heavy chains comprising the amino acid sequence of SEQ ID NO:4;

wherein either the two modified heavy chains of a), or the two modified heavy chains of b), are further modified by the amino acid substitutions S364G, L368F, D399K and K409D (wherein the amino acid positions are numbered according to the EU Index of Kabat);

or a) two modified heavy chains comprising the amino acid sequence of SEQ ID NO:5; and b) two modified heavy chains comprising the amino acid sequence of SEQ ID NO:6;

wherein either the two modified heavy chains of a), or the two modified heavy chains of b), are further modified by the amino acid substitutions S364G, L368F, D399K and K409D (wherein the amino acid positons are numbered according to the EU Index of Kabat).

Another possibility to improve the yields of the antigen binding protein according to the invention (i.e. to improve MoAb dimer over MoAb monomer ratio (see Example 9)), the CH3 domains of a) and b) are taken from different isotypes. Thus the attractive interactions between identical chains are maintained but different chains are repulsed (see also FIG. 1C).

Therefore in one embodiment the antigen binding protein according to the invention is characterized in that the CH3 domains of the Fc part of the modified heavy chains of a) and the CH3 domains of the Fc part of the modified heavy chains of b) are of a different isotype.

In one embodiment the antigen binding protein according to the invention is characterized in that the CH3 domains of the Fc part of the modified heavy chains of a) are of the IgG isotype;

and the CH3 domains of the Fc part of the modified heavy chains of b) are of the IgA isotype.

In one embodiment the antigen binding protein according to the invention is characterized in comprising a) two modified heavy chains comprising the amino acid sequence of SEQ ID NO:7; and b) two modified heavy chains comprising the amino acid sequence of SEQ ID NO:4.

In one embodiment the antigen binding protein according to the invention is characterized in comprising a) two modified heavy chains comprising the amino acid sequence of SEQ ID NO:3; and b) two modified heavy chains comprising the amino acid sequence of SEQ ID NO:8.

In one embodiment the antigen binding protein according to the invention is characterized in that The CH2 and CH3 domains of the Fc part of the modified heavy chains of a) are of the IgG1 isotype;

and the CH2 and CH3 domains of the Fc part of the modified heavy chains of b) are of the IgA1 isotype.

In one embodiment the antigen binding protein according to the invention is characterized in that in that the CH2 domain of the Fc parts of a) and b) are of IgG1 isotype, and the antigen binding protein is afucosylated with an amount of fucose of 80% or less of the total amount of oligosaccharides (sugars) at Asn297 is of human IgG1 isotype.

The term "antibody" as used herein denotes a full length antibody consisting of two antibody heavy chains and two antibody light chains (see FIG. 1). A heavy chain of full length antibody is a polypeptide consisting in N-terminal to C-terminal direction of an antibody heavy chain variable domain (VH), an antibody constant heavy chain domain 1 (CH1), and antibody hinge region (HR), an antibody heavy chain constant domain 2 (CH2), and an antibody heavy chain constant domain 3 (CH3), abbreviated as VH—CH1-HR—CH2-CH3; and optionally an antibody heavy chain constant domain 4 (CH4) in case of an antibody of the class IgE. Preferably the heavy chain of full length antibody is a polypeptide consisting in N-terminal to C-terminal direction of VH, CH1, HR, CH2 and CH3. The light chain of full length antibody is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The antibody chains are linked together via inter-polypeptide disulfide bonds between the CL domain and the CH1 domain (i.e. between the light and heavy chain) and between the hinge regions of the full length antibody heavy chains. Examples of typical full length antibodies are natural antibodies like IgG (e.g. IgG1 and IgG2), IgM, IgA, IgD, and IgE). The antibodies according to the invention can be from a single species e.g. human, or they can be chimerized or humanized antibodies. The full length antibodies according to the invention comprise two antigen binding sites each formed by a pair of VH and VL, which both specifically bind to the same (first) antigen.

From these full length antibodies the antigen binding protein of the invention is derived by:

a) modifying two heavy chains of an antibody which specifically binds to an antigen, by replacing the VH domain of each heavy chain by the VL domain of said antibody;

b) modifying two heavy chains of said antibody by replacing the CH1 domain of each heavy chain by the CL domain of said antibody.

The "Fc part" of an antibody or antigen binding protein is not involved directly in binding of an antibody to an antigen, but is responsible a) for the association of the (modified) antibody chains with each other (e.g., via their CH3 domains) and b) for various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively.

There are five types of mammalian antibody heavy chains denoted by the Greek letters: α, δ, ε, γ, and μ (Janeway, C. A., Jr. et al., Immunobiology, 5th ed., Garland Publishing (2001)). The type of heavy chain present defines the class of antibody; these chains are found in IgA, IgD, IgE, IgG, and IgM antibodies, respectively (Rhoades, R. A., and Pflanzer, R. G., Human Physiology, 4th ed., Thomson Learning (2002)). Distinct heavy chains differ in size and composition; α and γ contain approximately 450 amino acids, while μ and ε have approximately 550 amino acids.

Each heavy chain has two regions, the constant region and the variable region. The constant region is identical in all antibodies of the same isotype, but differs in antibodies of different isotype. Heavy chains γ, α and δ have a constant region composed of three constant domains CH1, CH2, and CH3 (in a line), and a hinge region for added flexibility (Woof, J., and Burton, D., Nat. Rev. Immunol. 4 (2004) 89-99); heavy chains μ and ε have a constant region composed of four constant domains CH1, CH2, CH3, and CH4 (Janeway, C. A., Jr. et al., Immunobiology, 5th ed., Garland Publishing (2001)). The variable region of the heavy chain differs in antibodies produced by different B cells, but is the same for all antibodies produced by a single B cell or B cell clone. The variable region of each heavy chain is approximately 110 amino acids long and is composed of a single antibody domain.

The "CH domains of the Fc part" are the antibody heavy chain constant domain 2 (CH2), and the antibody heavy chain constant domain 3 (CH3), and optionally the antibody heavy chain constant domain 4 (CH4) in case of an antibody of the class IgE.

The term "said modified heavy chains being associated with each other via their CH domains of the Fc part" refers to the interchain domain pairing of the antibody heavy chain constant domains (CH) of the two modified heavy chains with each other e.g. the two CH3 domains of both chains with each other via e.g. interchain ionic interaction, Van-Der Waals interaction, or hydrogen bonding (see FIG. 1A). In one embodiment said modified heavy chains are associated with each other via at least their CH3 domains of the Fc part (and optionally via their CH2 domains, or optionally via their CH2 domains and CH4 domains (if present)).

The term "wherein the VL domains of the heavy chains of a) are associated with the VH domains of the heavy chains of b), and the CH1 domains of the heavy chains of a) are associated with the CL domains of the heavy chains of b)" refers to the domain pairing of said antibody domains (always one of a) and one of b)) as found e.g. in natural antibodies (VL/VH and CH1/CL) e.g. via interchain ionic interaction, Van-Der Waals interaction, hydrogen bonding, or disulfide interaction. (see FIG. 1A).

The "antigen binding protein" according to the invention comprises two antigen-binding sites and is bivalent. The terms "binding site" or "antigen-binding site" as used herein denotes the region(s) of antigen binding protein according to the invention to which a ligand (e.g. the antigen or antigen fragment of it) actually binds and which is derived from antibody molecule or a fragment thereof (e.g. a Fab fragment). The antigen-binding site according to the invention comprise an antibody heavy chain variable domains (VH) and an antibody light chain variable domains (VL).

The antigen-binding sites (i.e. the pairs of VH/VL) that specifically bind to the desired antigen can be derived a) from known antibodies to the antigen or b) from new antibodies or antibody fragments obtained by de novo immunization methods using inter alia either the antigen protein or nucleic acid or fragments thereof or by phage display.

An antigen-binding site of a antigen binding protein of the invention contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

Antibody specificity refers to selective recognition of the antibody for a particular epitope of an antigen. Natural antibodies, for example, are monospecific. Bispecific antibodies are antibodies which have two different antigen-binding specificities. The antigen binding proteins according to the invention are at least monospecific and specifically bind to an epitope of the respective antigen.

The term "valent" as used within the current application denotes the presence of a specified number of binding sites in an antibody molecule. A natural antibody for example has two binding sites and is bivalent. Also the antigen binding protein according to the invention is at least bivalent.

The terms "monoclonal antibody" or "monoclonal antibody composition" as used herein refer to a preparation of antibody molecules of a single amino acid composition.

The term "chimeric antibody" refers to an antibody comprising a variable regions, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole, et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NSO or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, et al., Sequences of Proteins of Immunological Interest, 5th ed., Public Health Service, National Institutes of Health, Bethesda, Md. (1991).

As used herein, the term "binding" or "specifically binding" refers to the binding of the antigen binding protein to an epitope of the antigen in an in vitro assay, preferably in an plasmon resonance assay (BIACORE®, GE-Healthcare Uppsala, Sweden) with purified wild-type antigen. The affinity of the binding is defined by the terms ka (rate constant for the association of the antibody from the antibody/antigen complex), $k_D$ (dissociation constant), and $K_D$ ($k_D$/ka). Binding or specifically binding means a binding affinity (KD) of $10^{-8}$ mol/l or less (e.g. $10^{-8}$ M to $10^{-13}$ mol/l), preferably $10^{-9}$ M to $10^{-13}$ mol/l. Thus, a antigen binding protein according to the invention is specifically binding to each antigen for which it is specific with a binding affinity ($K_D$) of $10^{-8}$ mol/l or less (e.g. $10^{-8}$ M to $10^{-13}$ mol/l), preferably $10^{-9}$ M to $10^{-13}$ mol/l.

Binding of the antigen binding protein to the FcγRIII can be investigated by a BIACORE® assay (GE-Healthcare Uppsala, Sweden). The affinity of the binding is defined by the terms ka (rate constant for the association of the antibody from the antibody/antigen complex), $k_D$ (dissociation constant), and $K_D$ ($k_D$/ka).

The term "epitope" includes any polypeptide determinant capable of specific binding to a antigen binding proteins. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by a antigen binding protein.

In certain embodiments, an antibody is said to specifically bind an antigen when it preferentially recognizes its target antigen in a complex mixture of proteins and/or macromolecules.

The term "constant region" as used within the current applications denotes the sum of the domains of an antibody other than the variable region. The constant region is not involved directly in binding of an antigen, but exhibits various effector functions. Depending on the amino acid sequence of the constant region of their heavy chains, antibodies are divided in the classes (also named isotypes): IgA, IgD, IgE, IgG and IgM, and several of these may be further divided into subclasses (also named isotypes), such as IgG1, IgG2, IgG3, and IgG4, IgA1 and IgA2. The heavy chain constant regions that correspond to the different classes of antibodies are called α, δ, ε, γ, and μ, respectively. The light chain constant regions (CL) which can be found in all five antibody classes are called κ (kappa) and λ (lambda).

The term "constant region derived from human origin" as used in the current application denotes a constant heavy chain region of a human antibody of the isotypes IgG1, IgG2, IgG3, or IgG4 and/or a constant light chain kappa or lambda region. Such constant regions are well known in the state of the art and e.g. described by Kabat, E. A., (see e.g. Johnson, G. and Wu, T. T., Nucleic Acids Res. 28 (2000) 214-218; Kabat, E. A., et al., Proc. Natl. Acad. Sci. USA 72 (1975) 2785-2788).

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

While antibodies of the IgG4 subclass show reduced Fc receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment an antibody according to the invention has a reduced FcR binding compared to an IgG1 antibody and the full length parent antibody is in regard to FcR binding of IgG4 subclass or of IgG1 or IgG2 subclass with a mutation in S228, L234, L235 and/or D265, and/or contains the PVA236 mutation. In one embodiment the mutations in the full length parent antibody are S228P, L234A, L235A, L235E and/or PVA236. In another embodiment the mutations in the full length parent antibody are in IgG4 S228P and L235E and in IgG1 L234A and L235A.

The constant region of an antibody is directly involved in ADCC (antibody-dependent cell-mediated cytotoxicity) and CDC (complement-dependent cytotoxicity). Complement activation (CDC) is initiated by binding of complement factor C1q to the constant region of most IgG antibody subclasses. Binding of C1q to an antibody is caused by defined protein-protein interactions at the so called binding site. Such constant region binding sites are known in the state of the art and described e.g. by Lukas, T. J., et al., J. Immunol. 127 (1981) 2555-2560; Bunkhouse, R. and Cobra, J. J., Mol. Immunol. 16 (1979) 907-917; Burton, D. R., et al., Nature 288 (1980) 338-344; Thomason, J. E., et al., Mol. Immunol. 37 (2000) 995-1004; Idiocies, E. E., et al., J. Immunol. 164 (2000) 4178-4184; Hearer, M., et al., J. Virol. 75 (2001) 12161-12168; Morgan, A., et al., Immunology 86 (1995) 319-324; and EP 0 307 434. Such constant region binding sites are, e.g., characterized by the amino acids L234, L235, D270, N297, E318, K320, K322, P331, and P329 (numbering according to EU index of Kabat which is described in Kabat, et al., Sequences of Proteins of Immunological Interest, 5th ed., Public Health Service, National Institutes of Health, Bethesda, Md. (1991)).

The term "antibody-dependent cellular cytotoxicity (ADCC)" refers to lysis of human target cells by an antibody according to the invention in the presence of effector cells. ADCC is measured preferably by the treatment of a preparation of antigen expressing cells with an antibody according to the invention in the presence of effector cells such as freshly isolated PBMC or purified effector cells from buffy coats, like monocytes or natural killer (NK) cells or a permanently growing NK cell line.

Surprisingly it has been found that an antigen binding protein according to the invention shows enhanced ADCC properties compared to its parent full length antibody, especially in the area of higher antibody concentrations. These improved ADCC effects are achieved without further modification of the Fc part like glycoengineering.

Thus in one embodiment the antigen binding proteins according to the invention have an enhanced ADCC (measured as described in Example 4) compared to its parent full length antibody.

In mammals there are only two types of light chain, which are called lambda (λ) and kappa (κ). A light chain has two successive domains: one constant domain CL and one variable domain VL. The approximate length of a light chain is 211 to 217 amino acids. Preferably the light chain is a kappa (κ) light chain, and the constant domain CL is preferably derived from a kappa (κ) light chain (the constant domain Cκ).

Cell-mediated effector functions of monoclonal antibodies can be e.g. further enhanced by engineering their oligosaccharide component as described in Umana, P., et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M., R., et al., Glycobiology 5 (1995) 813-822; Jefferis, R., et al., Immunol. Rev. 163 (1998) 59-76; Wright, A., and Morrison, S., L., Trends Biotechnol. 15 (1997) 26-32). Umana, P., et al. Nature Biotechnol. 17 (1999) 176-180 and WO 99/54342 showed that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1q (Umana, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R., L., et al., J. Biol. Chem. 276 (2001) 6591-6604; Shields, R., L., et al., J. Biol. Chem. 277 (2002) 26733-26740; Simmons, L., C., et al., J. Immunol. Methods 263 (2002) 133-147).

In one aspect of the invention the antigen binding protein according to the invention is characterized in that the CH2 domains of the Fc parts of a) and b) are of IgG1 isotype, and the antigen binding protein is afucosylated with an amount of fucose of 80% or less of the total amount of oligosaccharides (sugars) at Asn297.

In one embodiment antigen binding protein is afucosylated with and the amount of fucose of 65% to 5% of the total amount of oligosaccharides (sugars) at Asn297.

The term "afucosylated antigen binding protein" refers to an antigen binding proteins of IgG1 or IgG3 isotype (preferably of IgG1 isotype) with an altered pattern of glycosylation in the Fc region at Asn297 having a reduced level of fucose residues. Glycosylation of human IgG1 or IgG3 occurs at Asn297 as core fucosylated bianntennary complex oligosaccharide glycosylation terminated with up to 2 Gal residues. These structures are designated at G0, G1 (α1,6 or α1,3) or G2 glycan residues, depending from the amount of terminal Gal residues (Raju, T. S., BioProcess Int. 1 (2003) 44-53). CHO type glycosylation of antibody Fc parts is e.g. described by Routier, F. H., Glycoconjugate J. 14 (1997) 201-207. Antibodies which are recombinantely expressed in non glycomodified CHO host cells usually are fucosylated at Asn297 in an amount of at least 85%. It should be understood that the term "antigen binding protein" as used herein includes an antigen binding protein having no fucose in its glycosylation pattern. It is commonly known that typical glycosylated residue position in an antibody is the asparagine at position 297 according to the EU numbering system ("Asn297").

Thus an afucosylated antigen binding protein according to the invention means an antigen binding protein of IgG1 or IgG3 isotype (preferably of IgG1 isotype) wherein the amount of fucose is 80% or less (e.g., of 80% to 1%) of the total amount of oligosaccharides (sugars) at Asn297 (which means that at least 20% or more of the oligosaccharides of the Fc region at Asn297 are afucosylated). In one embodiment the amount of fucose is 65% or less (e.g., of 65% to 1%), in one embodiment from 65% to 5%, in one embodiment from 40% to 20% of the oligosaccharides of the Fc region at Asn297. According to the invention "amount of fucose" means the amount of said oligosaccharide (fucose) within the oligosaccharide (sugar) chain at Asn297, related to the sum of all oligosaccharides (sugars) attached to Asn 297 (e.g. complex, hybrid and high mannose structures) measured by MALDI-TOF mass spectrometry and calculated as average value (for a detailed procedure to determine the amount of fucose, see e.g. WO 2008/077546). Furthermore in one embodiment, the oligosaccharides of the Fc region are bisected. The afucosylate antigen binding protein according to the invention can be expressed in a glycomodified host cell engineered to express at least one nucleic acid encoding a polypeptide having GnTIII activity in an amount sufficient to partially fucosylate the oligosaccharides in the Fc region. In one embodiment, the polypeptide having GnTIII activity is a fusion polypeptide. Alternatively α1,6-fucosyltransferase activity of the host cell can be decreased or eliminated according to U.S. Pat. No. 6,946,292 to generate glycomodified host cells. The amount of antigen binding protein fucosylation can be predetermined e.g. either by fermentation conditions (e.g. fermentation time) or by combination of at least two antigen binding protein with different fucosylation amount. Such methods to generate afucosylated antigen binding proteins are described in WO 2005/044859, WO 2004/065540, WO 2007/03187, Umana, P., et al., Nature Biotechnol. 17 (1999) 176-180, WO 99/154342, WO 2005/018572, WO 2006/116260, WO 2006/114700, WO 2005/011735, WO 2005/027966, WO 97/028267, US 2006/0134709, US 2005/0054048, US 2005/0152894, WO 2003/035835, WO 2000/061739. These glycoengineered antigen binding proteins according to the invention have an increased ADCC (compared to the parent antigen binding proteins). Other glycoengineering methods yielding afucosylated antigen binding proteins according to the invention are described e.g. in Niwa, R., et al., J. Immunol. Methods 306 (2005) 151-160; Shinkawa, T., et al., J. Biol. Chem, 278 (2003) 3466-3473; WO 03/055993 or US 2005/0249722.

Thus one aspect of the invention is an afucosylated antigen binding protein according to the invention which is of IgG1 isotype or IgG3 isotype (preferably of IgG1 isotype) with an amount of fucose of 60% or less (e.g. of 60% to 1%) of the total amount of oligosaccharides (sugars) at Asn297.

Thus one aspect of the invention is an afucosylated antigen binding protein according to the invention which is of IgG1 isotype or IgG3 isotype (preferably of IgG1 isotype) with an amount of fucose of 60% or less (e.g. of 60% to 1%) of the total amount of oligosaccharides (sugars) at Asn297 for the treatment of cancer.

Another aspect of the invention is the use of invention an afucosylated antigen binding protein according to the invention which is of IgG1 or IgG3 isotype (preferably of IgG1 isotype) with an amount of fucose of 60% or less of the total amount of oligosaccharides (sugars) at Asn297, for the manufacture of a medicament for the treatment of cancer.

In one embodiment the amount of fucose is between 60% and 20% of the total amount of oligosaccharides (sugars) at Asn297. In one embodiment the amount of fucose is between 60% and 40% of the total amount of oligosaccharides (sugars) at Asn297. In one embodiment the amount of fucose is between 0% of the total amount of oligosaccharides (sugars) at Asn297.

The "EU numbering system" or "EU index" is generally used when referring to a residue in an immunoglobulin heavy chain constant region (e.g., the EU index reported in Kabat et al., Sequences of Proteins of Immunological Interest, 5th ed., Public Health Service, National Institutes of Health, Bethesda, Md. (1991) expressly incorporated herein by reference).

The term "the sugar chains show characteristics of N-linked glycans attached to Asn297 of an antibody recombinantly expressed in a CHO cell" denotes that the sugar chain at Asn297 of the full length parent antibody according to the invention has the same structure and sugar residue sequence except for the fucose residue as those of the same antibody expressed in unmodified CHO cells, e.g. as those reported in WO 2006/103100.

The term "NGNA" as used within this application denotes the sugar residue N-glycolylneuraminic acid.

Glycosylation of human IgG1 or IgG3 occurs at Asn297 as core fucosylated biantennary complex oligosaccharide glycosylation terminated with up to two Gal residues. Human constant heavy chain regions of the IgG1 or IgG3 subclass are reported in detail by Kabat, E., A., et al., Sequences of Proteins of Immunological Interest, 5th Ed. Public Health Service, National Institutes of Health, Bethesda, Md. (1991), and by Brueggemann, M., et al., J. Exp. Med. 166 (1987) 1351-1361; Love, T., W., et al., Methods Enzymol. 178 (1989) 515-527. These structures are designated as G0, G1 (α-1,6- or α-1,3-), or G2 glycan residues, depending from the amount of terminal Gal residues (Raju, T., S., Bioprocess Int. 1 (2003) 44-53). CHO type glycosylation of antibody Fc parts is e.g. described by Routier, F. H., Glycoconjugate J. 14 (1997) 201-207. Antibodies which are recombinantly expressed in non-glycomodified CHO host cells usually are fucosylated at Asn297 in an amount of at least 85%. The modified oligosaccharides of the full length parent antibody may be hybrid or complex. Preferably the bisected, reduced/not-fucosylated oligosaccharides are hybrid. In another embodiment, the bisected, reduced/not-fucosylated oligosaccharides are complex.

According to the invention "amount of fucose" means the amount of said sugar within the sugar chain at Asn297, related to the sum of all glycostructures attached to Asn297 (e.g. complex, hybrid and high mannose structures) measured by MALDI-TOF mass spectrometry and calculated as average value. The relative amount of fucose is the percentage of fucose-containing structures related to all glycostructures identified in an N-Glycosidase F treated sample (e.g. complex, hybrid and oligo- and high-mannose structures, resp.) by MALDI-TOF.

The antibody according to the invention is produced by recombinant means. Thus, one aspect of the current invention is a nucleic acid encoding the antibody according to the invention and a further aspect is a cell comprising said nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NSO cells, SP2/0 cells, HEK293 cells, COS cells, PER.C6 cells, yeast, or *E. coli* cells, and the antibody is recovered from the cells (supernatant or cells after lysis). General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antigen binding proteins according to the invention are suitably separated from the culture medium by conventional immunoglobulin purification procedures such as, for example, protein A SEPHAROSE® (crosslinked beaded form of agarose), hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA.

Amino acid sequence variants (or mutants) of the antigen binding protein are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Expression in NSO cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of antigen binding proteins is performed in order to eliminate cellular components or other contaminants, e.g. other cellular nucleic acids or proteins (e.g. byproducts of FIG. 1B), by standard techniques, including alkaline/SDS treatment, CsCl banding, column chromatography, agarose gel electrophoresis, and others well known in the art (see Ausubel, F., et al., ed. Current Protocols in Molecular Biology, Greene Publishing and Wiley Interscience, New York (1987)). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophneylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102). One example of a purification is described in Example 1 and the corresponding Figures.

One aspect of the invention is a pharmaceutical composition comprising an antigen binding protein according to the invention. Another aspect of the invention is the use of an antigen binding protein according to the invention for the manufacture of a pharmaceutical composition. A further aspect of the invention is a method for the manufacture of a pharmaceutical composition comprising an antigen binding protein according to the invention. In another aspect, the present invention provides a composition, e.g. a pharmaceutical composition, containing an antigen binding protein according to the present invention, formulated together with a pharmaceutical carrier.

One embodiment of the invention is the antigen binding protein according to the invention for the treatment of cancer.

Another aspect of the invention is said pharmaceutical composition for the treatment of cancer.

One embodiment of the invention is the antigen binding protein according to the invention for use in the treatment of cancer.

Another aspect of the invention is the use of an antigen binding protein according to the invention for the manufacture of a medicament for the treatment of cancer.

Another aspect of the invention is method of treatment of patient suffering from cancer by administering an antigen binding protein according to the invention to a patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A pharmaceutical composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham and Van der Eh, Virology 52 (1978) 546. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, F. N, et al., PNAS 69 (1972) 7110).

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The following examples, sequence listing and figures are provided to aid the understanding of the present invention, the true scope of which is set forth in the appended claims. It is understood that modifications can be made in the procedures set forth without departing from the spirit of the invention.

Description of the Amino Acid Sequences

SEQ ID NO:1 c-Met 5D5 MoAb-Dimer ("CH3-wt")-modified heavy chain a) VL-CH1-CH2-CH3

SEQ ID NO:2 c-Met 5D5 MoAb-Dimer ("CH3-wt")-modified heavy chain b) VH—CL-CH2-CH3

SEQ ID NO:3 IGF1R AK18 MoAb-Dimer ("CH3-wt")-modified heavy chain a) VL-CH1-CH2-CH3

SEQ ID NO:4 IGF1R AK18 MoAb-Dimer ("CH3-wt")-modified heavy chain b) VH—CL-CH2-CH3

SEQ ID NO:5 Her3 205 MoAb-Dimer ("CH3-wt")-modified heavy chain a) VL-CH1-CH2-CH3

SEQ ID NO:6 Her3 205 MoAb-Dimer ("CH3-wt")-modified heavy chain b) VH—CL-CH2-CH3

SEQ ID NO:7 IGF1R AK18 MoAb-Dimer—modified heavy chain a) VL-CH1-CH2-CH3 with IgA-CH3

SEQ ID NO:8 IGF1R AK18 MoAb-Dimer—modified heavy chain b) VH—CL-CH2-CH3 with IgA-CH3 domain

EXAMPLES

The present invention is described in further detain in the following examples which are not in any way intended to limit the scope of the invention as claimed. All references cited are herein specifically incorporated by reference for all that is described therein. The following examples are offered to illustrate, but not to limit the claimed invention.

Experimental Procedure

A. Material and Methods

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y. (1989). The molecular biological reagents were used according to the manufacturer's instructions.

DNA and Protein Sequence Analysis and Sequence Data Management

General information regarding the nucleotide sequences of human immunoglobulins light and heavy chains is given in: Kabat, E. A. et al., (1991) Sequences of Proteins of Immunological Interest, Fifth Ed., NIH Publication No 91-3242. Amino acids of antibody chains are numbered according to EU numbering (Edelman, G. M., et al., PNAS 63 (1969) 78-85; Kabat, E. A., et al., (1991) Sequences of Proteins of Immunological Interest, Fifth Ed., NIH Publication No 91-3242). The GCG's (Genetics Computer Group, Madison, Wis.) software package version 10.2 and Infomax's Vector NTI Advance suite version 8.0 was used for sequence creation, mapping, analysis, annotation and illustration.

DNA Sequencing

DNA sequences were determined by double strand sequencing performed at SequiServe (Vaterstetten, Germany) and Geneart AG (Regensburg, Germany).

Gene Synthesis

Desired gene segments were prepared by Geneart AG (Regensburg, Germany) from synthetic oligonucleotides and PCR products by automated gene synthesis. The gene segments which are flanked by singular restriction endonuclease cleavage sites were cloned into pGA18 (ampR) plasmids. The plasmid DNA was purified from transformed bacteria and concentration determined by UV spectroscopy. The DNA sequence of subcloned gene fragments was confirmed by DNA sequencing. DNA sequences encoding for the two antibody chains (VH—CL-CH2-CH3 and VL-CH1-CH2-CH3) were prepared as whole fragments by gene synthesis with flanking 5'HpaI and 3'NaeI restriction sites. Gene segments coding for point mutations in the CH3 domain which preferentially lead to the MoAb-Dimer product as well as the replacement of gene segments coding for IgG1 part with an IgA-CH3 domain (e.g. SEQ. ID. NO: 7) were prepared by gene synthesis. These segments were flanked by unique restriction sites which allowed for replacement of the corresponding wild type IgG1 sequences. All constructs were designed with a 5'-end DNA sequence coding for a leader peptide, which targets proteins for secretion in eukaryotic cells.

Construction of the Expression Plasmids

A Roche expression vector was used for the construction of all antibody chains. The vector is composed of the following elements:

- an origin of replication, oriP, of Epstein-Barr virus (EBV),
- an origin of replication from the vector pUC18 which allows replication of this plasmid in *E. coli*
- a beta-lactamase gene which confers ampicillin resistance in *E. coli,*
- the immediate early enhancer and promoter from the human cytomegalovirus (HCMV), the human 1-immunoglobulin polyadenylation ("poly A") signal sequence, and unique HpaI, BclI, and NaeI restriction sites.

The immunoglobulin genes in the order of VH—CL-CH2-CH3 and VL-CH1-CH2-CH3 as well as constructs modified in the 3'region coding for the C-terminus of the antibody chain (CH3) were prepared by gene synthesis and cloned into pGA18 (ampR) plasmids as described. The pG18 (ampR) plasmids carrying the synthesized DNA segments and the Roche expression vector were digested either with HpaI and NaeI or with BclI and NaeI restriction enzymes (Roche Molecular Biochemicals) and subjected to agarose gel electrophoresis. Purified DNA segments were then ligated to the isolated Roche expression vector HpaI/NaeI or BclI/NaeI fragment resulting in the final expression vectors. The final expression vectors were transformed into *E. coli* cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and sequence integrity confirmed by DNA sequencing.

Transient Expression of Immunoglobulin Variants in HEK293 Cells

Recombinant immunoglobulin variants were expressed by transient transfection of human embryonic kidney 293-F cells using the FreeStyle™ (serum-free, suspension culture) 293 Expression System according to the manufacturer's instruction (Invitrogen, USA). Briefly, suspension FreeStyle™ 293-F cells were cultivated in FreeStyle™ 293 Expression medium at 37° C./8% $C0_2$. Cells were seeded in fresh medium at a density of 1-2x$10^6$ viable cells/ml on the day of transfection. DNA-293Fectin™ complexes (cationic lipid-based formulation for transfecting DNA into cells) were prepared in Opti-MEM® I medium (Minimal Essential Medium (MEM) that allows for a reduction of Fetal Bovine Serum supplementation); Invitrogen, USA) using 325 μl of 293Fectin™ (Invitrogen, Germany) and 250 μg of each plasmid DNA in a 1:1 molar ratio for a 250 ml final transfection volume. Antibody containing cell culture supernatants were harvested 7 days after transfection by centrifugation at 14000 g for 30 minutes and filtered through a sterile filter (0.22 μm). Supernatants were stored at −20° C. until purification.

Alternatively, antibodies were generated by transient transfection in HEK293-EBNA cells. Antibodies were expressed by transient co-transfection of the respective expression plasmids in adherently growing HEK293-EBNA cells (human embryonic kidney cell line 293 expressing Epstein-Barr-Virus nuclear antigen; American type culture collection deposit number ATCC # CRL-10852, Lot. 959 218) cultivated in DMEM (Dulbecco's modified Eagle's medium, Gibco) supplemented with 10% Ultra Low IgG FCS (fetal calf serum, Gibco), 2 mM L-Glutamine (Gibco), and 250 μg/ml Geneticin (Gibco). For transfection FuGENE™ (a nonliposomal formulation designed to transfect DNA into cells) Transfection Reagent (Roche Molecular Biochemicals) was used in a ratio of FuGENE™ reagent (μl) to DNA (μg) of 4:1 (ranging from 3:1 to 6:1). Proteins were expressed from the respective plasmids using an equimolar ratio of plasmids. Cells were fed at day 3 with L-Glutamine and 4 mM, Glucose [Sigma] and NAA [Gibco]. Immunoglobulin variants containing cell culture supernatants were harvested from day 5 to 11 after transfection by centrifugation and stored at −80 C. General information regarding the recombinant expression of human immunoglobulins in e.g. HEK293 cells is given in: Meissner, P., et al., Biotechnol. Bioeng. 75 (2001) 197-203.

Purification of Antibodies

Antibodies were purified from cell culture supernatants by affinity chromatography using Protein SEPHAROSE® (GE Healthcare, Sweden) and SUPERDEX®200 size exclusion chromatography. Briefly, sterile filtered cell culture supernatants were applied on a HITRAP® (prepacked SEPHAROSE®) ProteinA HP (5 ml) column equilibrated with PBS buffer (10 mM $Na_2HPO_4$, 1 mM $KH_2PO_4$, 137 mM NaCl and 2.7 mM KC1, pH 7.4). Unbound proteins were washed out with equilibration buffer. Antibody and antibody variants were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a SUPERDEX® 200 HiLoad 120 ml 16/60 or 26/60 gel filtration column (GE Healthcare, Sweden) equilibrated with 20 mM Histidin, 140 mM NaCl, pH 6.0. Fractions containing purified antibodies with less than 5% high molecular weight aggregates were pooled and stored as 1.0 mg/ml aliquots at −80° C.

Analysis of Purified Proteins

The protein concentration of purified protein samples was determined by measuring the optical density (OD) at 280 nm, using the molar extinction coefficient calculated on the basis of the amino acid sequence. Purity and molecular weight of antibodies were analyzed by SDS-PAGE in the presence and absence of a reducing agent (5 mM 1,4-dithiotreitol) and staining with Coomassie brilliant blue. The NuPAGE® Pre-Cast gel system (Invitrogen, USA) was used according to the manufacturer's instruction (4-12% Tris-Glycine gels). The aggregate content of antibody samples was analyzed by high-performance SEC using a SUPERDEX® 200 analytical size-exclusion column (GE Healthcare, Sweden) in 200 mM $KH_2PO_4$, 250 mM KC1, pH 7.0 running buffer at 25° C. 25 μg protein were injected on the column at a flow rate of 0.5 ml/min and eluted isocratic over 50 minutes. For stability analysis, concentrations of 1 mg/ml of purified proteins were incubated at 4° C. and 40° C. for 7 days and then evaluated by high-performance SEC (e.g. HP SEC Analysis (Purified Protein). The integrity of the amino acid backbone of reduced immunoglobulin variant chains was verified by NanoElectrospray Q-TOF mass spectrometry after removal of N-glycans by enzymatic treatment with Peptide-N-Glycosidase F (Roche Molecular Biochemicals).

Mass Spectrometry

The total deglycosylated mass of antibodies was determined and confirmed via electrospray ionization mass spectrometry (ESI-MS). Briefly, 100 μg purified antibodies were deglycosylated with 50 mU N-Glycosidase F (PNGaseF, ProZyme) in 100 mM $KH_2PO/K_2HPO_4$, pH 7 at 37° C. for 12-24 h at a protein concentration of up to 2 mg/ml and subsequently desalted via HPLC on a Sephadex G25 column (GE Healthcare). The mass of the respective antibody chains was determined by ESI-MS after deglycosylation and reduction. In brief, 50 μg antibody in 115 μl were incubated with 60 μl 1M TCEP and 50 μl 8 M Guanidine-hydrochloride subsequently desalted. The total mass and the mass of the reduced antibody chains was determined via ESI-MS on a Q-Star Elite MS system equipped with a NanoMate source. The mass range recorded depends on the samples molecular weight. In general for reduced antibodies the mass range was set from 600-2000 m/z and for non reduced antibodies from 1000-3600 m/z.

SEC-MALLS

SEC-MALLS (size-exclusion chromatography with multi-angle laser light scattering) was used to determine the approximate molecular weight of proteins in solution. According to the light scattering theory, MALLS allows molecular weight estimation of macromolecules irrespective of their molecular shape or other presumptions. SEC-MALLS is based on a separation of proteins according to their size (hydrodynamic radius) via SEC chromatography, followed by concentration- and scattered light-sensitive detectors. SEC-MALLS typically gives rise to molecular weight estimates with an accuracy that allows clear discrimination between monomers, dimers, trimers etc., provided the SEC separation is sufficient.

In this work, the following instrumentation was used: Dionex Ultimate 3000 HPLC; column: SUPEROSE®6 (highly cross-linked, agarose-based size exclusion chromatography media) 10/300 (GE Healthcare); eluent: 1×PBS; flow rate: 0.25 mL/min; detectors: OPTILAB® (refractive index detector) REX (Wyatt Inc., Dernbach), MiniDawn Treos (Wyatt Inc., Dernbach). Molecular weights were calculated with the Astra software, version 5.3.2.13. Protein amounts between 50 and 150 µg were loaded on the column and BSA (Sigma Aldrich) was used as a reference protein.

Dynamic Light Scattering (DLS) Timecourse

Samples (30 µL) at a concentration of approx. 1 mg/mL in 20 mM His/HisCl, 140 mM NaCl, pH 6.0, were filtered via a 384-well filter plate (0.45 µm pore size) into a 384-well optical plate (Corning) and covered with 20 µL paraffin oil (Sigma). Dynamic light scattering data were collected repeatedly during a period of 5 days with a DYNAPRO® DLS plate reader (Wyatt) at a constant temperature of 40° C. Data were processed with DYNAMICS® (software for dynamic light scattering analysis) V6.10 (Wyatt).

Surface Plasmon Resonance

The binding properties of anti-IGF-lR antigen binding proteins and antibodies were analyzed by surface plasmon resonance (SPR) technology using a BIACORE® instrument (Biacore, GE-Healthcare, Uppsala). This system is well established for the study of molecule interactions. It allows a continuous real-time monitoring of ligand/analyte bindings and thus the determination of association rate constants (ka), dissociation rate constants (kd), and equilibrium constants (KD) in various assay settings. SPR-technology is based on the measurement of the refractive index close to the surface of a gold coated biosensor chip. Changes in the refractive index indicate mass changes on the surface caused by the interaction of immobilized ligand with analyte injected in solution. If molecules bind to immobilized ligand on the surface the mass increases, in case of dissociation the mass decreases. For capturing anti-human IgG antibody was immobilized on the surface of a CM5 biosensorchip using amine-coupling chemistry. Flow cells were activated with a 1:1 mixture of 0.1 M N-hydroxysuccinimide and 0.1 M 3-(N,N-dimethylamino)propyl-N-ethylcarbodiimide at a flow rate of 5 µl/min. Anti-human IgG antibody was injected in sodium acetate, pH 5.0 at 10 µg/ml. A reference control flow cell was treated in the same way but with vehicle buffers only instead of the capturing antibody. Surfaces were blocked with an injection of 1 M ethanolamine/HCl pH 8.5. The IGF-1R antibodies were diluted in HBS-P and injected. All interactions were performed at 25° C. (standard temperature). The regeneration solution of 3 M Magnesium chloride was injected for 60 s at 5 µl/min flow to remove any non-covalently bound protein after each binding cycle. Signals were detected at a rate of one signal per second. Samples were injected at increasing concentrations. FIG. 17 depicts the applied assay format. A low loading density with capturing antibody density and IGF-1R antibody was chosen to enforce binding.

For affinity measurements, human FcgIIIa was immobilized to a CM-5 sensor chip by capturing the His-tagged receptor to an anti-His antibody (Penta-His, Qiagen) which was coupled to the surface by standard amine-coupling and blocking chemistry on a SPR instrument (BIOACORE® T100). After FcgRIIIa capturing, 50 nM IGF1R antibodies were injected at 25° C. at a flow rate of 5 µL/min. The chip was afterwards regenerated with a 60 s pulse of 10 mM glycine-HCl, pH 2.0 solution.

Antibody-Dependent Cellular Cytotoxicity Assay (ADCC)

Determination of antibody mediated effector functions by anti-IGF-1R antibodies. In order to determine the capacity of the generated antibodies to elicit immune effector mechanisms antibody-dependent cell cytotoxicity (ADCC) studies were performed. To study the effects of the antibodies in ADCC, DU145 IGF-1R expressing cells (1×106 cells/ml) were labeled with 1 µl per ml BATDA solution (Perkin Elmer) for 25 minutes at 37° C. in a cell incubator. Afterwards, cells were washed four times with 10 ml of RPMI-FM/PenStrep and spun down for 10 minutes at 200×g. Before the last centrifugation step, cell numbers were determined and cells diluted to 1×105 cells/ml in RPMI-FM/PenStrep medium from the pellet afterwards. The cells were plated 5,000 per well in a round bottom plate, in a volume of 50 µl. HuMAb antibodies were added at a final concentration ranging from 25-0.1 µg/ml in a volume of 50 µl cell culture medium to 50 µl cell suspension. Subsequently, 50 µl of effector cells, freshly isolated PBMC were added at an E:T ratio 25:1. The plates were centrifuged for 1 minutes at 200×g, followed by an incubation step of 2 hours at 37° C. After incubation the cells were spun down for 10 minutes at 200×g and 20 µl of supernatant was harvested and transferred to an Optiplate 96-F plate. 200 µl of Europium solution (Perkin Elmer, at room temperature) were added and plates were incubated for 15 minutes on a shaker table. Fluorescence is quantified in a time-resolved fluorometer (Victor 3, Perkin Elmer) using the Eu-TDA protocol from Perkin Elmer. The magnitude of cell lysis by ADCC is expressed as % of the maximum release of TDA fluorescence enhancer from the target cells lysed by detergent corrected for spontaneous release of TDA from the respective target cells.

IGF-1R Internalization Assay

The binding of antibodies and antigen binding protein according the invention to the IGF-1R results in internalization and degradation of the receptor. This process can be monitored by incubating IGF-1R expressing HT29 CRC cells with IGF-1R targeting antibodies followed by a quantification of remaining IGF-1R protein levels in cell lysates by ELISA.

For this purpose, HT29 cells at 1.5×104 cells/well were incubated in a 96 well MTP in RPMI with 10% FCS over night at 37° C. and 5% CO2 in order to allow attachment of the cells. Next morning, the medium was aspirated and 100 μl anti IGF-1R antibody diluted in RPMI+10% FCS was added in concentrations from 10 nM to 2 pM in 1:3 dilution steps. The cells were incubated with antibody for 18 hours at 37° C. Afterwards, the medium was again removed and 120 μl MES lysis buffer (25 mM MES pH 6.5+Complete) were added.

For ELISA, 96-Well streptavidin coated polystyrene plates (Nunc) were loaded with 100 μl MAK<hu IGF-1Rα>hu-1a-IgG-Bi (Ch. 10) diluted 1:200 in 3% BSA/PBST (final concentration 2.4 μg/ml) and incubated under constant agitation for 1 hour at room temperature. Afterwards, the well content was removed and each well was washed three times with 200 μl PBST. 100 μl of the cell lysate solution were added per well, again incubated for 1 hour at room temperature on a plate shaker, and washed three times with 200 μl PBST. After removal of the supernatant, 100 μl/well PAK<human IGF-1Rα>Ra—C20-IgG (Santa Cruz # sc-713) diluted 1:750 in 3% BSA/PBST was added followed by the same incubation and washing intervals as described above. In order to detect the specific antibody bound to IGF-1R, 100 μl/well of a polyclonal horse-radish-peroxidase-coupled rabbit antibody (Cell Signaling #7074) diluted 1:4000 in 3% BSA/PBST were added. After another hour, unbound antibody was again removed by washing thoroughly 6 times as described above. For quantification of bound antibody, 100 μl/well 3,3'-5,5'-Tetramethylbenzidin (Roche, BM-Blue ID.-Nr.11484281) was added and incubated for 30 minutes at room temperature. The colorigenic reaction is finally stopped by adding 25 μl/well 1M H2SO4 and the light absorption is measured at 450 nm wavelength. Cells not treated with antibody are used as a control for 0% downregulation, lysis buffer as background control.

IGF-1R Autophosphorylation Assay (IGF-1 Stimulation)

Targeting IGF-1R by IGF-1R antibodies results in inhibition of IGF-1 induced autophosphorylation. We investigated the inhibition of autophosphorylation of the wild type IGF-1R MoAb-Dimer compared to the parental IGF-1R IgG1 antibody. For this purpose 3T3-IGF-1R cells, a murine fibroblast cell line overexpressing human IGF-1R, were treated for 10 minutes with 10 nM recombinant human IGF-1 in the presence of different concentrations of IGF-1R antibody or IGF-1R antigen binding protein. After lysis of the cells, the levels of phosphorylated IGF-1R protein were determined by a phospho-IGF-1R specific ELISA, combining a human IGF-1R specific capture antibody and a phospho-Tyrosine specific detection antibody.

Determination of PK Properties: Single Dose Kinetics in Mice

Methods

Animals

NMRI mice, female, fed, 23-32 g body weight at the time point of compound administration.

Study Protocol

For a single i.v. dose of 10 mg/kg the mice were allocated to 3 groups with 2-3 animals each. Blood samples are taken from group 1 at 0.5, 168 and 672 hours, from group 2 at 24 and 336 hours and from group 3 at 48 and 504 hours after dosing.

Blood samples of about 100 μL were obtained by retrobulbar puncture. Serum samples of at least 40 μl were obtained from blood after 1 hour at room temperature by centrifugation (9300×g) at room temperature for 2.5 min. Serum samples were frozen directly after centrifugation and stored frozen at −20° C. until analysis.

Analytics

The concentrations of the human antibodies in mice serum were determined with an enzyme linked immunosorbent assay (ELISA) using 1% mouse serum. Biotinylated monoclonal antibody against human Fcγ (mAb<hFc$\gamma_{PAN}$>IgG-Bi) was bound to streptavidin coated microtiterplates in the first step. In the next step serum samples (in various dilutions) and reference standards, respectively, were added and bound to the immobilized mAb<hFc$\gamma_{PAN}$>IgG-Bi. Then digoxigenylated monoclonal antibody against human Fcγ (mAb<hFc$\gamma_{PAN}$>IgG-Dig) was added. The human antibodies were detected via anti-Dig-horseradish-peroxidase antibody-conjugate. ABTS-solution was used as the substrate for horseradish-peroxidase. The specificity of the used capture and detection antibody, which does not cross react with mouse IgG, enables quantitative determination of human antibodies in mouse serum samples.

Calculations

The pharmacokinetic parameters were calculated by non-compartmental analysis, using the pharmacokinetic evaluation program WinNonlin™, version 5.2.1.

TABLE 1

Computed Pharmacokinetic Parameters:

| Abbreviations of Pharmacokinetic Parameters | Pharmacokinetic Parameters | Units |
|---|---|---|
| C0 | initial concentration estimated only for bolus IV models | μg/mL |
| C0_NORM | initial concentration estimated only for bolus IV models, dose-normalized | μg/mL/mg/kg |

TABLE 1-continued

| Computed Pharmacokinetic Parameters: | | |
|---|---|---|
| Abbreviations of Pharmacokinetic Parameters | Pharmacokinetic Parameters | Units |
| T0 | time at initial concentration estimated only for bolus IV models | h |
| TMAX | time of maximum observed concentration | h |
| CMAX | maximum observed concentration, occurring at TMAX | μg/mL |
| CMAX_NORM | Cmax, dose-normalized | μg/mL/mg/kg |
| AUC_0_INF | AUC extrapolated | h*μg/mL |
| AUC_0_LST | AUC observed | h*μg/mL |
| TLAST | Time of last observed concentration > 0 | h |
| AUC_0_INF_NORM | AUC extrapolated, dose-normalized | h*μg/mL/mg/kg |
| AUC_0_LST_NORM | AUC observed, dose-normalized | h*μg/mL/mg/kg |
| PCT_AUC_EXTRA | percentage AUC extrapolated | % |
| CL_TOTAL | total clearance | mL/min/kg |
| CL_TOTAL_CTG | total clearance categories | L, M, H |
| VSS | steady state distribution volume | L/kg |
| VSS_CTG | steady state distribution volume categories | L, M, H |
| VZ | terminal distribution volume | L/kg |
| CL/F | total clearance after non IV routes or after IV route of prodrug | mL/min/kg |
| VZ/F | terminal distribution volume after non IV routes or after IV route of prodrug | L/kg |
| MRT_INF | mean residence time (extrapolated) | h |
| MRT_LST | mean residence time (observed) | h |
| HALFLIFE_Z | terminal halflife | h |
| F | bioavailability after non IV routes or after IV route of prodrug | % |

The following pharmacokinetic parameters were used for assessing the human antibodies:

The initial concentration estimated for bolus IV models (C0).

The maximum observed concentration ($C_{max}$), occurring at ($T_{max}$).

The time of maximum observed concentration ($T_{max}$).

The area under the concentration/time curve AUC(0–inf) was calculated by linear trapezoidal rule (with linear interpolation) from time 0 to infinity.

The apparent terminal half-life ($T_{1/2}$) was derived from the equation: $T_{1/2}=\ln 2/\lambda z$.

Total body clearance (CL) was calculated as Dose/AUC (0–inf).

Volume of distribution at steady state (Vss), calculated as MRT(0–inf)×CL (MRT(0–inf), defined as AUMC(0–inf)/AUC(0–inf).

B. Examples

Example 1

Generation of MoAb-Dimer Antigen Binding Proteins

We designed antigen binding proteins according to the invention against c-Met (SEQ ID NO:1 and SEQ ID NO:2), IGF-1R (SEQ ID NO:3 and SEQ ID NO:4) and HER3 (SEQ ID NO:5 and SEQ ID NO:6) based on the design principle as shown in FIG. 1A. The respective constructs were transiently expressed in HEK293 cells as described above, and subsequently purified via Protein A affinity chromatography followed by size exclusion. FIGS. 2-4 depict the chromatograms of the size exclusion chromatography of the three different productions of antigen binding proteins as well as the corresponding SDS-PAGE under non-reducing and reducing conditions. In addition to peak 3 in FIG. 2, peak 2 in FIG. 3, peak 3 in FIG. 4 proteins eluting at earlier timepoints from the column peak 2 in FIG. 2, peak 1 in FIG. 3, peak 4 in FIG. 7 were observed. Based on their retention time it was calculated that they exhibited the double the molecular weight of the monovalent antibody (FIG. 1B, MoAb) corresponding to antigen binding protein according to FIG. 1A (MoAb-Dimer).

The size of the two peaks 1 and 2 for the IGF-1R antibodies was confirmed by SEC-MALLS (FIG. 3C) and showed indeed that the protein corresponding to peak 1 exhibited ca. double the molecular weight of the monovalent antibody (peak 2). The existence of a MoAb-Dimer and the identity of the isolated proteins was subsequently confirmed by mass spectrometry. Based on those findings we derived a model for the structure of the MoAb-Dimer that is depicted in FIG. 1A.

We have performed experiments such as mass spectrometry, reduction and protease digestion to confirm the putative structure shown in FIG. 1A.

The stability of the IGF1R AK18 MoAb-Dimer ("CH3-wt") is studied by dynamic light scattering as described above. Briefly, aggregation tendency of the IGF1R AK18 MoAb-Dimer ("CH3-wt") is assessed by a DLS timecourse experiment at 40° C.

Example 2

IGF-1R Binding Affinity

IGF-1R extracellular domain binding of the IGF1R AK18 MoAb-Dimer ("CH3-wt") was compared to the binding of the parental <IGF-1R> IgG1 antibody by surface Plasmon resonance (SPR). FIG. 5 depicts the scheme of the SPR assay to determine the affinity. The analysis (double determination) showed that the IGF-1R binding affinity is retained in the IGF1R AK18 MoAb-Dimer ("CH3-wt").

| | k(on) | k(off) | KD |
|---|---|---|---|
| Mab (IGF-1R) | 1.74E+06 | 6.63E−03 | 3.80E−09 |
| MoAb-Dimer (IGF-1R) (1. deter.) | 1.5E+06 | 3.0E−03 | 2.01E−09 |
| MoAb-Dimer (IGF-1R) (2. deter.) | 1.5E+06 | 3.0E−03 | 2.05E−09 |

Example 3

Cellular Binding to IGF-1R Expressing Cell Lines

Cellular binding of IGF-1R MoAb-Dimer was demonstrated on A549 cells. A549 cells in the logarithmic growth phase were detached with accutase (Sigma) and 2x10e5 cells were used for each individual antibody incubation. IGF-1R antibody and MoAb-Dimer were added in a three-fold dilution series (100-0.0003 μg/mL). Bound antibodies were visualized with a secondary Alexa488-coupled antibody (5 μg/mL) binding to the constant region of human immunoglobulin. Dead cells were stained with 7-AAD (BD) and excluded from the analysis. Fluorescence intensity of single cells was measured on a FACS Canto (BD Biosciences) flow cytometer. The data show that the MoAb-Dimer showed very similar halfmaximal binding to cells comparable to the parental IGF-1R IgG1 antibody. This implies that the MoAb-Dimer can bind with two arms to IGF-1R on cells and exhibits an avidity effect. However, the total mfi (mean fluorescence intensity) is higher for the MoAb-Dimer than the MAb IGF-1R. This is likely due to the higher number of Fc parts per molecule of IGF-1R on the cell surface. Results are shown in FIG. 6 and below.

| | half-maximal binding |
|---|---|
| IGF-1R (150 kDa): | 0.76 nM |
| IGF-1R MoAb-Dimer (200 kDa): | 1.13 nM |

Example 4

ADCC Induction

Donor-derived peripheral blood mononuclear cells (PBMC) can be used to measure effector cell recruitment by non-glycoengineered and glycoengineered antibodies to cancer cells. Lysis of cancer cells correlates with NK cell mediated cytotoxicity and is proportional to the antibody's ability to recruit NK cells. In this particular setting, DU145 prostate cancer cells were incubated in a 1:25 ratio (DU145: PBMC) ratio with PBMC in the absence or presence of the respective antibodies. After 2 hours cellular lysis was determined using the BATDA/Europium system as described above. The magnitude of cell lysis by ADCC is expressed as % of the maximum release of TDA fluorescence enhancer from the target cells lysed by detergent corrected for spontaneous release of TDA from the respective target cells. The data show that the non-glycoengineered bivalent IGF-1R MoAb-Dimer is superior in inducing ADCC compared to the non-glycoengineered IGF-1R antibody. Surprisingly, the non-glycoengineered IGF-1R MoAb-Dimer is even superior in inducing ADCC at high concentrations compared to the glycoengineered IGF-1R antibody that shows a drop in the ADCC assay going to high concentrations. The superior ADCC induction by the MoAb-Dimer in absence of glycoenginnering can be explained by the higher affinity of the construct for FcgRIIIa on NK cells due to bivalency for FcgRIIIa (avidity effect).

Results for non-glycoengineered IGF1R MAb (1), glycoengineered, afucosylated IGF1R MAb (2) and non-ge IGF1R AK18 MoAb-Dimer ("CH3-wt") (3) are presented in FIG. 7, showing that the MoAb-Dimer IGF1R AK18 MoAb-Dimer ("CH3-wt") has improved ADCC compared to the non-glycoengineered IGF1R MAb and in higher concentrations even compared to glycoengineered, afucosylated IGF1R MAb (2).

Example 5

IGF-1R Internalization Assay

The targeting of IGF-1R on tumor cells by bivalent IGF-1R antibodies results in internalization and lysosomal degradation of IGF-1R. We investigated the internalization properties of the IGF-1R MoAb-Dimer in comparison to the parental IGF-1R parental antibody. For this purpose, HT29 colon cancer cells were treated for 18 hours with different concentrations of MoAb-Dimer and parental IGF-1R antibody. After lysis of the cells, the remaining levels of IGF-1R protein were determined by IGF-1R specific ELISA.

The data in FIG. 8 show that internalization of IGF-1R by the MoAb-Dimer is virtually identical with the bivalent parental IGF-1R parental antibody. Maximum internalization was 82.99% (IgG1) versus 83.7% (MoAb-Dimer), the concentration required for halfmax inhibition was 0.027 nM (IgG1) versus 0.027 nM (MoAb-Dimer).

Example 6

IGF-1R Autophosphorylation (IGF-1 Stimulation)

Targeting IGF-1R by IGF-1R antibodies results in inhibition of IGF-1 induced autophosphorylation. We investigated the inhibition of autophosphorylation of the MoAb-Dimer IGF-1R antibody compared to the parental IGF-1R IgG1 antibody. For this purpose 3T3-IGF-1R cells, a murine fibroblast cell line overexpressing human IGF-1R, were treated for 10 minutes with 10 nM recombinant human IGF-1 in the presence of different concentrations of IGF-1R antibody and antigen binding protein. After lysis of the cells, the levels of phosphorylated IGF-1R protein were determined by a phospho-IGF-1R specific ELISA, combining a human IGF-1R specific capture antibody and a phospho-Tyrosine specific detection antibody.

The data in FIG. 9 shows that the IGF-1R MoAb-Dimer can inhibit IGF-1 induced autophosphorylation similar or even slightly better compared to the IGF-1R IgG1 parental molecule. The concentration required for halfmax inhibition was 1.44 nM (parental IGF-1R IgG1) versus 3.52 nM (MoAb-Dimer), the maximum inhibition observed was 80.3% (parental IGF-1R IgG1) versus 89.1% (MoAb-Dimer).

Example 7

Determination of PK Properties

Pharmacokinetic properties of the antigen binding proteins according to the invention were determined in NMRI mice, female, fed, 23-32 g body weight at the time point of compound administration mice in a single dose PK study, as described above (in the methods sections).

The PK properties are given in the subsequent table and indicate that antigen binding protein IGF1R AK18 MoAb-Dimer ("CH3-wt") has highly valuable PK properties compared to the parental <IGF-1R> IgG1 antibody (like e.g. AuC0-inf, Cmax or C0).

TABLE 2

PK properties

| | | <IGF-1R> IgG1 antibody | <IGF1R> MoAb-Dimer |
|---|---|---|---|
| C0 | µg/mL | 81.9 | 201.56 |
| Cmax | µg/mL | 80.7 | 195.9 |
| Tmax | h | 0.5 | 0.5 |
| AUC0-inf | h*µg/mL | 9349 | 12096 |
| term t½ | h | 106.2 | 83.5 |
| C1 | mL/min/kg | 0.018 | 0.013 |
| Vss | L/kg | 0.16 | 0.1 |

Example 8

ESI-MS Experiment IGF-1R MoAb-Dimer

The IGF-1R MoAb-Dimer (IGF1R AK18 MoAb ("CH3-wt")) (SEQ ID NO: 3 and SEQ ID NO: 4) was transiently expressed and purified via Protein A affinity and size exclusion chromatography. After preparative SEC (see FIG. 3A) the antibody eluted within two separate peaks, which were collected. Analytical SEC from the first peak (fraction 1) shows an apparent molecular weight of approximately 200 kDa, where as the second peak (fraction 2) corresponds to a molecular weight of 100 kDa. The different molecular weights could be assigned to a defined monomer as by product (fraction 2) and the desired dimer (fraction 1) respectively. SEC-MALS confirmed the initial SEC result and shows for the fraction 2 (monomer) a MW of 99.5 kDa and for the fraction 1 (dimer) a MW of 193.8 kDa.

SDS-PAGE analysis (see FIG. 3B) of the two fractions under denaturing and reducing conditions shows one major band with an apparent molecular weight of 50-60 kDa. Under non reducing conditions fraction 2 shows a major band around a MW of 100 kDa and fraction 1 shows a very broad band ranging from about 100-200 kDa.

Fraction 1=165 mL

Fraction 2=190 mL

These initial data show the dimer formation.

ESI-MS spectra (samples incubated with 60 µl 1M TCEP and 50 µl 8 M Guanidine-hydrochloride) of deglycosylated MoAb Dimer from fraction 1 and MoAb monomer fraction 2 show differences. Fraction 2 shows only one peak series corresponding to a monomer with a mass of 98151 Da whereas fraction 1 shows 2 different envelops containing two major peak series corresponding to a mass of 98155 Da (monomer) and a second series with a mass of 196319 Da (dimer).

TABLE 3

Summary of MS data from non reducing ESI-MS measurements from fraction 1 and 2.

| Fraction | Molecular weight, monomer (theor. 98162 Da) | Molecular weight, dimer (theor. 196324 Da) |
|---|---|---|
| Fraction 1 | 98155 Da | 196319 Da |
| Fraction 2 | 98151 Da | Not detected |

The presence of a monomer in fraction 1 may be explained by the incubation conditions (incubated with 60 µl 1M TCEP and 50 µl 8 M Guanidine-hydrochloride) and a potential open S-S bridge between CH1-Ck. In this case, the transfer from an aqueous to an acidic organic solvent during sample preparation for MS can cause the dissociation of the dimer into 2 monomers.

This is in accordance to the results from the CE-SDS (BioAnalyzer) analysis. Fraction 1 contains 71% dimer and 16% monomer under non-reducing conditions. The use of SDS separates non-covalently linked chains. Fraction 2 shows only one monomer signal (98%) under non-reducing conditions.

MS measurements under reducing conditions of fraction 1 and fraction 2 show the correct sequence and expression of the constructs. The MS data from fraction 1 show two different heavy chains with a molecular weight of 47960 Da and 50208 Da in approximately equal amounts. These two heavy chains were also found in fraction 2 with similar intensities.

TABLE 4

Summary of MS data from reducing ESI-MS measurements under reducing conditions from fraction 1 and 2.

| Fraction | Molecular weight, heavy chain 1 (theor. 50226 Da) | Molecular weight, heavy chain 2 (theor. 47961 Da) |
|---|---|---|
| Fraction 1 | 50208 Da (pyro Glu at N-term.) | 47960 Da |
| Fraction 2 | 50211 Da (pyro Glu at N-term.) | 47959 Da |

Example 9

Analysis of MoAb-Dimer Versus Monovalent Monomer Ratios in CH3 Wt and CH3-Modified IGF1R AK18 MoAb-Dimer Antigen Binding Proteins Modifications of the CH3 domains, of the antibody chains can change the ratios of and MoAb-Dimer and MoAb-monomer. Exemplary, different heavy chain modifications were transiently expressed in HEK293F cells together or in combination with the unmodified heavy chain. For comparison, antibody comprising unmodified heavy chains was transiently transfected in parallel. Supernatant containing the antibodies was harvested seven days after transfection. Antibody was precipitated using Protein A sepharose and eluted from the beads with a standard pH shock protocol. Obtained eluates were subjected to a HPLC analysis using a G3000SW (TSKGel) column. Antibody ratios were quantified calculating the area under the respective peaks. The term "CH3-wt" refers to a IgG1 CH3 domain with natural sequence (wild type=wt).

TABLE 5

Obtained MoAb-dimer (=bivalent antigen binding protein according to the invention) versus MoAb-monomer (=monovalent byproduct) ratios as determined by HPLC. Both desired dimeric product and monomeric byproduct can be easily seperated. Values were derived from the chromatograms displayed in FIG. 10.

| Sample | Combination of modified heavy chains a) VL-CH1-CH2-CH3/ b) VH-CL-CH2-CH3 | % Moab-Dimer | % Moab (Monomer) |
|---|---|---|---|
| A | CH3-wt (SEQ ID NO: 3)/CH3-wt (SEQ ID NO: 4) | 30 | 70 |
| B | CH3-wt (SEQ ID NO: 3)/1 (SEQ ID NO: 4 with mutations S364F and L368G) | 25 | 75 |
| C | m (SEQ ID NO: 3 with the mutations S364G, L368F, D399K, and K409D)/CH3-wt (SEQ ID NO: 4) | 98.5 | 1.5 |
| D | m (SEQ ID NO: 3 with the mutations S364G, L368F, D399K and K409D)/1 (SEQ ID NO: 4 with mutations S364F and L368G) | 17 | 83 |
| E | CH3-wt (SEQ ID NO: 3)/h (SEQ ID NO: 4 with mutations S364W and L368G) | 20 | 80 |
| F | i (SEQ ID NO: 3 with the mutations S364G, L368W, D399K and K409D)/CH3-wt (SEQ ID NO: 4) | — | — |
| G | i (SEQ ID NO: 3 with the mutations S364G, L368W, D399K and K409D)/h (SEQ ID NO: 4 with mutations S364W and L368G) | — | — |
| H | CH3- IgA ((SEQ ID NO: 7)/CH3-wt (SEQ ID NO: 4) | 100 | 0 |

h = mutant with the mutations S364W and L368G in the IgG1 CH3 domain
i = mutant with the mutations S364G, L368W, D399K and K409D in the IgG1 CH3 domain.
l = mutant with the mutations S364F and L368G in the IgG1 CH3 domain
m = mutant with the mutations S364G, L368F, D399K and K409D in the IgG1 CH3 domain.
CH3-wt = IgG1 wt CH3 domain
CH3- IgA = chimer with a IgG1 CH2 domain and IgA CH3 domain

Example 10

Production of Glycoengineered Antibodies

For the production of the glycoengineered MoAb antigen binding protein, HEK-EBNA cells are transfected, using the calcium phosphate method, with four plasmids. Two encoding the antibody chains, one for a fusion GnTIII polypeptide expression (a GnT-III expression vector), and one for mannosidase II expression (a Golgi mannosidase II expression vector) at a ratio 4:4:1:1, respectively. Cells are grown as adherent monolayer cultures in T flasks using DMEM culture medium supplemented with 10% FCS, and are transfected when they are between 50 and 80% confluent. For the transfection of a T150 flask, 15 million cells are seeded 24 hours before transfection in 25 ml DMEM culture medium supplemented with FCS (at 10% V/V final), and cells are placed at 37° C. in an incubator with a 5% $CO_2$ atmosphere overnight. For each T150 flask to be transfected, a solution of DNA, $CaCl_2$ and water is prepared by mixing 94 µg total plasmid vector DNA divided equally between the light and heavy chain expression vectors, water to a final volume of 469 µl and 469 µl of a 1M $CaCl_2$ solution. To this solution, 938 µl of a 50 mM HEPES, 280 mM NaCl, 1.5 mM $Na_2HPO_4$ solution at pH 7.05 are added, mixed immediately for 10 sec and left to stand at room temperature of 20 sec. The suspension is diluted with 10 ml of DMEM supplemented with 2% FCS, and added to the T150 in place of the existing medium. Then additional 13 ml of transfection medium are added. The cells are incubated at 37° C., 5% $CO_2$ for about 17 to 20 hours, then medium is replaced with 25 ml DMEM, 10% FCS. The conditioned culture medium is harvested approx. 7 days post-media exchange by centrifugation for 15 min at 210×g, the solution is sterile filtered (0.22 um filter) and sodium azide in a final concentration of 0.01% w/v is added, and kept at 4° C.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method for the preparation of an antigen binding protein comprising the steps of a) transforming an isolated host cell with isolated vectors comprising nucleic acid molecules encoding the antigen binding protein, b) culturing the isolated host cell under conditions that allow synthesis of said antigen binding protein molecule; and c) recovering said antigen binding protein molecule from said culture; wherein the antigen binding protein comprises i) two modified heavy chains of an antibody which specifically binds to an antigen, wherein VH of each heavy chain is replaced by the VL of said antibody, said modified heavy chains being associated with each other via their CH3 domains of the Fc part; and ii) two modified heavy chains of said antibody wherein CH1 of each heavy chain is replaced by CL of said antibody, said modified heavy chains being associated with each other via their CH3 domains of the Fc part;

and wherein the VL domains of the heavy chains of i) are associated with the VH domains of the heavy chains of ii), and the CH1 domains of the heavy chains of i) are associated with the CL domains of the heavy chains of ii);

wherein the CH2 and CH3 domains of the Fc part of the modified heavy chains of i) and the CH2 and CH3 domains of the Fc part of the modified heavy chains of ii) are of the human IgG1 isotype; and wherein either the two modified heavy chains of i), or the two modified heavy chains of ii), are further modified by the amino acid substitutions S364G, L368F, D399K and K409D, wherein the amino acid positions are numbered according to the EU Index of Kabat, and wherein the other two modified heavy chains comprise wild type CH3 amino acid sequences.

2. An isolated nucleic acid encoding an antigen binding protein, wherein the antigen binding protein comprises i) two modified heavy chains of an antibody which specifically binds to an antigen, wherein VH of each heavy chain is replaced by the VL of said antibody, said modified heavy chains being associated with each other via their CH3 domains of the Fc part; and ii) two modified heavy chains of said antibody wherein CH1 of each heavy chain is replaced by CL of said antibody, said modified heavy chains being associated with each other via their CH3 domains of the Fc part;

and wherein the VL domains of the heavy chains of i) are associated with the VH domains of the heavy chains of ii), and the CH1 domains of the heavy chains of i) are associated with the CL domains of the heavy chains of ii), wherein the CH2 and CH3 domains of the Fc part of the modified heavy chains of i) and the CH2 and CH3 domains of the Fc part of the modified heavy chains of ii) are of the human IgG1 isotype; and wherein either the two modified heavy chains of i), or the two modified heavy chains of ii), are further modified by the amino acid substitutions S364G, L368F, D399K and K409D, wherein the amino acid positions are numbered according to the EU Index of Kabat, and wherein the other two modified heavy chains comprise wild type CH3 amino acid sequences.

3. An isolated vector comprising the isolated nucleic acid according to claim 2.

4. An isolated host cell comprising the isolated vector according to claim 3.

5. The method of claim 1, wherein the antigen binding protein comprises a) i) two modified heavy chains comprising the amino acid sequence of SEQ ID NO:1; and ii) two modified heavy chains comprising the amino acid sequence of SEQ ID NO:2;

wherein either the two modified heavy chains of i), or the two modified heavy chains of ii), are further modified by the amino acid substitutions S364G, L368F, D399K and K409D, wherein the amino acid positions are numbered according to the EU Index of Kabat;

b) i) two modified heavy chains comprising the amino acid sequence of SEQ ID NO:3; and ii) two modified heavy chains comprising the amino acid sequence of SEQ ID NO:4;

wherein either the two modified heavy chains of i), or the two modified heavy chains of ii), are further modified by the amino acid substitutions S364G, L368F, D399K and K409D, wherein the amino acid positions are numbered according to the EU Index of Kabat; or b) i) two modified heavy chains comprising the amino acid sequence of SEQ ID NO:5; and ii) two modified heavy chains comprising the amino acid sequence of SEQ ID NO:6 wherein either the two modified heavy chains of i), or the two modified heavy chains of ii), are further modified by the amino acid substitutions S364G, L368F, D399K and K409D, wherein the amino acid positions are numbered according to the EU Index of Kabat.

* * * * *